(12) United States Patent
Nakamura et al.

(10) Patent No.: US 9,139,655 B2
(45) Date of Patent: Sep. 22, 2015

(54) TUMOR-TARGETING MONOCLONAL ANTIBODIES TO FZD10 AND USES THEREOF

(75) Inventors: Yusuke Nakamura, Tokyo (JP);
Toyomasa Katagiri, Tokyo (JP);
Shuichi Nakatsuru, Kanagawa (JP);
Keigo Endo, Gunma (JP)

(73) Assignee: ONCOTHERAPY SCIENCE, INC., Kawasaki-Shi (JP)

( * ) Notice: Subject to any disclaimer, the term of this patent is extended or adjusted under 35 U.S.C. 154(b) by 495 days.

(21) Appl. No.: 13/494,822

(22) Filed: Jun. 12, 2012

(65) Prior Publication Data

US 2013/0230521 A1    Sep. 5, 2013

Related U.S. Application Data

(62) Division of application No. 12/308,095, filed as application No. PCT/JP2006/317155 on Aug. 24, 2006, now Pat. No. 8,221,751.

(60) Provisional application No. 60/815,257, filed on Jun. 21, 2006.

(51) Int. Cl.
| *C07K 16/30* | (2006.01) |
|---|---|
| *A61K 49/00* | (2006.01) |
| *A61K 51/10* | (2006.01) |
| *C07K 16/28* | (2006.01) |
| *G01N 33/574* | (2006.01) |
| *A61K 39/00* | (2006.01) |

(52) U.S. Cl.
CPC ............. *C07K 16/30* (2013.01); *A61K 49/0002* (2013.01); *A61K 49/0021* (2013.01); *A61K 49/0041* (2013.01); *A61K 49/0058* (2013.01); *A61K 51/1027* (2013.01); *C07K 16/2896* (2013.01); *G01N 33/57407* (2013.01); *G01N 33/57419* (2013.01); *G01N 33/57426* (2013.01); *G01N 33/57446* (2013.01); *A61K 2039/505* (2013.01); *C07K 2317/24* (2013.01)

(58) Field of Classification Search
CPC ........... A61K 49/0058; A61K 51/1027; A61K 2039/505; C07K 16/30; G01N 33/57407
USPC ................................ 424/135.1, 133.1, 174.1
See application file for complete search history.

(56) References Cited

U.S. PATENT DOCUMENTS

| 6,964,849 B2 | 11/2005 | Rastelli et al. |
|---|---|---|
| 2001/0011124 A1 | 8/2001 | Hu et al. |
| 2003/0044409 A1 | 3/2003 | Carson et al. |
| 2003/0215449 A1 | 11/2003 | Mezes et al. |
| 2004/0247593 A1 | 12/2004 | He et al. |

FOREIGN PATENT DOCUMENTS

| EP | 0943684 A2 | 9/1999 |
|---|---|---|
| EP | 1001023 A2 | 5/2000 |
| JP | 11-075866 | 3/1999 |
| JP | 11-253183 | 9/1999 |
| JP | 2000-093186 | 4/2000 |
| PY | WO 02/16620 A2 | 2/2002 |
| WO | WO 96/02641 A | 2/1996 |
| WO | WO 01/74405 A1 | 10/2001 |
| WO | WO 02/055705 A2 | 7/2002 |
| WO | WO 02/086443 A2 | 10/2002 |
| WO | WO 02/088081 A2 | 11/2002 |
| WO | WO 02/092635 A2 | 11/2002 |
| WO | WO 03/004045 A2 | 1/2003 |
| WO | WO 2004/020668 A2 | 3/2004 |
| WO | WO 2005/004912 A1 | 1/2005 |
| WO | WO 2006/013733 A1 | 2/2006 |

OTHER PUBLICATIONS

Fukukawa et al. Oncogene 28:1110-1120 (2009).*
U.S. Office Action dated Oct. 1, 2012 for U.S. Appl. No. 12/769,599.
Beckman et al., "Antibody Constructs in Cancer Therapy", Cancer, vol. 109, 2007, pp. 170-179.
Cespdes et al., "Mouse models in oncogenesis and cancer therapy", Clin. Trans. Oncol., vol. 8, No. 5, 2006, pp. 318-329.
Dennis, "Off by a whisker", Nature Publishing Group, vol. 442, 2006, pp. 739-741.
Fujimori et al., "A Modeling Analysis of Monoclonal Antibody Percolation Through Tumors: A Binding-Site Barrier", J. Nuc. Med., Jan. 1990, vol. 31, pp. 1191-1198.
Fukukawa Chikako et al., Proceedings of the American Association for Cancer Research Annual Meetings, vol. 47, Apr. 2006, p. 465.
Fukukawa et al., "Functional analysis of FZD10, an up-regulated gene in synovial sarcoma, and therapeutic potential of its antibody," 63rd Ann Mtg of Jap Cancer Assoc, Sep.-Oct. 2004, W-148.
Fukukawa et al., "Functional analysis of FZD10, an up-regulated gene in synovial sarcoma, and therapeutic potential of its antibody," 64th Ann Mtg of Jap Cancer Assoc, Sep. 2005, p. 54, W-093.
Fukukawa et al., "Radioimmunotherapy of human synovial sarcoma using a monoclonal antibody against FZD10," 66th Ann Mtg Jap Cancer Assoc, Oct. 2007, p. 77, EW11-4.
Fukukawa et al., "Radioimmunotherapy of human synovial sarcoma using a monoclonal antibody against FZD10," Cancer Sci, Feb. 2008, vol. 99, No. 2, pp. 432-440.

(Continued)

*Primary Examiner* — Lynn Bristol
(74) *Attorney, Agent, or Firm* — Birch, Stewart, Kolasch & Birch, LLP

(57) ABSTRACT

The present invention relates to an antibody or a fragment thereof which is capable of binding to a Frizzled homologue 10 (FZD10) protein, such as a mouse monoclonal antibody, a chimeric antibody and a humanized antibody. Also, the present invention relates to a method for treating and/or preventing FZD10-associated disease; a method for diagnosis or prognosis of FZD10-associated disease; and a method for in vivo imaging of FZD10 in a subject.

19 Claims, 15 Drawing Sheets
(6 of 15 Drawing Sheet(s) Filed in Color)

(56) References Cited

OTHER PUBLICATIONS

Fukukawa et al., "Therapeutic potential of antibodies against FZD10, a cell-surface protein, for synovial sarcomas," AARC, 96th Annual Mtg, Apr. 2005, Anaheim, California, pp. 165-166, Abstract No. 702.
Kamarainen et al., "Epithelial expression of glycodelin in biphasic synovial sarcomas," Int J Cancer, May 18, 1998, vol. 76, No. 4, pp. 487-490.
Katagiri et al., "The development of anti-FZD10 antibody for molecular target therapy in synovial sarcoma," 3rd Jap Cancer Assoc Conf, Mar. 2006, p. 35, O-26.
Kaykas et al., "Mutant Frizzled 4 associated with vitreoretinopathy traps wild-type Frizzled in the endoplasmic reticulum by oligomerization," Nat Cell Biol, Jan. 2004, vol. 6, No. 1, pp. 52-58, Epub Dec. 14, 2003.
Kirikoshi et al., "Expression profiles of 10 members of Frizzled gene family in human gastric cancer," Int J Oncol, Oct. 2001, vol. 19, No. 4, pp. 767-771.
Koike J. et al, Biochemical and Biophysical Research Communications, vol. 262, 1999, pp. 39-43.
Nagayama et al., "A novel molecular classification of soft tissue sarcomas based on expression profiles by means of a genome-wide cDNA microarray analysis," 63rd Ann Mtg Jap Cancer Assoc, Sep.-Oct. 2004, W-149.
Nagayama et al., "Gene Expression Profiles of Synovial Sarcoma," J of Jap Orthopaedic Assoc, 35th Ann Musculoskeletal Tumor Mtg, Jun. 2002, vol. 76, No. 6, p. S735, I-3-P3-5.
Nagayama et al., "Identification of PDZK4, a novel human gene with PDZ domains, that is upregulated in synovial sarcomas," Oncogene, Jul. 15, 2004, vol. 23, No. 32, pp. 5551-5557.
Nagayama et al., "The therapeutic potential of antibodies against cell surface protein, FZD10, for synovial sarcomas," 62nd Ann Mtg Jap Cancer Assoc, Sep. 2003, p. 112, 1171-OP.
Nagayama Satoshi et al., Oncogene, vol. 24, No. 41, Sep. 15, 2005, pp. 6201-6212.
Park et al., "Identification and characterization of MMK-B1 as a molecular target for breast cancer therapy," 65th Ann Mtg Jap Cancer Assoc, Sep. 2006, p. 155, P-230.
Rudnick et al., "Affinity and Avidity in Antibody-Based Tumor Targeting", Cancer Biotherapy and Radiopharmaceuticals, vol. 24, 2009, pp. 155-161.
Saitoh et al., "Up-regulation of Frizzled-10 (FZD10) by beta-estradiol in MCF-7 cells and by retinoic acid in NT2 cells," Int J Oncol, Jan. 2002, vol. 20, No. 1, pp. 117-120.
Satoshi Nagayama et al., "Genome-wide Analysis of Gene Expression in Synovial Sarcomas using a cDNA Microarry", Cancer Research Oct. 15, 2002, vol. 62, pp. 5859-5866.
Talmadge et al., "Murine Models to Evaluate Novel and Conventional Therapeutic Strategies for Cancer", American Journal of Pathology, vol. 170, No. 3, Mar. 2007, pp. 793-804.
Tamborini et al., "c-KIT and c-KIT ligand (SCF) in synovial sarcoma (SS): an mRNA expression analysis in 23 cases," Br J Cancer, Aug. 3, 2001, vol. 85, No. 3, pp. 405-411.
Terasaki et al., "Frizzled-10, up-regulated in primary colorectal cancer, is a positive regulator of the WNT—beta-catenin—TCF signaling pathway," Int J Mol Med, Feb. 2002, vol. 9, No. 2, pp. 107-112.
Thurber et al., "Antibody tumor penetration: Transport opposed by systematic and antigen-mediated clearance", Advance Drug Delivery Reviews, vol. 60, Apr. 2008, pp. 1421-1434.
Umbhauer et al., "The C-terminal cytoplasmic Lys-thr-X-X-X-Trp motif in frizzled receptors mediates Wnt/beta-catenin signalling," EMBO J, Sep. 15, 2000, vol. 19, No. 18, pp. 4944-4954.
Voskoglou-Nomikos et al., "Clinical Predictive Value of the in Vitro Cell Line, Human Xenograft, and Mouse Allograft Preclinical Cancer Models", Clinical Cancer Research, vol. 9, Sep. 2003, pp. 4227-1239.
Yamada et al., "Immunohistochemical study of FZD10 expression in colon adenomas, primary colorectal cancers and metastatic liver lesions," 66th Ann Mtg Jap Cancer Assoc, Oct. 2007, p. 554, P-1379.

* cited by examiner 92-13

93-22

0h   48h   72h   96h   120h a b c d

SEQUENCE LISTING

<160> NUMBER OF SEQ ID NOS: 68

<210> SEQ ID NO 1
<211> LENGTH: 2811
<212> TYPE: DNA
<213> ORGANISM: Homo sapiens

<400> SEQUENCE: 1

| | | | | | |
|---|---|---|---|---|---|
| acacgtccaa | cgccagcatg | cagcgcccgg | gcccccgcct | gtggctggtc | ctgcaggtga | 60 |
| tgggctcgtg | cgccgccatc | agctccatgg | acatggagcg | cccgggcgac | ggcaaatgcc | 120 |
| agcccatcga | gatcccgatg | tgcaaggaca | tcggctacaa | catgactcgt | atgcccaacc | 180 |
| tgatgggcca | cgagaaccag | cgcgaggcag | ccatccagtt | gcacgagttc | gcgccgctgg | 240 |
| tggagtacgg | ctgccacggc | cacctccgct | tcttcctgtg | ctcgctgtac | gcgccgatgt | 300 |
| gcaccgagca | ggtctctacc | cccatccccg | cctgccgggt | catgtgcgag | caggcccggc | 360 |
| tcaagtgctc | cccgattatg | gagcagttca | acttcaagtg | gcccgactcc | ctggactgcc | 420 |
| ggaaactccc | caacaagaac | gaccccaact | acctgtgcat | ggaggcgccc | aacaacggct | 480 |
| cggacgagcc | cacccggggc | tcgggcctgt | tcccgccgct | gttccggccg | cagcggcccc | 540 |
| acagcgcgca | ggagcacccg | ctgaaggacg | ggggccccgg | gcgcggcggc | tgcgacaacc | 600 |
| cgggcaagtt | ccaccacgtg | gagaagacgc | gtcgtgcgc | gccgctctgc | acgcccggcg | 660 |
| tggacgtgta | ctggagccgc | gaggacaagc | gcttcgcagt | ggtctggctg | ccatctggg | 720 |
| cggtgctgtg | cttcttctcc | agcgccttca | ccgtgctcac | cttcctcatc | gacccggccc | 780 |
| gcttccgcta | ccccgagcgc | ccatcatct | tcctctccat | gtgctactgc | gtctactccg | 840 |
| tgggctacct | catccgcctc | ttcgccggcg | ccgagagcat | cgcctgcgac | cgggacagcg | 900 |
| gccagctcta | tgtcatccag | gagggactgg | agagcaccgg | ctgcacgctg | gtcttcctgg | 960 |
| tcctctacta | cttcggcatg | gccagctcgc | tgtggtgggt | ggtcctcacg | ctcacctggt | 1020 |
| tcctggccgc | cggcaagaag | tggggccacg | aggccatcga | agccaacagc | agctacttcc | 1080 |
| acctggcagc | ctgggccatc | ccggcggtga | agaccatcct | gatcctggtc | atgcgcaggg | 1140 |
| tggcggggga | cgagctcacc | ggggtctgct | acgtgggcag | catggacgtc | aacgcgctca | 1200 |
| ccggcttcgt | gctcattccc | ctggcctgct | acctggtcat | cggcacgtcc | ttcatcctct | 1260 |
| cgggcttcgt | ggccctgttc | cacatccgga | gggtgatgaa | gacgggcggc | gagaacacgg | 1320 |
| acaagctgga | gaagctcatg | gtgcgtatcg | ggctcttctc | tgtgctgtac | accgtgccgg | 1380 |
| ccacctgtgt | gatcgcctgc | tacttttacg | aacgcctcaa | catggattac | tggaagatcc | 1440 |
| tggcggcgca | gcacaagtgc | aaaatgaaca | accagactaa | aacgctggac | tgcctgatgg | 1500 |
| ccgcctccat | ccccgccgtg | gagatcttca | tggtgaagat | ctttatgctg | ctggtggtgg | 1560 |
| ggatcaccag | cggatgtgg | atttggacct | ccaagactct | gcagtcctgg | cagcaggtgt | 1620 |
| gcagccgtag | gttaaagaag | aagagccgga | gaaaaccggc | cagcgtgatc | accagcggtg | 1680 |
| ggatttacaa | aaaagcccag | catcccagca | aaactcacca | cgggaaatat | gagatccctg | 1740 |
| cccagtcgcc | cacctgcgtg | tgaacagggc | tggagggaag | ggcacagggg | cgcccggagc | 1800 |
| taagatgtgg | tgcttttctt | ggttgtgttt | ttctttcttc | ttcttctttt | tttttttttt | 1860 |
| ataaaagcaa | aagagaaata | cataaaaaag | tgtttaccct | gaaattcagg | atgctgtgat | 1920 |
| acactgaaag | gaaaaatgta | cttaaagggt | tttgttttgt | tttggttttc | cagcgaaggg | 1980 |
| aagctcctcc | agtgaagtag | cctcttgtgt | aactaatttg | tggtaaagta | gttgattcag | 2040 |
| ccctcagaag | aaaactttg | tttagagccc | tccgtaaata | tacatctgtg | tatttgagtt | 2100 |

```
ggctttgcta cccatttaca aataagagga cagataactg ctttgcaaat tcaagagcct    2160
cccctgggtt aacaaatgag ccatccccag ggcccacccc caggaaggcc acagtgctgg    2220
gcggcatccc tgcagaggaa agacaggacc cggggcccgc ctcacacccc agtggatttg    2280
gagttgctta aaatagactc tggccttcac caatagtctc tctgcaagac agaaacctcc    2340
atcaaacctc acatttgtga actcaaacga tgtgcaatac atttttttct ctttccttga    2400
aaataaaaag agaaacaagt attttgctat atataaagac aacaaagaa atctcctaac    2460 aaaagaacta agaggcccag ccctcagaaa cccttcagtg ctacattttg tggcttttta    2520
atggaaacca agccaatgtt atagacgttt ggactgattt gtggaaagga gggggaaga    2580 gggagaagga tcattcaaaa gttacccaaa gggcttattg actctttcta ttgttaaaca    2640
aatgatttcc acaaacagat caggaagcac taggttggca gagacacttt gtctagtgta    2700
ttctcttcac agtgccagga aagagtggtt tctgcgtgtg tatatttgta atatatgata    2760
tttttcatgc tccactattt tattaaaaat aaaatatgtt ctttaaaaaa a             2811

<210> SEQ ID NO 2
<211> LENGTH: 581
<212> TYPE: PRT
<213> ORGANISM: Homo sapiens

<400> SEQUENCE: 2

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
            20                  25                  30

Lys Cys Gln Pro Ile Glu Ile Pro Met Cys Lys Asp Ile Gly Tyr Asn
        35                  40                  45

Met Thr Arg Met Pro Asn Leu Met Gly His Glu Asn Gln Arg Glu Ala
    50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
    130                 135                 140

Tyr Leu Cys Met Glu Ala Pro Asn Asn Gly Ser Asp Glu Pro Thr Arg
145                 150                 155                 160

Gly Ser Gly Leu Phe Pro Pro Leu Phe Arg Pro Gln Arg Pro His Ser
                165                 170                 175

Ala Gln Glu His Pro Leu Lys Asp Gly Gly Pro Gly Arg Gly Gly Cys
            180                 185                 190

Asp Asn Pro Gly Lys Phe His His Val Glu Lys Ser Ala Ser Cys Ala
        195                 200                 205

Pro Leu Cys Thr Pro Gly Val Asp Val Tyr Trp Ser Arg Glu Asp Lys
    210                 215                 220

Arg Phe Ala Val Val Trp Leu Ala Ile Trp Ala Val Leu Cys Phe Phe
225                 230                 235                 240

Ser Ser Ala Phe Thr Val Leu Thr Phe Leu Ile Asp Pro Ala Arg Phe
```

```
                    245                 250                 255
Arg Tyr Pro Glu Arg Pro Ile Ile Phe Leu Ser Met Cys Tyr Cys Val
                260                 265                 270

Tyr Ser Val Gly Tyr Leu Ile Arg Leu Phe Ala Gly Ala Glu Ser Ile
            275                 280                 285

Ala Cys Asp Arg Asp Ser Gly Gln Leu Tyr Val Ile Gln Glu Gly Leu
        290                 295                 300

Glu Ser Thr Gly Cys Thr Leu Val Phe Leu Val Leu Tyr Tyr Phe Gly
305                 310                 315                 320

Met Ala Ser Ser Leu Trp Trp Val Val Leu Thr Leu Thr Trp Phe Leu
                325                 330                 335

Ala Ala Gly Lys Lys Trp Gly His Glu Ala Ile Glu Ala Asn Ser Ser
            340                 345                 350

Tyr Phe His Leu Ala Ala Trp Ala Ile Pro Ala Val Lys Thr Ile Leu
        355                 360                 365

Ile Leu Val Met Arg Arg Val Ala Gly Asp Glu Leu Thr Gly Val Cys
370                 375                 380

Tyr Val Gly Ser Met Asp Val Asn Ala Leu Thr Gly Phe Val Leu Ile
385                 390                 395                 400

Pro Leu Ala Cys Tyr Leu Val Ile Gly Thr Ser Phe Ile Leu Ser Gly
                405                 410                 415

Phe Val Ala Leu Phe His Ile Arg Arg Val Met Lys Thr Gly Gly Glu
            420                 425                 430

Asn Thr Asp Lys Leu Glu Lys Leu Met Val Arg Ile Gly Leu Phe Ser
        435                 440                 445

Val Leu Tyr Thr Val Pro Ala Thr Cys Val Ile Ala Cys Tyr Phe Tyr
450                 455                 460

Glu Arg Leu Asn Met Asp Tyr Trp Lys Ile Leu Ala Ala Gln His Lys
465                 470                 475                 480

Cys Lys Met Asn Asn Gln Thr Lys Thr Leu Asp Cys Leu Met Ala Ala
                485                 490                 495

Ser Ile Pro Ala Val Glu Ile Phe Met Val Lys Ile Phe Met Leu Leu
            500                 505                 510

Val Val Gly Ile Thr Ser Gly Met Trp Ile Trp Thr Ser Lys Thr Leu
        515                 520                 525

Gln Ser Trp Gln Gln Val Cys Ser Arg Arg Leu Lys Lys Lys Ser Arg
        530                 535                 540

Arg Lys Pro Ala Ser Val Ile Thr Ser Gly Gly Ile Tyr Lys Lys Ala
545                 550                 555                 560

Gln His Pro Gln Lys Thr His His Gly Lys Tyr Glu Ile Pro Ala Gln
                565                 570                 575

Ser Pro Thr Cys Val
            580

<210> SEQ ID NO 3
<211> LENGTH: 22
<212> TYPE: DNA
<213> ORGANISM: Artificial sequence
<220> FEATURE:
<223> OTHER INFORMATION: An artificially synthesized primer for RT-PCR

<400> SEQUENCE: 3
aattttcttg tccaccttgg tg                                             22

<210> SEQ ID NO 4
```

```
<211> LENGTH: 26
<212> TYPE: DNA
<213> ORGANISM: Artificial sequence
<220> FEATURE:
<223> OTHER INFORMATION: An artificially synthesized primer for RT-PCR

<400> SEQUENCE: 4
ctaacactca ttcctgttga agctct                                          26

<210> SEQ ID NO 5
<211> LENGTH: 38
<212> TYPE: DNA
<213> ORGANISM: Artificial sequence
<220> FEATURE:
<223> OTHER INFORMATION: An artificially synthesized primer for PCR

<400> SEQUENCE: 5
aatagcggcc gcaccatgaa atgcagctgg gttatctt                             38

<210> SEQ ID NO 6
<211> LENGTH: 33
<212> TYPE: DNA
<213> ORGANISM: Artificial sequence
<220> FEATURE:
<223> OTHER INFORMATION: An artificially synthesized primer for PCR

<400> SEQUENCE: 6
aatagctagc tgcagagaca gtgaccagag tcc                                  33

<210> SEQ ID NO 7
<211> LENGTH: 34
<212> TYPE: DNA
<213> ORGANISM: Artificial sequence
<220> FEATURE:
<223> OTHER INFORMATION: An artificially synthesized primer for PCR

<400> SEQUENCE: 7
aatagcggcc gcaccatgag tgtgcccact cagg                                 34

<210> SEQ ID NO 8
<211> LENGTH: 18
<212> TYPE: DNA
<213> ORGANISM: Artificial sequence
<220> FEATURE:
<223> OTHER INFORMATION: An artificially synthesized primer for PCR

<400> SEQUENCE: 8
ttccagcttg gtccccccc                                                  18

<210> SEQ ID NO 9
<211> LENGTH: 20
<212> TYPE: DNA
<213> ORGANISM: Artificial sequence
<220> FEATURE:
<223> OTHER INFORMATION: An artificially synthesized primer sequence for
      RT-PCR

<400> SEQUENCE: 9
tatcgggctc ttctctgtgc                                                 20

<210> SEQ ID NO 10
<211> LENGTH: 20
<212> TYPE: DNA
<213> ORGANISM: Artificial sequence
<220> FEATURE:
<223> OTHER INFORMATION: An artificially synthesized primer sequence for
      RT-PCR
```

```
<400> SEQUENCE: 10
gactgggcag ggatctcata                                                  20

<210> SEQ ID NO 11
<211> LENGTH: 20
<212> TYPE: DNA
<213> ORGANISM: Artificial sequence
<220> FEATURE:
<223> OTHER INFORMATION: An artificially synthesized primer sequence for
      RT-PCR

<400> SEQUENCE: 11
ttagctgtgc tcgcgctact                                                  20

<210> SEQ ID NO 12
<211> LENGTH: 20
<212> TYPE: DNA
<213> ORGANISM: Artificial sequence
<220> FEATURE:
<223> OTHER INFORMATION: An artificially synthesized primer sequence for
      RT-PCR

<400> SEQUENCE: 12
tcacatggtt cacacggcag                                                  20

<210> SEQ ID NO 13
<211> LENGTH: 137
<212> TYPE: PRT
<213> ORGANISM: Mouse

<400> SEQUENCE: 13

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Asn Asp Thr Tyr Met His Trp Val Lys Gln Arg Pro Glu Gln Gly Leu
    50                  55                  60

Glu Trp Ile Gly Arg Ile Asp Pro Ala Asn Gly Asn Thr Lys Tyr Asp
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Arg Gly Ala Arg Gly Ser Arg Phe Ala Tyr Trp Gly
        115                 120                 125

Gln Gly Thr Leu Val Thr Val Ser Ala
    130                 135

<210> SEQ ID NO 14
<211> LENGTH: 411
<212> TYPE: DNA
<213> ORGANISM: Mouse

<400> SEQUENCE: 14
atgaaatgca gctgggttat cttcttcctg atggcagtgg ttacaggggt caattcagag    60
gttcagctgc agcagtctgg ggcagagctt gtgaagccag ggcctcagt caagttgtcc    120 tgcacagctt ctggcttcaa cattaacgac acctatatgc actgggtgaa gcagaggcct    180
```

```
gaacagggcc tggagtggat tggaaggatt gatcctgcga atggtaatac taaatatgac      240
ccgaagttcc agggcaaggc cactataaca gcagacacat cctccaacac agcctacctg      300
cagctcagca gcctgacatc tgaggacact gccgtctatt actgtgctag aggagcacgg      360
gggagtagat ttgcttactg gggccaaggg actctggtca ctgtctctgc a              411
```

```
<210> SEQ ID NO 15
<211> LENGTH: 7
<212> TYPE: PRT
<213> ORGANISM: Mouse

<400> SEQUENCE: 15

Ile Asn Asp Thr Tyr Met His
1               5

<210> SEQ ID NO 16
<211> LENGTH: 21
<212> TYPE: DNA
<213> ORGANISM: Mouse

<400> SEQUENCE: 16
attaacgaca cctatatgca c                                                21

<210> SEQ ID NO 17
<211> LENGTH: 12
<212> TYPE: PRT
<213> ORGANISM: Mouse

<400> SEQUENCE: 17

Arg Ile Asp Pro Ala Asn Gly Asn Thr Lys Tyr Asp
1               5                   10

<210> SEQ ID NO 18
<211> LENGTH: 36
<212> TYPE: DNA
<213> ORGANISM: Mouse

<400> SEQUENCE: 18
aggattgatc ctgcgaatgg taatactaaa tatgac                                36

<210> SEQ ID NO 19
<211> LENGTH: 6
<212> TYPE: PRT
<213> ORGANISM: Mouse

<400> SEQUENCE: 19

Gly Ser Arg Phe Ala Tyr
1               5

<210> SEQ ID NO 20
<211> LENGTH: 18
<212> TYPE: DNA
<213> ORGANISM: Mouse

<400> SEQUENCE: 20
gggagtagat ttgcttac                                                    18

<210> SEQ ID NO 21
<211> LENGTH: 124
<212> TYPE: PRT
<213> ORGANISM: Mouse

<400> SEQUENCE: 21
```

```
Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60

Gln Leu Leu Val Tyr Val Ala Thr Asn Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Ser Tyr Tyr Cys Gln His Phe Trp
            100                 105                 110

Gly Thr Pro Tyr Thr Phe Gly Gly Gly Thr Lys Leu
            115                 120
```

<210> SEQ ID NO 22
<211> LENGTH: 372
<212> TYPE: DNA
<213> ORGANISM: Mouse

<400> SEQUENCE: 22

```
atgagtgtgc ccactcaggt cctggggttg ctgctgctgt ggcttacaga tgccagatgt     60
gacatccaga tgactcagtc tccagcctcc ctatctgtat ctgtgggaga aactgtcacc    120
atcacatgtc gagcaagtga gaatatttac agtaatttag catggtatca gcagaaacag    180
ggaaaatctc ctcagctcct ggtctatgtt gcaacaaact tagcagatgg tgtgccatca    240
aggttcagtg gcagtggatc aggcacacag tattccctca agatcaacag cctgcagtct    300
gaagattttg ggagttatta ctgtcaacat ttttggggta ctccgtacac gttcggaggg    360
gggaccaagc tg                                                        372
```

<210> SEQ ID NO 23
<211> LENGTH: 11
<212> TYPE: PRT
<213> ORGANISM: Mouse

<400> SEQUENCE: 23

```
Arg Ala Ser Glu Asn Ile Tyr Ser Asn Leu Ala
1               5                   10
```

<210> SEQ ID NO 24
<211> LENGTH: 33
<212> TYPE: DNA
<213> ORGANISM: Mouse

<400> SEQUENCE: 24

```
cgagcaagtg agaatattta cagtaattta gca                                  33
```

<210> SEQ ID NO 25
<211> LENGTH: 7
<212> TYPE: PRT
<213> ORGANISM: Mouse

<400> SEQUENCE: 25

```
Val Ala Thr Asn Leu Ala Asp
1               5
```

<210> SEQ ID NO 26
<211> LENGTH: 27
<212> TYPE: DNA
<213> ORGANISM: Mouse

<400> SEQUENCE: 26
gtctatgttg caacaaactt agcagat					27

<210> SEQ ID NO 27
<211> LENGTH: 8
<212> TYPE: PRT
<213> ORGANISM: Mouse

<400> SEQUENCE: 27

Gln His Phe Trp Gly Thr Pro Tyr
1               5

<210> SEQ ID NO 28
<211> LENGTH: 24
<212> TYPE: DNA
<213> ORGANISM: Mouse

<400> SEQUENCE: 28
caacattttt ggggtactcc gtac					24

<210> SEQ ID NO 29
<211> LENGTH: 139
<212> TYPE: PRT
<213> ORGANISM: Mouse

<400> SEQUENCE: 29

Met Gly Trp Ser Arg Ile Phe Leu Phe Leu Leu Ser Ile Thr Ala Gly
1               5                   10                  15

Val His Cys Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Ala Phe
        35                  40                  45

Ser Ser Ser Trp Met Asn Trp Val Lys Gln Arg Pro Gly Gln Gly Leu
    50                  55                  60

Glu Trp Ile Gly Arg Ile Tyr Pro Gly Asp Gly Asp Thr Asn Tyr Asn
65                  70                  75                  80

Gly Lys Phe Lys Gly Lys Ala Thr Leu Thr Ala Asp Lys Ser Ser Ser
                85                  90                  95

Thr Ala Tyr Met Gln Leu Ser Ser Leu Thr Ser Val Asp Ser Ala Val
            100                 105                 110

Tyr Phe Cys Ala Arg Gly Gly Asn Tyr Gly Trp Phe Ala Tyr Trp Gly
        115                 120                 125

Gln Gly Thr Leu Val Thr Val Ser Ala Gly Ser
    130                 135

<210> SEQ ID NO 30
<211> LENGTH: 417
<212> TYPE: DNA
<213> ORGANISM: Mouse

<400> SEQUENCE: 30
atgggatgga gccggatctt tctcttcctc ctgtcaataa ctgcaggtgt ccattgccag     60
gtccagctgc agcagtctgg acctgagctg gtgaagcctg gggcctcagt gaagatttcc    120
tgcaaagctt ctggctacgc attcagtagc tcttggatga actgggtgaa gcagaggcct    180

```
ggacagggtc ttgagtggat tggacggatt tatcctggag atggagatac taactacaat      240
gggaagttca agggcaaggc cacactgact gcagacaaat cctccagcac agcctacatg      300
caactcagca gcctgacctc tgtggactct gcggtctatt tctgtgcaag agggggtaac      360
tacggctggt ttgcttactg gggccaaggg actctggtca ctgtctctgc aggatcc        417
```

<210> SEQ ID NO 31
<211> LENGTH: 5
<212> TYPE: PRT
<213> ORGANISM: Mouse

<400> SEQUENCE: 31

Ser Ser Trp Met Asn
1               5

<210> SEQ ID NO 32
<211> LENGTH: 18
<212> TYPE: DNA
<213> ORGANISM: Mouse

<400> SEQUENCE: 32
agtagctctt ggatgaac                                                    18

<210> SEQ ID NO 33
<211> LENGTH: 12
<212> TYPE: PRT
<213> ORGANISM: Mouse

<400> SEQUENCE: 33

Arg Ile Tyr Pro Gly Asp Gly Asp Thr Asn Tyr Asn
1               5                   10

<210> SEQ ID NO 34
<211> LENGTH: 36
<212> TYPE: DNA
<213> ORGANISM: Mouse

<400> SEQUENCE: 34
cggatttatc ctggagatgg agatactaac tacaat                                36

<210> SEQ ID NO 35
<211> LENGTH: 9
<212> TYPE: PRT
<213> ORGANISM: Mouse

<400> SEQUENCE: 35

Gly Gly Asn Tyr Gly Trp Phe Ala Tyr
1               5

<210> SEQ ID NO 36
<211> LENGTH: 27
<212> TYPE: DNA
<213> ORGANISM: Mouse

<400> SEQUENCE: 36
gggggtaact acggctggtt tgcttac                                          27

<210> SEQ ID NO 37
<211> LENGTH: 129
<212> TYPE: PRT
<213> ORGANISM: Mouse

<400> SEQUENCE: 37

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Arg Ala Ser Lys Ser
            35                  40                  45

Val Ser Thr Ser Gly Tyr Ser Tyr Met His Trp Tyr Gln Gln Lys Pro
        50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln His Ser Arg Glu Leu Tyr Thr Phe Gly Gly Gly Thr Lys Leu Gly
            115                 120                 125

Ser

<210> SEQ ID NO 38
<211> LENGTH: 456
<212> TYPE: DNA
<213> ORGANISM: Mouse

<400> SEQUENCE: 38
atggagacag acacactcct gttatgggta ctgctgctct ggttccagg ttccactggt      60 gacattgtgc tgacacagtc tcctgcttcc ttagctgtat ctctgggca gagggccacc    120 atctcatgca gggccagcaa aagtgtcagt acatctggct atagttatat gcactggtac    180
caacagaaac aggacagcc acccaaactc ctcatctatc ttgcatccaa cctagaatct    240
ggggtccctg ccaggttcag tggcagtggg tctgggacag acttcaccct caacatccat    300
cctgtggagg aggaggatgc tgcaacctat tactgtcagc acagtaggga gctgtacacg    360
ttcggagggg ggaccaagct ggatccgaa atcaaacgaa ctgtggctgc accatctgtc    420
ttcatcttcc cgccatctga tgagcagttg aaatct                              456

<210> SEQ ID NO 39
<211> LENGTH: 15
<212> TYPE: PRT
<213> ORGANISM: Mouse

<400> SEQUENCE: 39

Arg Ala Ser Lys Ser Val Ser Thr Ser Gly Tyr Ser Tyr Met His
1               5                   10                  15

<210> SEQ ID NO 40
<211> LENGTH: 45
<212> TYPE: DNA
<213> ORGANISM: Mouse

<400> SEQUENCE: 40
agggccagca aaagtgtcag tacatctggc tatagttata tgcac                     45

<210> SEQ ID NO 41
<211> LENGTH: 7
<212> TYPE: PRT
<213> ORGANISM: Mouse

<400> SEQUENCE: 41
```

```
Leu Ala Ser Asn Leu Glu Ser
1               5

<210> SEQ ID NO 42
<211> LENGTH: 21
<212> TYPE: DNA
<213> ORGANISM: Mouse

<400> SEQUENCE: 42
cttgcatcca acctagaatc t                                              21

<210> SEQ ID NO 43
<211> LENGTH: 7
<212> TYPE: PRT
<213> ORGANISM: Mouse

<400> SEQUENCE: 43

Gln His Ser Arg Glu Leu Tyr
1               5

<210> SEQ ID NO 44
<211> LENGTH: 21
<212> TYPE: DNA
<213> ORGANISM: Mouse

<400> SEQUENCE: 44
cagcacagta gggagctgta c                                              21

<210> SEQ ID NO 45
<211> LENGTH: 1404
<212> TYPE: DNA
<213> ORGANISM: Artificial sequence
<220> FEATURE:
<223> OTHER INFORMATION: A chemically synthesized sequence of H chain of
      anti-REG4 chimeric antibody with signal sequence.

<400> SEQUENCE: 45
atgaaatgca gctgggttat cttcttcctg atggcagtgg ttacaggggt caattcagag      60
gttcagctgc agcagtctgg ggcagagctt gtgaagccag ggcctcagt caagttgtcc     120 tgcacagctt ctggcttcaa cattaacgac acctatatgc actgggtgaa gcagaggcct    180
gaacagggcc tggagtggat tggaaggatt gatcctgcga atggtaatac taaatatgac    240
ccgaagttcc agggcaaggc cactataaca gcagacacat cctccaacac agcctacctg    300
cagctcagca gcctgacatc tgaggacact gccgtctatt actgtgctag gagcacgg     360 gggagtagat ttgcttactg gggccaaggg actctggtca ctgtctctgc agctagcacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc cggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720 gacaaaactc acacatgccc accgtgccca gcacctgaac tcctgggggg accgtcagtc    780
ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
```

```
tgcaaggtct ccaacaaagc cctcccagcc cccatcgaga aaaccatctc caaagccaaa       1080
gggcagcccc gagaaccaca ggtgtacacc ctgcccccat cccgggatga gctgaccaag       1140
aaccaggtca gcctgacctg cctggtcaaa ggcttctatc ccagcgacat cgccgtggag       1200
tgggagagca atgggcagcc ggagaacaac tacaagacca cgcctcccgt gctggactcc       1260
gacggctcct tcttcctcta tagcaagctc accgtggaca agagcaggtg gcagcagggg       1320
aacgtcttct catgctccgt gatgcatgag gctctgcaca accactacac gcagaagagc       1380
ctctccctgt ccccgggtaa atga                                              1404
```

<210> SEQ ID NO 46
<211> LENGTH: 467
<212> TYPE: PRT
<213> ORGANISM: Artificial sequence
<220> FEATURE:
<223> OTHER INFORMATION: A chemically synthesized sequence of H chain of anti-REG4 chimeric antibody with signal sequence.

<400> SEQUENCE: 46

```
Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Asn Asp Thr Tyr Met His Trp Val Lys Gln Arg Pro Glu Gln Gly Leu
    50                  55                  60

Glu Trp Ile Gly Arg Ile Asp Pro Ala Asn Gly Asn Thr Lys Tyr Asp
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Arg Gly Ala Arg Gly Ser Arg Phe Ala Tyr Trp Gly
        115                 120                 125

Gln Gly Thr Leu Val Thr Val Ser Ala Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285
```

```
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 47
<211> LENGTH: 705
<212> TYPE: DNA
<213> ORGANISM: Artificial sequence
<220> FEATURE:
<223> OTHER INFORMATION: A chemically synthesized sequence of L chain of
      anti-REG4 chimeric antibody with signal sequence.

<400> SEQUENCE: 47
atgagtgtgc ccactcaggt cctggggttg ctgctgctgt ggcttacaga tgccagatgt      60
gacatccaga tgactcagtc tccagcctcc ctatctgtat ctgtgggaga aactgtcacc     120
atcacatgtc gagcaagtga gaatatttac agtaatttag catggtatca gcagaaacag     180
ggaaaatctc ctcagctcct ggtctatgtt gcaacaaact tagcagatgg tgtgccatca     240
aggttcagtg gcagtggatc aggcacacag tattccctca agatcaacag cctgcagtct     300
gaagattttg ggagttatta ctgtcaacat ttttggggta ctccgtacac gttcggaggg     360
gggaccaagc tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgaca     600
ctgagcaaag cagactacga gaaacacaaa gtctacgcct gcgaagtcac ccatcagggc     660
ctgagctcgc ccgtcacaaa gagcttcaac aggggagagt gttag                    705

<210> SEQ ID NO 48
<211> LENGTH: 234
<212> TYPE: PRT
<213> ORGANISM: Artificial sequence
<220> FEATURE:
<223> OTHER INFORMATION: A chemically synthesized sequence of L chain of
```

-continued anti-REG4 chimeric antibody with signal sequence.

<400> SEQUENCE: 48

```
Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60

Gln Leu Leu Val Tyr Val Ala Thr Asn Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Ser Tyr Tyr Cys Gln His Phe Trp
            100                 105                 110

Gly Thr Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 49
<211> LENGTH: 1398
<212> TYPE: DNA
<213> ORGANISM: Artificial sequence
<220> FEATURE:
<223> OTHER INFORMATION: A chemically synthesized sequence of H chain of anti-REG4 chimeric antibody with signal sequence.

<400> SEQUENCE: 49

```
atgggatgga gccggatctt tctcttcctc ctgtcaataa ctgcaggtgt ccattgccag    60
gtccagctgc agcagtctgg acctgagctg gtgaagcctg ggccttcagt gaagatttcc   120
tgcaaagctt ctggctacgc attcagtagc tcttggatga actgggtgaa gcagaggcct   180
ggacagggtc ttgagtggat tggacggatt tatcctggag atggagatac taactacaat   240
gggaagttca aggcaaggc cacactgact gcagacaaat cctccagcac agcctacatg   300
caactcagca gcctgacctc tgtggactct gcggtctatt tctgtgcaag agggggtaac   360
tacggctggt ttgcttactg gggccaaggg actctggtca ctgtctctgc aggatccgcc   420
tccaccaagg gcccatcggt cttccccctg gcgccctgct ccaggagcac ctccgagagc   480
acagcggccc tgggctgcct ggtcaaggac tacttccccg aaccggtgac ggtgtcgtgg   540
aactcaggcg ctctgaccag cggcgtgcac accttcccgg ctgtcctaca gtcctcagga   600
```

```
ctctactccc tcagcagcgt ggtgaccgtg ccctccagca acttcggcac ccagacctac    660
acctgcaacg taaatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa acccaagga caccctcatg atctcccgga ccctgaggt cacgtgcgtg     840 gtggtggacg tgagccacga agaccccgag gtccagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca agccctccc agcccccatc gagaaaacca tctccaaagc caagggcag    1080 ccccgagaac cacaggtgta caccctgccc ccatcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatga                                                  1398
```

<210> SEQ ID NO 50
<211> LENGTH: 465
<212> TYPE: PRT
<213> ORGANISM: Artificial sequence
<220> FEATURE:
<223> OTHER INFORMATION: A chemically synthesized sequence of H chain of anti-REG4 chimeric antibody with signal sequence.

<400> SEQUENCE: 50

```
Met Gly Trp Ser Arg Ile Phe Leu Phe Leu Leu Ser Ile Thr Ala Gly
1               5                   10                  15

Val His Cys Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Ala Phe
        35                  40                  45

Ser Ser Ser Trp Met Asn Trp Val Lys Gln Arg Pro Gly Gln Gly Leu
    50                  55                  60

Glu Trp Ile Gly Arg Ile Tyr Pro Gly Asp Gly Asp Thr Asn Tyr Asn
65                  70                  75                  80

Gly Lys Phe Lys Gly Lys Ala Thr Leu Thr Ala Asp Lys Ser Ser Ser
                85                  90                  95

Thr Ala Tyr Met Gln Leu Ser Ser Leu Thr Ser Val Asp Ser Ala Val
            100                 105                 110

Tyr Phe Cys Ala Arg Gly Gly Asn Tyr Gly Trp Phe Ala Tyr Trp Gly
        115                 120                 125

Gln Gly Thr Leu Val Thr Val Ser Ala Gly Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205
```

```
Thr Val Pro Ser Ser Asn Phe Gly Thr Gln Thr Tyr Thr Cys Asn Val
    210             215                 220
Asn His Lys Pro Ser Asn Thr Lys Val Asp Lys Thr Val Glu Arg Lys
225             230                 235                 240
Cys Cys Val Glu Cys Pro Pro Cys Pro Ala Pro Val Ala Gly Pro
            245                 250                 255
Ser Val Phe Leu Phe Pro Pro Lys Pro Lys Asp Thr Leu Met Ile Ser
            260                 265                 270
Arg Thr Pro Glu Val Thr Cys Val Val Asp Val Ser His Glu Asp
            275                 280                 285
Pro Glu Val Gln Phe Asn Trp Tyr Val Asp Gly Val Glu Val His Asn
290                 295                 300
Ala Lys Thr Lys Pro Arg Glu Glu Gln Tyr Asn Ser Thr Tyr Arg Val
305             310                 315                 320
Val Ser Val Leu Thr Val Leu His Gln Asp Trp Leu Asn Gly Lys Glu
                325                 330                 335
Tyr Lys Cys Lys Val Ser Asn Lys Ala Leu Pro Ala Pro Ile Glu Lys
            340                 345                 350
Thr Ile Ser Lys Ala Lys Gly Gln Pro Arg Glu Pro Gln Val Tyr Thr
    355                 360                 365
Leu Pro Pro Ser Arg Asp Glu Leu Thr Lys Asn Gln Val Ser Leu Thr
370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
    435                 440                 445
Ala Leu His Asn His Tyr Thr Gln Lys Ser Leu Ser Leu Ser Pro Gly
    450                 455                 460
Lys
465

<210> SEQ ID NO 51
<211> LENGTH: 720
<212> TYPE: DNA
<213> ORGANISM: Artificial sequence
<220> FEATURE:
<223> OTHER INFORMATION: A chemically synthesized sequence of L chain of
      anti-REG4 chimeric antibody with signal sequence.

<400> SEQUENCE: 51
atggagacag acacactcct gttatgggta ctgctgctct gggttccagg ttccactggt      60
gacattgtgc tgacacagtc tcctgcttcc ttagctgtat ctctgggca gagggccacc    120 atctcatgca gggccagcaa aagtgtcagt acatctggct atagttatat gcactggtac    180
caacagaaac caggacagcc acccaaactc ctcatctatc ttgcatccaa cctagaatct    240
ggggtccctg ccaggttcag tggcagtggg tctgggacag acttcaccct caacatccat    300
cctgtggagg aggaggatgc tgcaacctat tactgtcagc acagtaggga gctgtacacg    360
ttcggagggg ggaccaagct ggatccgaa atcaaacgaa ctgtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
```
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgttag    720

<210> SEQ ID NO 52
<211> LENGTH: 239
<212> TYPE: PRT
<213> ORGANISM: Artificial sequence
<220> FEATURE:
<223> OTHER INFORMATION: A chemically synthesized sequence of L chain of
      anti-REG4 chimeric antibody with signal sequence.

<400> SEQUENCE: 52

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Gly Tyr Ser Tyr Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ser Arg Glu Leu Tyr Thr Phe Gly Gly Gly Thr Lys Leu Gly
        115                 120                 125

Ser Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 53
<211> LENGTH: 36
<212> TYPE: DNA
<213> ORGANISM: Artificial sequence
<220> FEATURE:
<223> OTHER INFORMATION: An artificially synthesized primer for PCR

<400> SEQUENCE: 53
aatagcggcc gcaccatggg atggagccgg atctttt                              36

<210> SEQ ID NO 54
<211> LENGTH: 36
<212> TYPE: DNA

```
<213> ORGANISM: Artificial sequence
<220> FEATURE:
<223> OTHER INFORMATION: An artificially synthesized primer for PCR

<400> SEQUENCE: 54
aataggatcc tgcagagaca gtgaccagag tccctt                                    36

<210> SEQ ID NO 55
<211> LENGTH: 35
<212> TYPE: DNA
<213> ORGANISM: Artificial sequence
<220> FEATURE:
<223> OTHER INFORMATION: An artificially synthesized primer for PCR

<400> SEQUENCE: 55
aatagcggcc gcaccatgga gacagacaca ctcct                                     35

<210> SEQ ID NO 56
<211> LENGTH: 34
<212> TYPE: DNA
<213> ORGANISM: Artificial sequence
<220> FEATURE:
<223> OTHER INFORMATION: An artificially synthesized primer for PCR

<400> SEQUENCE: 56
aataggatcc cagcttggtc cccctccga acgt                                       34

<210> SEQ ID NO 57
<211> LENGTH: 1404
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1404)

<400> SEQUENCE: 57 atg aaa tgc agc tgg gtt atc ttc ttc ctg atg gca gtg gtt aca ggg        48
Met Lys Cys Ser Trp Val Ile Phe Phe Leu Met Ala Val Val Thr Gly
1               5                  10                  15 gtc aat tca gag gtt cag ctg cag cag tct ggg gca gag ctt gtg aag        96
Val Asn Ser Glu Val Gln Leu Gln Gln Ser Gly Ala Glu Leu Val Lys
            20                  25                  30 cca ggg gcc tca gtc aag ttg tcc tgc aca gct tct ggc ttc aac att       144
Pro Gly Ala Ser Val Lys Leu Ser Cys Thr Ala Ser Gly Phe Asn Ile
        35                  40                  45 aac gac acc tat atg cac tgg gtg aag cag agg cct gaa cag ggc ctg       192
Asn Asp Thr Tyr Met His Trp Val Lys Gln Arg Pro Glu Gln Gly Leu
    50                  55                  60 gag tgg att gga agg att gat cct gcg aat ggt aat act aaa tat gac       240
Glu Trp Ile Gly Arg Ile Asp Pro Ala Asn Gly Asn Thr Lys Tyr Asp
65                  70                  75                  80 ccg aag ttc cag ggc aag gcc act ata aca gca gac aca tcc tcc aac       288
Pro Lys Phe Gln Gly Lys Ala Thr Ile Thr Ala Asp Thr Ser Ser Asn
                85                  90                  95 aca gcc tac ctg cag ctc agc agc ctg aca tct gag gac act gcc gtc       336
Thr Ala Tyr Leu Gln Leu Ser Ser Leu Thr Ser Glu Asp Thr Ala Val
            100                 105                 110 tat tac tgt gct aga gga gca cgg ggg agt aga ttt gct tac tgg ggc       384
Tyr Tyr Cys Ala Arg Gly Ala Arg Gly Ser Arg Phe Ala Tyr Trp Gly
        115                 120                 125 caa ggg act ctg gtc act gtc tct gca gcc aaa aca aca gcc cca tcg       432
Gln Gly Thr Leu Val Thr Val Ser Ala Ala Lys Thr Thr Ala Pro Ser
```

```
            130                 135                 140
gtc tat cca ctg gcc cct gtg tgt gga gat aca act ggc tcc tcg gtg        480
Val Tyr Pro Leu Ala Pro Val Cys Gly Asp Thr Thr Gly Ser Ser Val
145                 150                 155                 160 act cta gga tgc ctg gtc aag ggt tat ttc cct gag cca gtg acc ttg        528
Thr Leu Gly Cys Leu Val Lys Gly Tyr Phe Pro Glu Pro Val Thr Leu
                165                 170                 175 acc tgg aac tct gga tcc ctg tcc agt ggt gtg cac acc ttc cca gct        576
Thr Trp Asn Ser Gly Ser Leu Ser Ser Gly Val His Thr Phe Pro Ala
        180                 185                 190 gtc ctg cag tct gac ctc tac acc ctc agc agc tca gtg act gta acc        624
Val Leu Gln Ser Asp Leu Tyr Thr Leu Ser Ser Ser Val Thr Val Thr
    195                 200                 205 tcg agc acc tgg ccc agc cag tcc atc acc tgc aat gtg gcc cac ccg        672
Ser Ser Thr Trp Pro Ser Gln Ser Ile Thr Cys Asn Val Ala His Pro
210                 215                 220 gca agc agc acc aag gtg gac aag aaa att gag ccc aga ggg ccc aca        720
Ala Ser Ser Thr Lys Val Asp Lys Lys Ile Glu Pro Arg Gly Pro Thr
225                 230                 235                 240 atc aag ccc tgt cct cca tgc aaa tgc cca gca cct aac ctc ttg ggt        768
Ile Lys Pro Cys Pro Pro Cys Lys Cys Pro Ala Pro Asn Leu Leu Gly
                245                 250                 255 gga cca tcc gtc ttc atc ttc cct cca aag atc aag gat gta ctc atg        816
Gly Pro Ser Val Phe Ile Phe Pro Pro Lys Ile Lys Asp Val Leu Met
        260                 265                 270 atc tcc ctg agc ccc ata gtc aca tgt gtg gtg gtg gat gtg agc gag        864
Ile Ser Leu Ser Pro Ile Val Thr Cys Val Val Val Asp Val Ser Glu
    275                 280                 285 gat gac cca gat gtc cag atc agc tgg ttt gtg aac aac gtg gaa gta        912
Asp Asp Pro Asp Val Gln Ile Ser Trp Phe Val Asn Asn Val Glu Val
290                 295                 300 cac aca gct cag aca caa acc cat aga gag gat tac aac agt act ctc        960
His Thr Ala Gln Thr Gln Thr His Arg Glu Asp Tyr Asn Ser Thr Leu
305                 310                 315                 320 cgg gtg gtc agt gcc ctc ccc atc cag cac cag gac tgg atg agt ggc       1008
Arg Val Val Ser Ala Leu Pro Ile Gln His Gln Asp Trp Met Ser Gly
                325                 330                 335 aag gag ttc aaa tgc aag gtc aac aac aaa gac ctc cca gcg ccc atc       1056
Lys Glu Phe Lys Cys Lys Val Asn Asn Lys Asp Leu Pro Ala Pro Ile
        340                 345                 350 gag aga acc atc tca aaa ccc aaa ggg tca gta aga gct cca cag gta       1104
Glu Arg Thr Ile Ser Lys Pro Lys Gly Ser Val Arg Ala Pro Gln Val
    355                 360                 365 tat gtc ttg cct cca cca gaa gaa gag atg act aag aaa cag gtc act       1152
Tyr Val Leu Pro Pro Pro Glu Glu Glu Met Thr Lys Lys Gln Val Thr
370                 375                 380 ctg acc tgc atg gtc aca gac ttc atg cct gaa gac att tac gtg gag       1200
Leu Thr Cys Met Val Thr Asp Phe Met Pro Glu Asp Ile Tyr Val Glu
385                 390                 395                 400 tgg acc aac aac ggg aaa aca gag cta aac tac aag aac act gaa cca       1248
Trp Thr Asn Asn Gly Lys Thr Glu Leu Asn Tyr Lys Asn Thr Glu Pro
                405                 410                 415 gtc ctg gac tct gat ggt tct tac ttc atg tac agc aag ctg aga gtg       1296
Val Leu Asp Ser Asp Gly Ser Tyr Phe Met Tyr Ser Lys Leu Arg Val
        420                 425                 430 gaa aag aag aac tgg gtg gaa aga aat agc tac tcc tgt tca gtg gtc       1344
Glu Lys Lys Asn Trp Val Glu Arg Asn Ser Tyr Ser Cys Ser Val Val
    435                 440                 445 cac gag ggt ctg cac aat cac cac acg act aag agc ttc tcc cgg act       1392
```

```
His Glu Gly Leu His Asn His His Thr Thr Lys Ser Phe Ser Arg Thr
    450                 455                 460 ccg ggt aaa tga                                                    1404
Pro Gly Lys
465
```

<210> SEQ ID NO 58
<211> LENGTH: 467
<212> TYPE: PRT
<213> ORGANISM: Artificial sequence
<220> FEATURE:
<223> OTHER INFORMATION: Synthetic polypeptide: 92-13 H chain

<400> SEQUENCE: 58

```
Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Asn Asp Thr Tyr Met His Trp Val Lys Gln Arg Pro Glu Gln Gly Leu
    50                  55                  60

Glu Trp Ile Gly Arg Ile Asp Pro Ala Asn Gly Asn Thr Lys Tyr Asp
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Arg Gly Ala Arg Gly Ser Arg Phe Ala Tyr Trp Gly
        115                 120                 125

Gln Gly Thr Leu Val Thr Val Ser Ala Ala Lys Thr Thr Ala Pro Ser
    130                 135                 140

Val Tyr Pro Leu Ala Pro Val Cys Gly Asp Thr Thr Gly Ser Ser Val
145                 150                 155                 160

Thr Leu Gly Cys Leu Val Lys Gly Tyr Phe Pro Glu Pro Val Thr Leu
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Thr
        195                 200                 205

Ser Ser Thr Trp Pro Ser Gln Ser Ile Thr Cys Asn Val Ala His Pro
    210                 215                 220

Ala Ser Ser Thr Lys Val Asp Lys Lys Ile Glu Pro Arg Gly Pro Thr
225                 230                 235                 240

Ile Lys Pro Cys Pro Pro Cys Lys Cys Pro Ala Pro Asn Leu Leu Gly
                245                 250                 255

Gly Pro Ser Val Phe Ile Phe Pro Pro Lys Ile Lys Asp Val Leu Met
            260                 265                 270

Ile Ser Leu Ser Pro Ile Val Thr Cys Val Val Val Asp Val Ser Glu
        275                 280                 285

Asp Asp Pro Asp Val Gln Ile Ser Trp Phe Val Asn Asn Val Glu Val
    290                 295                 300

His Thr Ala Gln Thr Gln Thr His Arg Glu Asp Tyr Asn Ser Thr Leu
305                 310                 315                 320

Arg Val Val Ser Ala Leu Pro Ile Gln His Gln Asp Trp Met Ser Gly
                325                 330                 335
```

```
Lys Glu Phe Lys Cys Lys Val Asn Asn Lys Asp Leu Pro Ala Pro Ile
            340                 345                 350

Glu Arg Thr Ile Ser Lys Pro Lys Gly Ser Val Arg Ala Pro Gln Val
            355                 360                 365

Tyr Val Leu Pro Pro Glu Glu Met Thr Lys Lys Gln Val Thr
    370                 375                 380

Leu Thr Cys Met Val Thr Asp Phe Met Pro Glu Asp Ile Tyr Val Glu
385                 390                 395                 400

Trp Thr Asn Asn Gly Lys Thr Glu Leu Asn Tyr Lys Asn Thr Glu Pro
                405                 410                 415

Val Leu Asp Ser Asp Gly Ser Tyr Phe Met Tyr Ser Lys Leu Arg Val
            420                 425                 430

Glu Lys Lys Asn Trp Val Glu Arg Asn Ser Tyr Ser Cys Ser Val Val
            435                 440                 445

His Glu Gly Leu His Asn His His Thr Thr Lys Ser Phe Ser Arg Thr
            450                 455                 460

Pro Gly Lys
465

<210> SEQ ID NO 59
<211> LENGTH: 705
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(705)

<400> SEQUENCE: 59 atg agt gtg ccc act cag gtc ctg ggg ttg ctg ctg ctg tgg ctt aca       48
Met Ser Val Pro Thr Gln Val Leu Gly Leu Leu Leu Leu Trp Leu Thr
1               5                   10                  15 gat gcc aga tgt gac atc cag atg act cag tct cca gcc tcc cta tct       96
Asp Ala Arg Cys Asp Ile Gln Met Thr Gln Ser Pro Ala Ser Leu Ser
                20                  25                  30 gta tct gtg gga gaa act gtc acc atc aca tgt cga gca agt gag aat      144
Val Ser Val Gly Glu Thr Val Thr Ile Thr Cys Arg Ala Ser Glu Asn
            35                  40                  45 att tac agt aat tta gca tgg tat cag cag aaa cag gga aaa tct cct      192
Ile Tyr Ser Asn Leu Ala Trp Tyr Gln Gln Lys Gln Gly Lys Ser Pro
        50                  55                  60 cag ctc ctg gtc tat gtt gca aca aac tta gca gat ggt gtg cca tca      240
Gln Leu Leu Val Tyr Val Ala Thr Asn Leu Ala Asp Gly Val Pro Ser
65                  70                  75                  80 agg ttc agt ggc agt gga tca ggc aca cag tat tcc ctc aag atc aac      288
Arg Phe Ser Gly Ser Gly Ser Gly Thr Gln Tyr Ser Leu Lys Ile Asn
                85                  90                  95 agc ctg cag tct gaa gat ttt ggg agt tat tac tgt caa cat ttt tgg      336
Ser Leu Gln Ser Glu Asp Phe Gly Ser Tyr Tyr Cys Gln His Phe Trp
            100                 105                 110 ggt act ccg tac acg ttc gga ggg ggg acc aag ctg gaa ata aaa cgg      384
Gly Thr Pro Tyr Thr Phe Gly Gly Gly Thr Lys Leu Glu Ile Lys Arg
        115                 120                 125 gct gat gct gca cca act gta tcc atc ttc cca cca tcc agt gag cag      432
Ala Asp Ala Ala Pro Thr Val Ser Ile Phe Pro Pro Ser Ser Glu Gln
    130                 135                 140 tta aca tct gga ggt gcc tca gtc gtg tgc ttc ttg aac aac ttc tac      480
Leu Thr Ser Gly Gly Ala Ser Val Val Cys Phe Leu Asn Asn Phe Tyr
```

```
                145                 150                 155                 160
ccc aaa gac atc aat gtc aag tgg aag att gat ggc agt gaa cga caa        528
Pro Lys Asp Ile Asn Val Lys Trp Lys Ile Asp Gly Ser Glu Arg Gln
                165                 170                 175 aat ggc gtc ctg aac agt tgg act gat cag gac agc aaa gac agc acc        576
Asn Gly Val Leu Asn Ser Trp Thr Asp Gln Asp Ser Lys Asp Ser Thr
            180                 185                 190 tac agc atg agc agc acc ctc acg ttg acc aag gac gag tat gaa cga        624
Tyr Ser Met Ser Ser Thr Leu Thr Leu Thr Lys Asp Glu Tyr Glu Arg
        195                 200                 205 cat aac agc tat acc tgt gag gcc act cac aag aca tca act tca ccc        672
His Asn Ser Tyr Thr Cys Glu Ala Thr His Lys Thr Ser Thr Ser Pro
    210                 215                 220 att gtc aag agc ttc aac agg aat gag tgt tag                            705
Ile Val Lys Ser Phe Asn Arg Asn Glu Cys
225                 230
```

<210> SEQ ID NO 60
<211> LENGTH: 234
<212> TYPE: PRT
<213> ORGANISM: Artificial sequence
<220> FEATURE:
<223> OTHER INFORMATION: Synthetic polypeptide: 92-13 L chain

<400> SEQUENCE: 60

```
Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60

Gln Leu Leu Val Tyr Val Ala Thr Asn Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Ser Tyr Tyr Cys Gln His Phe Trp
            100                 105                 110

Gly Thr Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 61

<211> LENGTH: 1404
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1404)

<400> SEQUENCE: 61

```
atg gga tgg agc cgg atc ttt ctc ttc ctc ctg tca ata act gca ggt      48
Met Gly Trp Ser Arg Ile Phe Leu Phe Leu Leu Ser Ile Thr Ala Gly
1               5                   10                  15 gtc cat tgc cag gtc cag ctg cag cag tct gga cct gag ctg gtg aag      96
Val His Cys Gln Val Gln Leu Gln Gln Ser Gly Pro Glu Leu Val Lys
            20                  25                  30 cct ggg gcc tca gtg aag att tcc tgc aaa gct tct ggc tac gca ttc     144
Pro Gly Ala Ser Val Lys Ile Ser Cys Lys Ala Ser Gly Tyr Ala Phe
        35                  40                  45 agt agc tct tgg atg aac tgg gtg aag cag agg cct gga cag ggt ctt     192
Ser Ser Ser Trp Met Asn Trp Val Lys Gln Arg Pro Gly Gln Gly Leu
    50                  55                  60 gag tgg att gga cgg att tat cct gga gat gga gat act aac tac aat     240
Glu Trp Ile Gly Arg Ile Tyr Pro Gly Asp Gly Asp Thr Asn Tyr Asn
65                  70                  75                  80 ggg aag ttc aag ggc aag gcc aca ctg act gca gac aaa tcc tcc agc     288
Gly Lys Phe Lys Gly Lys Ala Thr Leu Thr Ala Asp Lys Ser Ser Ser
                85                  90                  95 aca gcc tac atg caa ctc agc agc ctg acc tct gtg gac tct gcg gtc     336
Thr Ala Tyr Met Gln Leu Ser Ser Leu Thr Ser Val Asp Ser Ala Val
            100                 105                 110 tat ttc tgt gca aga ggg ggt aac tac ggc tgg ttt gct tac tgg ggc     384
Tyr Phe Cys Ala Arg Gly Gly Asn Tyr Gly Trp Phe Ala Tyr Trp Gly
        115                 120                 125 caa ggg act ctg gtc act gtc tct gca gcc aaa aca aca gcc cca tcg     432
Gln Gly Thr Leu Val Thr Val Ser Ala Ala Lys Thr Thr Ala Pro Ser
    130                 135                 140 gtc tat cca ctg gcc cct gtg tgt gga gat aca act ggc tcc tcg gtg     480
Val Tyr Pro Leu Ala Pro Val Cys Gly Asp Thr Thr Gly Ser Ser Val
145                 150                 155                 160 act cta gga tgc ctg gtc aag ggt tat ttc cct gag cca gtg acc ttg     528
Thr Leu Gly Cys Leu Val Lys Gly Tyr Phe Pro Glu Pro Val Thr Leu
                165                 170                 175 acc tgg aac tct gga tcc ctg tcc agt ggt gtg cac acc ttc cca gct     576
Thr Trp Asn Ser Gly Ser Leu Ser Ser Gly Val His Thr Phe Pro Ala
            180                 185                 190 gtc ctg cag tct gac ctc tac acc ctc agc agc tca gtg act gta acc     624
Val Leu Gln Ser Asp Leu Tyr Thr Leu Ser Ser Ser Val Thr Val Thr
        195                 200                 205 tcg agc acc tgg ccc agc cag tcc atc acc tgc aat gtg gcc cac ccg     672
Ser Ser Thr Trp Pro Ser Gln Ser Ile Thr Cys Asn Val Ala His Pro
    210                 215                 220 gca agc agc acc aag gtg gac aag aaa att gag ccc aga ggg ccc aca     720
Ala Ser Ser Thr Lys Val Asp Lys Lys Ile Glu Pro Arg Gly Pro Thr
225                 230                 235                 240 atc aag ccc tgt cct cca tgc aaa tgc cca gca cct aac ctc ttg ggt     768
Ile Lys Pro Cys Pro Pro Cys Lys Cys Pro Ala Pro Asn Leu Leu Gly
                245                 250                 255 gga cca tcc gtc ttc atc ttc cct cca aag atc aag gat gta ctc atg     816
Gly Pro Ser Val Phe Ile Phe Pro Pro Lys Ile Lys Asp Val Leu Met
            260                 265                 270
```

```
atc tcc ctg agc ccc ata gtc aca tgt gtg gtg gtg gat gtg agc gag    864
Ile Ser Leu Ser Pro Ile Val Thr Cys Val Val Val Asp Val Ser Glu
        275                 280                 285 gat gac cca gat gtc cag atc agc tgg ttt gtg aac aac gtg gaa gta    912
Asp Asp Pro Asp Val Gln Ile Ser Trp Phe Val Asn Asn Val Glu Val
290                 295                 300 cac aca gct cag aca caa acc cat aga gag gat tac aac agt act ctc    960
His Thr Ala Gln Thr Gln Thr His Arg Glu Asp Tyr Asn Ser Thr Leu
305                 310                 315                 320 cgg gtg gtc agt gcc ctc ccc atc cag cac cag gac tgg atg agt ggc   1008
Arg Val Val Ser Ala Leu Pro Ile Gln His Gln Asp Trp Met Ser Gly
            325                 330                 335 aag gag ttc aaa tgc aag gtc aac aac aaa gac ctc cca gcg ccc atc   1056
Lys Glu Phe Lys Cys Lys Val Asn Asn Lys Asp Leu Pro Ala Pro Ile
        340                 345                 350 gag aga acc atc tca aaa ccc aaa ggg tca gta aga gct cca cag gta   1104
Glu Arg Thr Ile Ser Lys Pro Lys Gly Ser Val Arg Ala Pro Gln Val
    355                 360                 365 tat gtc ttg cct cca cca gaa gaa gag atg act aag aaa cag gtc act   1152
Tyr Val Leu Pro Pro Pro Glu Glu Glu Met Thr Lys Lys Gln Val Thr
370                 375                 380 ctg acc tgc atg gtc aca gac ttc atg cct gaa gac att tac gtg gag   1200
Leu Thr Cys Met Val Thr Asp Phe Met Pro Glu Asp Ile Tyr Val Glu
385                 390                 395                 400 tgg acc aac aac ggg aaa aca gag cta aac tac aag aac act gaa cca   1248
Trp Thr Asn Asn Gly Lys Thr Glu Leu Asn Tyr Lys Asn Thr Glu Pro
            405                 410                 415 gtc ctg gac tct gat ggt tct tac ttc atg tac agc aag ctg aga gtg   1296
Val Leu Asp Ser Asp Gly Ser Tyr Phe Met Tyr Ser Lys Leu Arg Val
        420                 425                 430 gaa aag aag aac tgg gtg gaa aga aat agc tac tcc tgt tca gtg gtc   1344
Glu Lys Lys Asn Trp Val Glu Arg Asn Ser Tyr Ser Cys Ser Val Val
    435                 440                 445 cac gag ggt ctg cac aat cac cac acg act aag agc ttc tcc cgg act   1392
His Glu Gly Leu His Asn His His Thr Thr Lys Ser Phe Ser Arg Thr
450                 455                 460 ccg ggt aaa tga                                                    1404
Pro Gly Lys
465

<210> SEQ ID NO 62
<211> LENGTH: 467
<212> TYPE: PRT
<213> ORGANISM: Artificial sequence
<220> FEATURE:
<223> OTHER INFORMATION: Synthetic polypeptide: 93-22 H chain

<400> SEQUENCE: 62

Met Gly Trp Ser Arg Ile Phe Leu Phe Leu Leu Ser Ile Thr Ala Gly
1               5                   10                  15

Val His Cys Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Ala Phe
        35                  40                  45

Ser Ser Ser Trp Met Asn Trp Val Lys Gln Arg Pro Gly Gln Gly Leu
    50                  55                  60

Glu Trp Ile Gly Arg Ile Tyr Pro Gly Asp Gly Asp Thr Asn Tyr Asn
65                  70                  75                  80

Gly Lys Phe Lys Gly Lys Ala Thr Leu Thr Ala Asp Lys Ser Ser Ser
                85                  90                  95
```

```
Thr Ala Tyr Met Gln Leu Ser Ser Leu Thr Ser Val Asp Ser Ala Val
            100                 105                 110

Tyr Phe Cys Ala Arg Gly Gly Asn Tyr Gly Trp Phe Ala Tyr Trp Gly
        115                 120                 125

Gln Gly Thr Leu Val Thr Val Ser Ala Ala Lys Thr Thr Ala Pro Ser
130                 135                 140

Val Tyr Pro Leu Ala Pro Val Cys Gly Asp Thr Thr Gly Ser Ser Val
145                 150                 155                 160

Thr Leu Gly Cys Leu Val Lys Gly Tyr Phe Pro Glu Pro Val Thr Leu
                165                 170                 175

Thr Trp Asn Ser Gly Ser Leu Ser Gly Val His Thr Phe Pro Ala
            180                 185                 190

Val Leu Gln Ser Asp Leu Tyr Thr Leu Ser Ser Val Thr Val Thr
                195                 200                 205

Ser Ser Thr Trp Pro Ser Gln Ser Ile Thr Cys Asn Val Ala His Pro
            210                 215                 220

Ala Ser Ser Thr Lys Val Asp Lys Lys Ile Glu Pro Arg Gly Pro Thr
225                 230                 235                 240

Ile Lys Pro Cys Pro Pro Cys Lys Cys Pro Ala Pro Asn Leu Leu Gly
                245                 250                 255

Gly Pro Ser Val Phe Ile Phe Pro Pro Lys Ile Lys Asp Val Leu Met
                260                 265                 270

Ile Ser Leu Ser Pro Ile Val Thr Cys Val Val Val Asp Val Ser Glu
            275                 280                 285

Asp Asp Pro Asp Val Gln Ile Ser Trp Phe Val Asn Asn Val Glu Val
290                 295                 300

His Thr Ala Gln Thr Gln Thr His Arg Glu Asp Tyr Asn Ser Thr Leu
305                 310                 315                 320

Arg Val Val Ser Ala Leu Pro Ile Gln His Gln Asp Trp Met Ser Gly
                325                 330                 335

Lys Glu Phe Lys Cys Lys Val Asn Asn Lys Asp Leu Pro Ala Pro Ile
            340                 345                 350

Glu Arg Thr Ile Ser Lys Pro Lys Gly Ser Val Arg Ala Pro Gln Val
            355                 360                 365

Tyr Val Leu Pro Pro Pro Glu Glu Glu Met Thr Lys Lys Gln Val Thr
370                 375                 380

Leu Thr Cys Met Val Thr Asp Phe Met Pro Glu Asp Ile Tyr Val Glu
385                 390                 395                 400

Trp Thr Asn Asn Gly Lys Thr Glu Leu Asn Tyr Lys Asn Thr Glu Pro
                405                 410                 415

Val Leu Asp Ser Asp Gly Ser Tyr Phe Met Tyr Ser Lys Leu Arg Val
                420                 425                 430

Glu Lys Lys Asn Trp Val Glu Arg Asn Ser Tyr Ser Cys Ser Val Val
            435                 440                 445

His Glu Gly Leu His Asn His His Thr Thr Lys Ser Phe Ser Arg Thr
            450                 455                 460

Pro Gly Lys
465

<210> SEQ ID NO 63
<211> LENGTH: 714
<212> TYPE: DNA
<213> ORGANISM: Artificial sequence
<220> FEATURE:
```

<223> OTHER INFORMATION: Synthetic construct
<220> FEATURE:
<221> NAME/KEY: CDS
<222> LOCATION: (1)..(714)

<400> SEQUENCE: 63

```
atg gag aca gac aca ctc ctg tta tgg gta ctg ctg ctc tgg gtt cca        48
Met Glu Thr Asp Thr Leu Leu Leu Trp Val Leu Leu Leu Trp Val Pro
1               5                   10                  15 ggt tcc act ggt gac att gtg ctg aca cag tct cct gct tcc tta gct        96
Gly Ser Thr Gly Asp Ile Val Leu Thr Gln Ser Pro Ala Ser Leu Ala
            20                  25                  30 gta tct ctg ggg cag agg gcc acc atc tca tgc agg gcc agc aaa agt       144
Val Ser Leu Gly Gln Arg Ala Thr Ile Ser Cys Arg Ala Ser Lys Ser
        35                  40                  45 gtc agt aca tct ggc tat agt tat atg cac tgg tac caa cag aaa cca       192
Val Ser Thr Ser Gly Tyr Ser Tyr Met His Trp Tyr Gln Gln Lys Pro
    50                  55                  60 gga cag cca ccc aaa ctc ctc atc tat ctt gca tcc aac cta gaa tct       240
Gly Gln Pro Pro Lys Leu Leu Ile Tyr Leu Ala Ser Asn Leu Glu Ser
65                  70                  75                  80 ggg gtc cct gcc agg ttc agt ggc agt ggg tct ggg aca gac ttc acc       288
Gly Val Pro Ala Arg Phe Ser Gly Ser Gly Ser Gly Thr Asp Phe Thr
                85                  90                  95 ctc aac atc cat cct gtg gag gag gag gat gct gca acc tat tac tgt       336
Leu Asn Ile His Pro Val Glu Glu Glu Asp Ala Ala Thr Tyr Tyr Cys
            100                 105                 110 cag cac agt agg gag ctg tac acg ttc gga ggg ggg acc aag ctg gaa       384
Gln His Ser Arg Glu Leu Tyr Thr Phe Gly Gly Gly Thr Lys Leu Glu
        115                 120                 125 ata aaa cgg gct gat gct gca cca act gta tcc atc ttc cca cca tcc       432
Ile Lys Arg Ala Asp Ala Ala Pro Thr Val Ser Ile Phe Pro Pro Ser
    130                 135                 140 agt gag cag tta aca tct gga ggt gcc tca gtc gtg tgc ttc ttg aac       480
Ser Glu Gln Leu Thr Ser Gly Gly Ala Ser Val Val Cys Phe Leu Asn
145                 150                 155                 160 aac ttc tac ccc aaa gac atc aat gtc aag tgg aag att gat ggc agt       528
Asn Phe Tyr Pro Lys Asp Ile Asn Val Lys Trp Lys Ile Asp Gly Ser
                165                 170                 175 gaa cga caa aat ggc gtc ctg aac agt tgg act gat cag gac agc aaa       576
Glu Arg Gln Asn Gly Val Leu Asn Ser Trp Thr Asp Gln Asp Ser Lys
            180                 185                 190 gac agc acc tac agc atg agc agc acc ctc acg ttg acc aag gac gag       624
Asp Ser Thr Tyr Ser Met Ser Ser Thr Leu Thr Leu Thr Lys Asp Glu
        195                 200                 205 tat gaa cga cat aac agc tat acc tgt gag gcc act cac aag aca tca       672
Tyr Glu Arg His Asn Ser Tyr Thr Cys Glu Ala Thr His Lys Thr Ser
    210                 215                 220 act tca ccc att gtc aag agc ttc aac agg aat gag tgt tag              714
Thr Ser Pro Ile Val Lys Ser Phe Asn Arg Asn Glu Cys
225                 230                 235
```

<210> SEQ ID NO 64
<211> LENGTH: 237
<212> TYPE: PRT
<213> ORGANISM: Artificial sequence
<220> FEATURE:
<223> OTHER INFORMATION: Synthetic polypeptide: 93-22 L chain

<400> SEQUENCE: 64

```
Met Glu Thr Asp Thr Leu Leu Leu Trp Val Leu Leu Leu Trp Val Pro
1               5                   10                  15
```

-continued

```
Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Gly Tyr Ser Tyr Met His Trp Tyr Gln Gln Lys Pro
 50                  55                  60

Gly Gln Pro Pro Lys Leu Leu Ile Tyr Leu Ala Ser Asn Leu Glu Ser
 65                  70                  75                  80

Gly Val Pro Ala Arg Phe Ser Gly Ser Gly Ser Gly Thr Asp Phe Thr
                 85                  90                  95

Leu Asn Ile His Pro Val Glu Glu Glu Asp Ala Ala Thr Tyr Tyr Cys
            100                 105                 110

Gln His Ser Arg Glu Leu Tyr Thr Phe Gly Gly Gly Thr Lys Leu Glu
        115                 120                 125

Ile Lys Arg Ala Asp Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
210                 215                 220

Thr Ser Pro Ile Val Lys Ser Phe Asn Arg Asn Glu Cys
225                 230                 235

<210> SEQ ID NO 65
<211> LENGTH: 1395
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1395)

<400> SEQUENCE: 65 atg gat tgg ctg tgg aac ttg cta ttc ctg atg gca gct gcc caa agt      48
Met Asp Trp Leu Trp Asn Leu Leu Phe Leu Met Ala Ala Ala Gln Ser
1               5                   10                  15 atc caa gca cag atc cag ttg gtg cag tct gga cct gag ctg aag aag      96
Ile Gln Ala Gln Ile Gln Leu Val Gln Ser Gly Pro Glu Leu Lys Lys
            20                  25                  30 cct gga gag aca gtc aag atc tcc tgc aag gct tct ggg tat acc ttc     144
Pro Gly Glu Thr Val Lys Ile Ser Cys Lys Ala Ser Gly Tyr Thr Phe
        35                  40                  45 aca aac tat gga atg aac tgg gtg aag cag gct cca gga aag ggt tta     192
Thr Asn Tyr Gly Met Asn Trp Val Lys Gln Ala Pro Gly Lys Gly Leu
 50                  55                  60 aag tgg atg ggc tgg ata aac acc aac act gga gag cca aca tat gct     240
Lys Trp Met Gly Trp Ile Asn Thr Asn Thr Gly Glu Pro Thr Tyr Ala
65                  70                  75                  80 gaa gag ttc aag gga cgg ttt gcc ttc tct ttg gaa acc tct gcc agc     288
Glu Glu Phe Lys Gly Arg Phe Ala Phe Ser Leu Glu Thr Ser Ala Ser
                 85                  90                  95
```

```
act gcc tat ttg cag atc aac aac ctc aaa aat gag gac acg gct aca        336
Thr Ala Tyr Leu Gln Ile Asn Asn Leu Lys Asn Glu Asp Thr Ala Thr
            100                 105                 110 tat ttc tgt gca aga ggg ggg tac ggg gac tac tgg ggc caa ggc acc        384
Tyr Phe Cys Ala Arg Gly Gly Tyr Gly Asp Tyr Trp Gly Gln Gly Thr
        115                 120                 125 act ctc aca gtc tcc tca gcc aaa aca aca gcc cca tcg gtc tat cca        432
Thr Leu Thr Val Ser Ser Ala Lys Thr Thr Ala Pro Ser Val Tyr Pro
    130                 135                 140 ctg gcc cct gtg tgt gga gat aca act ggc tcc tcg gtg act cta gga        480
Leu Ala Pro Val Cys Gly Asp Thr Thr Gly Ser Ser Val Thr Leu Gly
145                 150                 155                 160 tgc ctg gtc aag ggt tat ttc cct gag cca gtg acc ttg acc tgg aac        528
Cys Leu Val Lys Gly Tyr Phe Pro Glu Pro Val Thr Leu Thr Trp Asn
                165                 170                 175 tct gga tcc ctg tcc agt ggt gtg cac acc ttc cca gct gtc ctg cag        576
Ser Gly Ser Leu Ser Ser Gly Val His Thr Phe Pro Ala Val Leu Gln
            180                 185                 190 tct gac ctc tac acc ctc agc agc tca gtg act gta acc tcg agc acc        624
Ser Asp Leu Tyr Thr Leu Ser Ser Ser Val Thr Val Thr Ser Ser Thr
        195                 200                 205 tgg ccc agc cag tcc atc acc tgc aat gtg gcc cac ccg gca agc agc        672
Trp Pro Ser Gln Ser Ile Thr Cys Asn Val Ala His Pro Ala Ser Ser
    210                 215                 220 acc aag gtg gac aag aaa att gag ccc aga ggg ccc aca atc aag ccc        720
Thr Lys Val Asp Lys Lys Ile Glu Pro Arg Gly Pro Thr Ile Lys Pro
225                 230                 235                 240 tgt cct cca tgc aaa tgc cca gca cct aac ctc ttg ggt gga cca tcc        768
Cys Pro Pro Cys Lys Cys Pro Ala Pro Asn Leu Leu Gly Gly Pro Ser
                245                 250                 255 gtc ttc atc ttc cct cca aag atc aag gat gta ctc atg atc tcc ctg        816
Val Phe Ile Phe Pro Pro Lys Ile Lys Asp Val Leu Met Ile Ser Leu
            260                 265                 270 agc ccc ata gtc aca tgt gtg gtg gtg gat gtg agc gag gat gac cca        864
Ser Pro Ile Val Thr Cys Val Val Val Asp Val Ser Glu Asp Asp Pro
        275                 280                 285 gat gtc cag atc agc tgg ttt gtg aac aac gtg gaa gta cac aca gct        912
Asp Val Gln Ile Ser Trp Phe Val Asn Asn Val Glu Val His Thr Ala
    290                 295                 300 cag aca caa acc cat aga gag gat tac aac agt act ctc cgg gtg gtc        960
Gln Thr Gln Thr His Arg Glu Asp Tyr Asn Ser Thr Leu Arg Val Val
305                 310                 315                 320 agt gcc ctc ccc atc cag cac cag gac tgg atg agt ggc aag gag ttc       1008
Ser Ala Leu Pro Ile Gln His Gln Asp Trp Met Ser Gly Lys Glu Phe
                325                 330                 335 aaa tgc aag gtc aac aac aaa gac ctc cca gcg ccc atc gag aga acc       1056
Lys Cys Lys Val Asn Asn Lys Asp Leu Pro Ala Pro Ile Glu Arg Thr
            340                 345                 350 atc tca aaa ccc aaa ggg tca gta aga gct cca cag gta tat gtc ttg       1104
Ile Ser Lys Pro Lys Gly Ser Val Arg Ala Pro Gln Val Tyr Val Leu
        355                 360                 365 cct cca cca gaa gaa gag atg act aag aaa cag gtc act ctg acc tgc       1152
Pro Pro Pro Glu Glu Glu Met Thr Lys Lys Gln Val Thr Leu Thr Cys
    370                 375                 380 atg gtc aca gac ttc atg cct gaa gac att tac gtg gag tgg acc aac       1200
Met Val Thr Asp Phe Met Pro Glu Asp Ile Tyr Val Glu Trp Thr Asn
385                 390                 395                 400 aac ggg aaa aca gag cta aac tac aag aac act gaa cca gtc ctg gac       1248
Asn Gly Lys Thr Glu Leu Asn Tyr Lys Asn Thr Glu Pro Val Leu Asp
```

```
                    405                 410                 415
tct gat ggt tct tac ttc atg tac agc aag ctg aga gtg gaa aag aag    1296
Ser Asp Gly Ser Tyr Phe Met Tyr Ser Lys Leu Arg Val Glu Lys Lys
            420                 425                 430 aac tgg gtg gaa aga aat agc tac tcc tgt tca gtg gtc cac gag ggt    1344
Asn Trp Val Glu Arg Asn Ser Tyr Ser Cys Ser Val Val His Glu Gly
            435                 440                 445 ctg cac aat cac cac acg act aag agc ttc tcc cgg act ccg ggt aaa    1392
Leu His Asn His His Thr Thr Lys Ser Phe Ser Arg Thr Pro Gly Lys
            450                 455                 460 tga                                                                 1395
```

<210> SEQ ID NO 66
<211> LENGTH: 464
<212> TYPE: PRT
<213> ORGANISM: Artificial sequence
<220> FEATURE:
<223> OTHER INFORMATION: Synthetic polypeptide: 39-10 H chain

<400> SEQUENCE: 66

```
Met Asp Trp Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Gly Gly Tyr Gly Asp Tyr Trp Gly Gln Gly Thr
        115                 120                 125

Thr Leu Thr Val Ser Ser Ala Lys Thr Thr Ala Pro Ser Val Tyr Pro
    130                 135                 140

Leu Ala Pro Val Cys Gly Asp Thr Thr Gly Ser Ser Val Thr Leu Gly
145                 150                 155                 160

Cys Leu Val Lys Gly Tyr Phe Pro Glu Pro Val Thr Leu Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Thr Ser Ser Thr
        195                 200                 205

Trp Pro Ser Gln Ser Ile Thr Cys Asn Val Ala His Pro Ala Ser Ser
    210                 215                 220

Thr Lys Val Asp Lys Lys Ile Glu Pro Arg Gly Pro Thr Ile Lys Pro
225                 230                 235                 240

Cys Pro Pro Cys Lys Cys Pro Ala Pro Asn Leu Leu Gly Gly Pro Ser
                245                 250                 255

Val Phe Ile Phe Pro Pro Lys Ile Lys Asp Val Leu Met Ile Ser Leu
            260                 265                 270

Ser Pro Ile Val Thr Cys Val Val Val Asp Val Ser Glu Asp Asp Pro
        275                 280                 285
```

```
Asp Val Gln Ile Ser Trp Phe Val Asn Asn Val Glu Val His Thr Ala
        290                 295                 300

Gln Thr Gln Thr His Arg Glu Asp Tyr Asn Ser Thr Leu Arg Val Val
305                 310                 315                 320

Ser Ala Leu Pro Ile Gln His Gln Asp Trp Met Ser Gly Lys Glu Phe
                325                 330                 335

Lys Cys Lys Val Asn Asn Lys Asp Leu Pro Ala Pro Ile Glu Arg Thr
                340                 345                 350

Ile Ser Lys Pro Lys Gly Ser Val Arg Ala Pro Gln Val Tyr Val Leu
            355                 360                 365

Pro Pro Pro Glu Glu Met Thr Lys Lys Gln Val Thr Leu Thr Cys
370                 375                 380

Met Val Thr Asp Phe Met Pro Glu Asp Ile Tyr Val Glu Trp Thr Asn
385                 390                 395                 400

Asn Gly Lys Thr Glu Leu Asn Tyr Lys Asn Thr Glu Pro Val Leu Asp
                405                 410                 415

Ser Asp Gly Ser Tyr Phe Met Tyr Ser Lys Leu Arg Val Glu Lys Lys
                420                 425                 430

Asn Trp Val Glu Arg Asn Ser Tyr Ser Cys Ser Val Val His Glu Gly
            435                 440                 445

Leu His Asn His His Thr Thr Lys Ser Phe Ser Arg Thr Pro Gly Lys
            450                 455                 460
```

<210> SEQ ID NO 67
<211> LENGTH: 717
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(717)

<400> SEQUENCE: 67

```
atg gag aca gac aca ctc ctg cta tgg gtg ctg ctg ctc tgg gtt cca    48
Met Glu Thr Asp Thr Leu Leu Leu Trp Val Leu Leu Leu Trp Val Pro
1               5                   10                  15 ggt tcc aca ggt gac att gtg ctg acc caa tct cca gct tct ttg gct    96
Gly Ser Thr Gly Asp Ile Val Leu Thr Gln Ser Pro Ala Ser Leu Ala
            20                  25                  30 gtg tct cta ggg cag agg gcc acc ata tcc tgc aga gcc agt gaa agt   144
Val Ser Leu Gly Gln Arg Ala Thr Ile Ser Cys Arg Ala Ser Glu Ser
        35                  40                  45 gtt gat agt tat ggc aat agt ttt atg cac tgg tac cag cag aaa cca   192
Val Asp Ser Tyr Gly Asn Ser Phe Met His Trp Tyr Gln Gln Lys Pro
    50                  55                  60 gga cag cca ccc aaa ctc ctc atc tat cgt gca tcc aac cta gaa tct   240
Gly Gln Pro Pro Lys Leu Leu Ile Tyr Arg Ala Ser Asn Leu Glu Ser
65                  70                  75                  80 ggg atc cct gcc agg ttc agt ggc agt ggg tct agg aca gac ttc acc   288
Gly Ile Pro Ala Arg Phe Ser Gly Ser Gly Ser Arg Thr Asp Phe Thr
                85                  90                  95 ctc acc att aat cct gtg gag gct gat gat gtt gca acc tat tac tgt   336
Leu Thr Ile Asn Pro Val Glu Ala Asp Asp Val Ala Thr Tyr Tyr Cys
            100                 105                 110 cag caa agt aat gag gat cct cgg acg ttc ggt gga ggc acc aag ctg   384
Gln Gln Ser Asn Glu Asp Pro Arg Thr Phe Gly Gly Gly Thr Lys Leu
        115                 120                 125
```

```
gaa atc aaa cgg gct gat gct gca cca act gta tcc atc ttc cca cca    432
Glu Ile Lys Arg Ala Asp Ala Ala Pro Thr Val Ser Ile Phe Pro Pro
130                 135                 140 tcc agt gag cag tta aca tct gga ggt gcc tca gtc gtg tgc ttc ttg    480
Ser Ser Glu Gln Leu Thr Ser Gly Gly Ala Ser Val Val Cys Phe Leu
145                 150                 155                 160 aac aac ttc tac ccc aaa gac atc aat gtc aag tgg aag att gat ggc    528
Asn Asn Phe Tyr Pro Lys Asp Ile Asn Val Lys Trp Lys Ile Asp Gly
                165                 170                 175 agt gaa cga caa aat ggc gtc ctg aac agt tgg act gat cag gac agc    576
Ser Glu Arg Gln Asn Gly Val Leu Asn Ser Trp Thr Asp Gln Asp Ser
            180                 185                 190 aaa gac agc acc tac agc atg agc agc acc ctc acg ttg acc aag gac    624
Lys Asp Ser Thr Tyr Ser Met Ser Ser Thr Leu Thr Leu Thr Lys Asp
        195                 200                 205 gag tat gaa cga cat aac agc tat acc tgt gag gcc act cac aag aca    672
Glu Tyr Glu Arg His Asn Ser Tyr Thr Cys Glu Ala Thr His Lys Thr
    210                 215                 220 tca act tca ccc att gtc aag agc ttc aac agg aat gag tgt tag        717
Ser Thr Ser Pro Ile Val Lys Ser Phe Asn Arg Asn Glu Cys
225                 230                 235

<210> SEQ ID NO 68
<211> LENGTH: 238
<212> TYPE: PRT
<213> ORGANISM: Artificial sequence
<220> FEATURE:
<223> OTHER INFORMATION: Synthetic polypeptide: 39-10 L chain

<400> SEQUENCE: 68

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Arg Ala Ser Asn Leu Glu Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Thr Tyr Tyr Cys
            100                 105                 110

Gln Gln Ser Asn Glu Asp Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205
```

```
Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

US 9,139,655 B2

TUMOR-TARGETING MONOCLONAL ANTIBODIES TO FZD10 AND USES THEREOF

CROSS-REFERENCE TO RELATED APPLICATION

This application is a Divisional of application Ser. No. 12/308,095, filed on Dec. 8, 2008, granted as U.S. Pat. No. 8,221,751, and for which priority is claimed under 35 U.S.C. §120. Application Ser. No. 12/308,095 is the national phase of PCT International Application No. PCT/JP2006/317155 filed on Aug. 24, 2006 under 35 U.S.C. §371, which claims priority under 35 U.S.C. §119(e) to U.S. Provisional Application No. 60/815,257, filed on Jun. 21, 2006. The entire contents of each of the above-identified applications are hereby incorporated by reference.

FIELD OF THE INVENTION

The present invention relates to an antibody or a fragment thereof which is capable of binding to a Frizzled homologue 10 (FZD10) protein, such as a mouse monoclonal antibody, a chimeric antibody and a humanized antibody. Also, the present invention relates to a method for treating and/or preventing FZD10-associated disease; a method for diagnosis or prognosis of FZD10-associated disease; and a method for in vivo imaging of FZD10 in a subject.

BACKGROUND OF THE INVENTION

Monoclonal antibodies against cancer-specific molecules have been proved to be useful in cancer treatment (Harris, M. (2004). Lancet Oncol, 5, 292-302). In addition to successful examples of clinical application of the humanized or chimeric antibodies such as trastuzumab (Baselga, J. (2004). Oncology, 61, Suppl 2 14-21), rituximab (Maloney, D. G., et al. (1997). Blood, 90, 2188-95) and bevacizumab (Ferrara, N., et al. (2004). Nat Rev Drug Discov, 3, 391-400) for breast cancer, malignant lymphoma and colon cancer, a number of monoclonal antibodies against other molecular targets are in development and being evaluated their anti-tumor activities. These monoclonal antibodies are expected to provide a hope to patients having tumors that have no effective treatment. One of the other important issues for these monoclonal antibodies is achievement of selective therapeutic effects to cancer cells without severe toxicity due to their specific reaction to cells expressing target molecules (Crist, W. M., et al. (2001). J Clin Oncol, 19, 3091-102; Wunder, J. S., et al. (1998). J Bone Joint Surg Am, 80, 1020-33; Ferguson, W. S. and Goorin, A. M. (2001). Cancer Invest, 19, 292-315).

Among soft tissue sarcomas, osteosarcoma, Ewing's sarcoma and rhabdomyosarcoma are sensitive to chemotherapy and these diseases can be well managed by chemotherapy. On the other hand, spindle cell sarcomas are resistant to chemo- and radiotherapy and patients with them usually exhibit poor prognosis. For synovial sarcoma (SS), surgical treatment is effective for patients at an early stage, but no effective therapeutic drug is available to those at an advanced stage. Hence, development of novel therapeutic modalities is expected to improve patients' prognosis better.

Genome-wide gene expression analysis in tumors provides the useful information to identify the new molecular targets for development of novel anticancer drugs and tumor markers. In previous study, the present inventors have analyzed gene-expression profile of several soft tissue sarcomas using genome-wide cDNA microarray consisting of 23,040 genes and demonstrated that Frizzled homologue10 (FZD10) (GenBank Accession NOs. AB027464 (SEQ ID NO:1) and BAA84093 (SEQ ID NO:2)) was up-regulated specifically and frequently in SSs (Nagayama, S., et al. (2002) Cancer Res, 62, 5859-66; and WO2004/020668). FZD10 gene product is a member of Frizzled family and a putative WNT signal receptor (Koike, J., et al. (1999). Biochem Biophys Res Commun, 262, 39-43). Further analysis showed that FZD10 is expressed specifically in SS, and at no or hardly-detectable level in other normal organs except the placenta, suggesting that therapeutics targeting this molecule would cause no or little adverse reaction (Nagayama, S., et al. (2002). Cancer Res, 62, 5859-66). RNAi experiments implicated that FZD10 was significantly involved in the tumor growth of SS (WO2006/013733). Furthermore, the present inventors generated the rabbit polyclonal antibody against the extracellular domain of FZD10 (FZD10-ECD), and found that this antibody had antitumor activity in mouse xenograft model of SS (Nagayama, S., et al. (2005). Oncogene, 24, 6201-12; and WO2005/004912). Together, the antibody therapy against FZD10 could be expected to improve the clinical outcome of SS.

SUMMARY OF THE INVENTION

Hereinbelow, it is reported that generation of the murine monoclonal antibodies against FZD10 by means of cell-immunization method for possible clinical application. In vivo tumor-binding activity of these antibodies was evaluated using fluorescent in vivo imaging system with near-infrared fluorescence in addition to the conventional method with radionuclides. Here, we reveal the binding specificity of anti-FZD10 monoclonal antibodies both in vitro and in vivo as well as internalization of these antibodies in the cells expressing FZD10, and found that SYO-1-bearing xenograft mice treated with a single tail vain of $^{90}$Y-labeled anti-FZD10 Mab at 100 μCi dose was observed significant antitumor effect.

Based on the above findings, the present inventors concluded that the murine monoclonal antibodies against FZD10 have therapeutic potential in the treatment and diagnosis of SS and other FZD10-overexpressing tumors.

Therefore, in the first aspect, the present invention provides an antibody or a fragment thereof, which comprises an H (heavy) chain V (variable) region comprising a complementarity determining region (CDR) having the amino acid sequences shown in SEQ ID NOs: 15, 17 and 19 or a CDR functionally equivalent thereto and an L (light) chain V region comprising a CDR having the amino acid sequences shown in SEQ ID NOs: 23, 25 and 27 a CDR functionally equivalent thereto, and which is capable of binding to a Frizzled homologue 10 (FZD10) protein or a partial peptide thereof.

In one embodiment, the antibody or fragment thereof is selected from the group consisting of a mouse antibody, a chimeric antibody, a humanized antibody, an antibody fragment, and single-chain antibody.

In a preferred embodiment, the antibody is a mouse antibody. Preferably, the mouse antibody comprises an H chain having the amino acid sequence shown in SEQ ID NO: 57 and/or an L chain having the amino acid sequence shown in SEQ ID NO: 59. For example, the mouse antibody can be produced by the hybridoma clone 92-13 (FERM BP-10628).

In an alternative preferred embodiment, the antibody is a chimeric antibody. Preferably, the chimeric antibody comprises an H chain V region having the amino acid sequence shown in SEQ ID NO: 13, for example, the chimeric antibody may comprise an H chain having the amino acid sequence shown in SEQ ID NO: 46. Preferably, the chimeric antibody comprises an L chain V region having the amino acid sequence shown in SEQ ID NO: 21, for example, the chimeric antibody may comprise an L chain having the amino acid sequence shown in SEQ ID NO: 48.

More preferably, the chimeric antibody comprises an H chain V region having the amino acid sequence shown in SEQ ID NO: 13 and an L chain V region having the amino acid sequence shown in SEQ ID NO: 21. For example, the chimeric antibody comprises an H chain having the amino acid sequence shown in SEQ ID NO: 46 and an L chain having the amino acid sequence shown in SEQ ID NO: 48.

In one embodiment, the chimeric antibody further comprises a human antibody C (constant) region.

In an alternative preferred embodiment, the antibody is a humanized antibody. In one embodiment, the humanized antibody further comprises a human antibody FR (framework) region and/or a human antibody C region.

In the second aspect, the present invention provides an antibody or a fragment thereof, which comprises an H (heavy) chain V (variable) region comprising a complementarity determining region (CDR) having the amino acid sequences shown in SEQ ID NOs: 31, 33 and 35 or a CDR functionally equivalent thereto and an L (light) chain V region comprising a CDR having the amino acid sequences shown in SEQ ID NOs: 39, 41 and 43 or a CDR functionally equivalent thereto, and which is capable of binding to a Frizzled homologue 10 (FZD10) protein or a partial peptide thereof.

In one embodiment, the antibody or fragment thereof is selected from the group consisting of a mouse antibody, a chimeric antibody, a humanized antibody, an antibody fragment, and single-chain antibody.

In a preferred embodiment, the antibody is a mouse antibody. Preferably, the mouse antibody comprises an H chain having the amino acid sequence shown in SEQ ID NO: 61 and/or an L chain having the amino acid sequence shown in SEQ ID NO: 63. For example, the mouse antibody can be produced by the hybridoma clone 93-22 (FERM BP-10620).

In an alternative preferred embodiment, the antibody is a chimeric antibody. Preferably, the chimeric antibody comprises an H chain V region having the amino acid sequence shown in SEQ ID NO: 29, for example, the chimeric antibody comprises an H chain having the amino acid sequence shown in SEQ ID NO: 50. Preferably, the chimeric antibody comprises an L chain V region having the amino acid sequence shown in SEQ ID NO: 37, for example, the chimeric antibody comprises an L chain having the amino acid sequence shown in SEQ ID NO: 52.

More preferably, the chimeric antibody comprises an H chain V region having the amino acid sequence shown in SEQ ID NO: 29 and an L chain V region having the amino acid sequence shown in SEQ ID NO: 37. For example, the chimeric antibody comprises an H chain having the amino acid sequence shown in SEQ ID NO: 50 and an L chain having the amino acid sequence shown in SEQ ID NO: 52.

In one embodiment, the chimeric antibody further comprises a human antibody C (constant) region.

In an alternative preferred embodiment, the antibody is a humanized antibody. In one embodiment, the humanized antibody further comprises a human antibody FR (framework) region and/or a human antibody C region.

In yet an alternative embodiment, the antibody or fragment thereof can be labeled with a radioisotope label or a fluorescent label. Such radioisotope label includes $^{90}$yttrium ($^{90}$Y), $^{125}$iodine ($^{125}$I) and $^{111}$indium ($^{111}$In).

In the third aspect, the present invention provides a hybridoma clone 92-13 (FERM BP-10628) which produces the mouse monoclonal antibody 92-13.

In the forth aspect, the present invention provides a hybridoma clone 93-22 (FERM BP-10620) which produces the mouse monoclonal antibody 93-22.

In the fifth aspect, the present invention provides a method for treating or preventing a disease that is associated with Frizzled homologue 10 (FZD10) in a subject, comprising administering to the subject an effective amount of the antibody or fragment above. In one embodiment, the disease that is associated with FZD10 is selected from synovial sarcoma (SS), colorectal cancer, gastric cancer, chronic myeloid leukemia (CML), and acute myeloid leukemia (AML).

In the sixth aspect, the present invention provides a method for diagnosis or prognosis of a disease that is associated with Frizzled homologue 10 (FZD10) or of a predisposition to develop the disease in a subject, comprising
(a) contacting a sample or a specimen from the subject with the antibody or fragment above;
(b) detecting the FZD10 protein in the sample or specimen; and
(c) judging whether or not the subject suffers from or is at risk of developing the disease based on the relative abundance of the FZD10 protein compared to a control.

In one embodiment, the disease that is associated with FZD10 is selected from synovial sarcoma (SS), colorectal cancer, gastric cancer, chronic myeloid leukemia (CML), and acute myeloid leukemia (AML).

In the seventh aspect, the present invention provides a method for in vivo imaging of Frizzled homologue 10 (FZD10) protein in a subject, comprising administering to the subject an effective amount of the antibody or fragment above.

In the eighth aspect, the present invention provides a pharmaceutical composition for treating or preventing a disease associated with Frizzled homologue 10 (FZD10), comprising the antibody or fragment above and a pharmaceutically acceptable carrier or excipient.

In the ninth aspect, the present invention provides a kit for diagnosis or prognosis of a disease associated with Frizzled homologue 10 (FZD10), comprising the antibody or fragment above.

In the tenth aspect, the present invention provides a pharmaceutical composition for in vivo imaging of Frizzled homologue 10 (FZD10) protein, comprising the antibody or fragment above.

In the eleventh aspect, the present invention provides use of the antibody or fragment above in the manufacture of a kit for diagnosis or prognosis of a disease associated with Frizzled homologue 10 (FZD10).

In the twelfth aspect, the present invention provides use of the antibody or fragment above in the manufacture of a composition for prevention or treatment of a disease associated with Frizzled homologue 10 (FZD10).

The term "disease that is associated with FZD10" (FZD10-associated disease) refers to a disease that is associated with over-expression of FZD10 protein. Such diseases include, but are not limited to, synovial sarcoma (SS), colorectal cancer, gastric cancer, chronic myeloid leukemia (CML), and acute myeloid leukemia (AML).

The term "fragment" means any antibody fragment that can be prepared from the antibody against FZD10 protein and contains defined CDRs. Such fragment includes, but not limited to, Fab fragment, F (ab')$_2$ fragment, and Fv fragment.

The term "modified antibody" means any antibody that can be derived from the antibody against FZD10 and contains defined CDRs. Such modified antibody includes, but not limited to, a PEG-modified antibody. The antibody fragment or modified fragment can be readily recognized by a person skilled in the art and produced by using any methods known in the art.

The term "subject" herein refers to a subject who has suffered from FZD10-associated disease and also a subject suspected to have FZD10-associated disease. The subject in the present invention may be animals including mammals and avian animals. For example, mammals may include humans, mice, rats, monkeys, rabbits, and dogs.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 1a shows flow-cytometric analysis of the four antibodies, 39-2 and 39-10 (disclosed in WO2005/004912), 92-13 and 93-22, using five SS lines (SYO-1, YaFuSS, HS-SY-2, Fuji and 1973/99) and one colon-cancer cell line (LoVo). Solid lines show the fluorescent intensity detected by each mAbs; broken lines depict the fluorescent intensities of cells incubated with non-immunized mouse IgG as a negative control.

FIG. 1b shows semi-quantitative RT-PCR of FZD10 in the same tumor-cell lines as used in FIG. 1a. Expression of β2-microglobulin gene (β2MG) served as an internal control.

FIG. 1c shows flow-cytometric analysis of 92-13 (top panels) and 93-22 (lower panels) against exogenous FZD10 were indicated. Colon cancer cell line, SNU-05 was transfected with pCAGGS empty vector (left panels) or pCAGGS-FZD10-myc/His (right panels) and analyzed 48 hours after transfection. Solid lines show the fluorescent intensity detected by each mAbs; broken lines depict the fluorescent intensities of cells incubated with non-immunized mouse IgG as a negative control.

FIG. 1d shows binding of $^{125}$I-labeled 39-10, 39-2, 92-13 and 93-22 to normal human blood cells. Radio-labeled Mabs were incubated with each normal human fresh blood of three individuals (A, B and C) in the absence (open bar) or presence (closed bar) of non-labeled identical antibodies.

FIG. 1e shows binding activity of $^{125}$I-labeled Mabs. A constant amount of radio-labeled Mabs was incubated with SYO-1 cell and increasing amount of non-labeled antibodies. The percent radioactivity bound to cells was plotted against the amount of non-labeled antibody. Closed circle; 92-13, Open circle; 93-22.

FIG. 1f shows flow-cytometric analysis of self-block and cross-block. Alexa-488-labeled 92-13 (Top panels) and 93-22 (Lower panels) were incubated with SYO-1 cell in (i) PBS, or in the presence of 100 μg of (ii) non-labeled 92-13 and (iii) non-labeled 93-22. Shaded histogram show the fluorescent intensity detected by each Alexa488-labeled Mabs; broken lines depict the fluorescent intensities of cells incubated with PBS as a negative control.

DETAILED DESCRIPTION AND PREFERRED EMBODIMENTS OF THE PRESENT INVENTION

Frizzled homologue 10 (FZD10) is a member of Frizzled family, which is a receptor of Wnt signaling. As described hereinbelow, we successfully established murine monoclonal antibodies and chimeric antibodies against FZD10 protein that may be useful for medical use.

The murine monoclonal FZD10-sepcific antibodies (92-13 and 93-22 Mabs) are established by immunizing mice with FZD10-transfected cells. Both 92-13 and 93-22 Mabs were shown to have specific binding activity against FZD10 in SS cell line, SYO-1 cells and FZD10-transfected COS7 cells by using flow cytometry (FACS) analysis. To validate the specific binding activity of those antibodies in vivo, the present inventors injected fluorescent-labeled Mabs intraperitoneally or intravenously into the mice carrying SS xenografts and found that these Mabs were bound to the FZD10-expressing tumors, but not to any other normal mouse tissues by the use of the in vivo fluorescent imaging system and radioactivities. Subsequent immunohistochemical analyses with the Mabs confirmed an absence or hardly-detectable level of FZD10 protein in normal human organs except the placenta. Furthermore, interestingly the present inventors found that the Mabs were internalized into the SS cell line, SYO-1, but not into FZD10-negative cell line, LoVo using confocal laser scanning microscopy. Surprisingly, SYO-1-bearing xenograft mice treated with a single tail vain of $^{90}$Y-labeled anti-FZD10 (92-13) Mab at 100 μCi dose was observed significant anti-tumor effect. Taken together, we conclude that these specific Mabs against FZD10 could be utilized as the novel diagnostic marker or treatment of SS with minimal or no risk of adverse reactions.

Due to their complicated protein structure, it is often very difficult to generate antibodies against seven-transmembrane proteins. In previous study, the present inventors demonstrated that FZD10 formed homo-oligomer (Nagayama, S., et al. (2005). Oncogene, 24, 6201-12). After failure of multiple attempts to generate anti-FZD10 monoclonal antibodies that could recognize a native form of FZD10 by the use of full-length or partial recombinant FZD10 proteins, we finally applied to immunization by injection of living COS-7 cells overexpressing FZD10 into the foot-pad of Balb/c-mice and successfully obtained the two hybridomas producing anti-FZD10 antibodies that had an ability to recognize the native FZD10 form in living cells by FACS analysis. Since those antibodies did not detect FZD10 protein in western blotting, the present inventors assume that those Mabs recognize the tertiary structure of FZD10.

Figure 3:
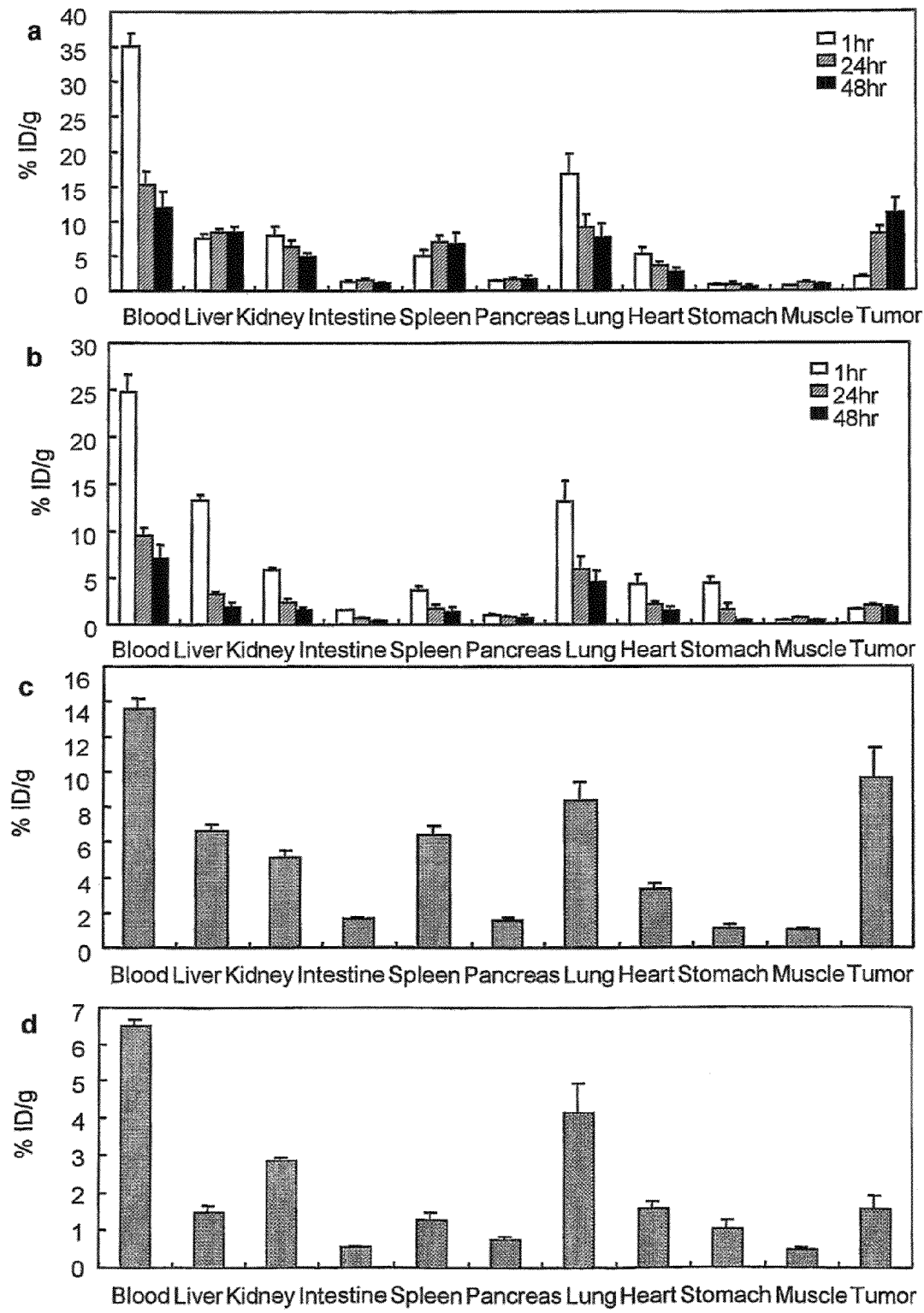
FIG. 3 shows biodistribution of $^{111}$In-labeled and $^{125}$I-labeled antibodies. 10 kBq of (a), $^{111}$In-labeled 92-13, (b), $^{125}$I-labeled 92-13, (c), $^{111}$In-labeled 93-22 and (d), $^{125}$I-labeled 93-22 were injected intravenously into SYO-1 tumor bearing BALB/c nude mice. The organs and tumor were dissected at one hour (open bar), 24 hours (hatched bar) and 48 hours (closed bar), and the radioactivities were measured. The data shown is the representative data in two independent experiments.
Figure 6:
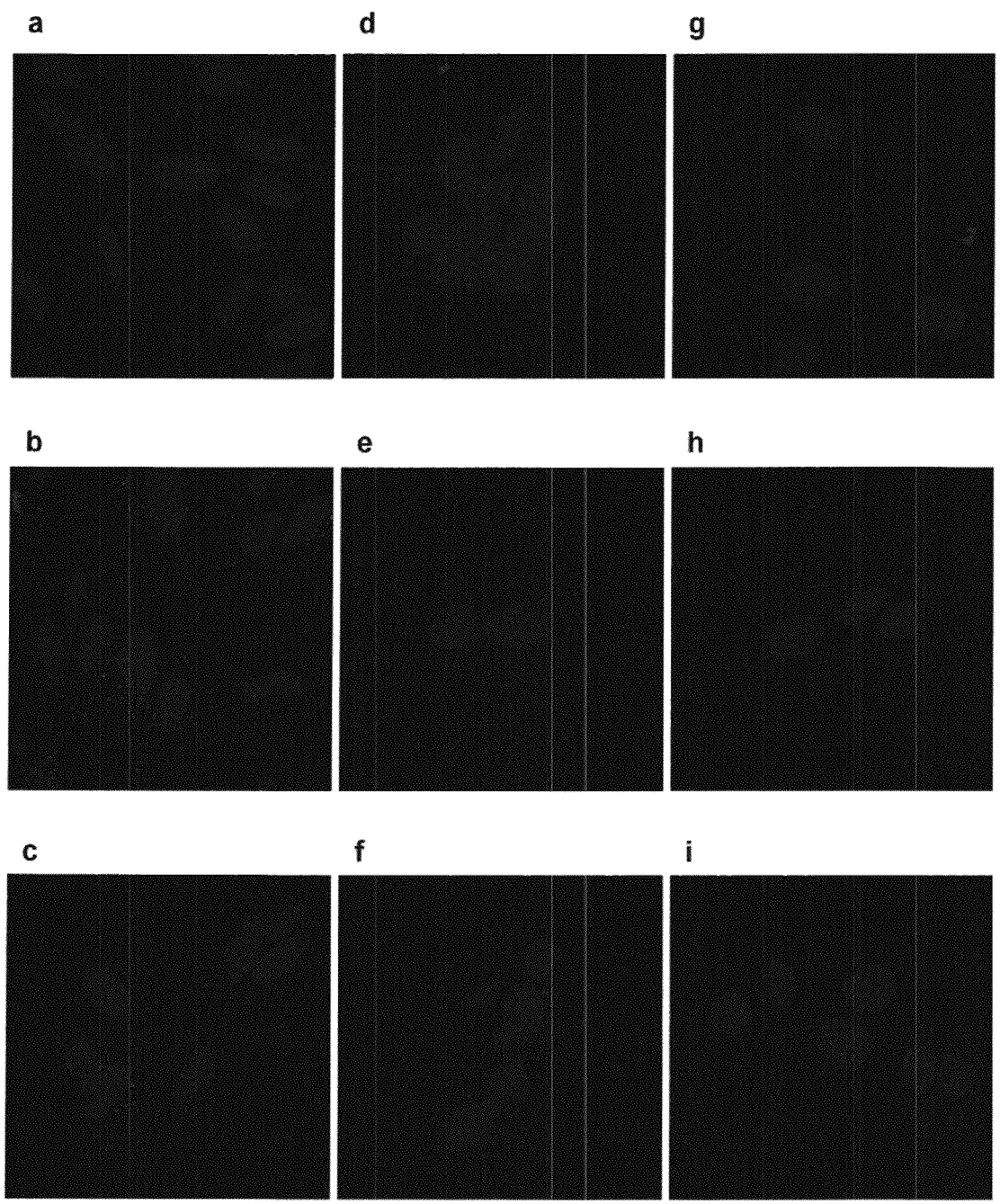
FIG. 6 shows internalization of 92-13 and 93-22 was assessed by confocal microscopy. Cells were treated with PBS (a, d, and g), 50 μg/ml of 92-13 (b, e, and h) or 93-22 (c, f, i) for 3 hours in 37° C., 5% $CO_2$. Antibodies bound to the cell surface were acid-stripped with 0.1M glycine buffer (pH2.5). Cells were fixed, permeabilized and then blocked with 3% BSA. Intracellular antibodies were detected with goat anti-mouse IgG-Alexa488 and nucleus was stained with DAPI. (a-c), SYO-1; (d-f), YaFuSS; (g-i) Lovo.

To investigate the in vivo distribution of 92-13 and 93-22 Mabs, the present inventors applied two methods; one based on the radionuclide modalities using $^{125}$I and $^{111}$In-labeled antibodies, and the other based on the fluorescence imaging using near-infrared-labeled (Alexa647) antibodies. Near-infrared fluorescent, mostly indocyanine dye, is now widely used in the in vivo imaging for diagnostic purpose because the light of this wavelength penetrates living tissue quite efficiently (Chen, X., et al. (2004). Cancer Res, 64, 8009-14). The results obtained two approaches were very concordant and indicated that 92-13 and 93-22 bound to SYO-1 tumor cells, but not to other normal tissues. To confirm whether those antibodies can be applied for clinical use, the present inventors further examined the binding activity of antibodies against normal blood cells. The binding activity of $^{125}$I-labeled 92-13 and 93-22 against normal human blood cells were undetectable in all of three individual donors (FIG. 1$d$). These results were consistent with those of FACS analysis using human peripheral blood mononuclear cell (data not shown), suggesting clinical applicability of these two antibodies with little possibility of adverse effect to SS patients because of very specific binding affinity to the FZD10 molecule. Furthermore, in vitro experiments using confocal microscopy reveled that the specific binding of 92-13 and 93-22 Mabs to cell-surface FZD10 induced the internalization of the antibodies (FIG. 6). As described previously (Stein, R., et al. (2001). Criti Rev Oncol Hematol, 39, 173-80; Stein, R., et al. (2005). Clin Cancer Res, 11, 2727-34), if labeled Mabs is internalized after binding, $^{125}$I-labeled antibody is metabolized in the lysosomes and diffused from target tumor cells where $^{111}$In-labeled antibody remains in the lysosomes. As observed in FIG. 3, the radioactivities of $^{111}$In-labeled antibody and $^{125}$I-labeled antibody in tumors were significantly different (FIGS. 3, $a$ and $b$, $c$ and $d$). These findings suggest that 92-13 (and 93-22) Mabs can specifically internalize into the SS cells via FZD10 protein.

When antibodies are applied to cancer therapy, the following three mechanisms are thought to exert the anti-tumor activity; (i) in case that the target molecule is involved in growth enhancement, neutralization of antibodies would block the growth signal transduction and then suppress the growth of tumor cells; (ii) The second possibility is the effector activities to induce antibody-dependent cell-mediated cytotoxity (ADCC) or complement-dependent cytotoxity (CDC). (iii) The third case is radionuclides or antitumor drug that is conjugated to antibodies and is delivered to the target tumor cells effectively. Although the present inventors previously demonstrated that the target molecule FZD10 is involved in the SS tumor growth, neither Mabs 92-13 nor 93-22 showed the neutralizing effect in vitro when added to the cell culture media (data not shown) or in vivo when injected to the tumor-bearing mice (data not shown).

Figure 7:
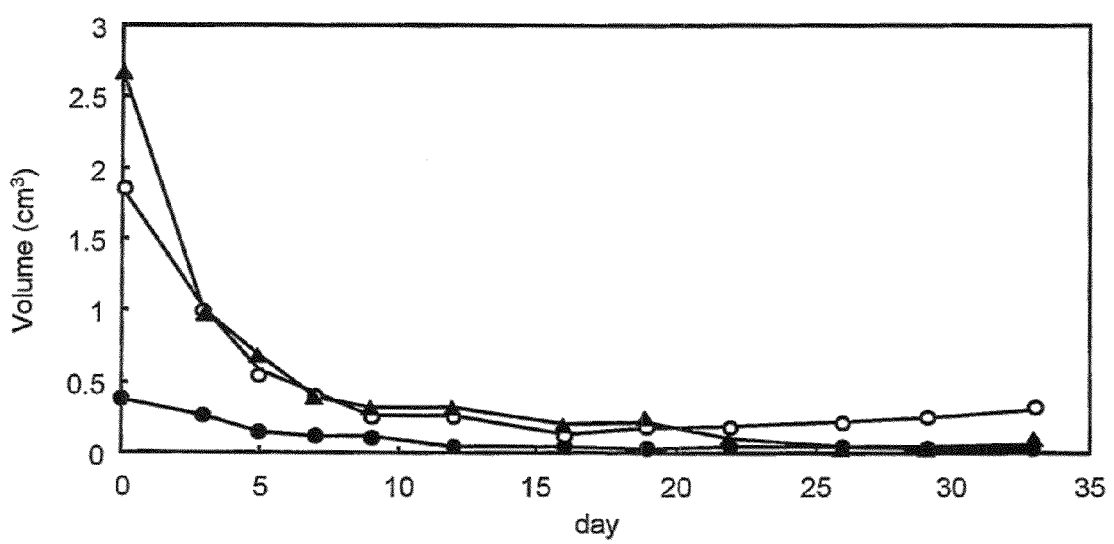
FIG. 7 shows the effect of $^{90}$Y-labeled 92-13 on tumor growth. When tumors were established (0.4-2.7 cm$^3$), mice were given a single tail vain of 100 μCi of $^{90}$Y-labeled 92-13.
Figure 8:
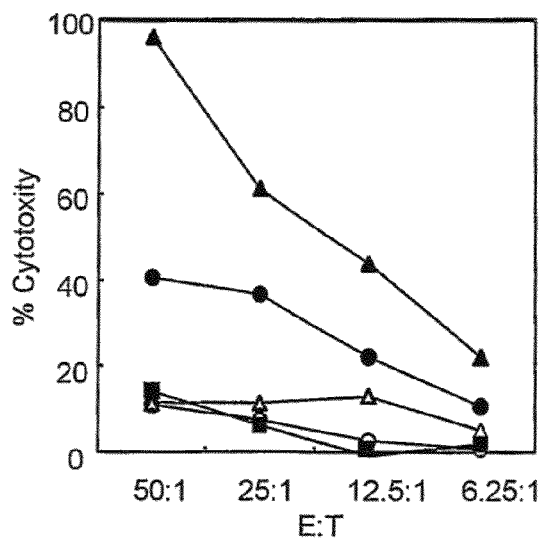
FIG. 8 shows both chimeric 92-13 and 93-22 induced ADCC specifically to the FZD10-overexpressing SYO-1 cells. 1 μg/ml of chimeric 93-22 antibody (ch93-22) or chimeric 92-13 antibody (ch92-13) at various Effector:Target ratio. PBMC from various donors were used as Effector cell; (a), (c) ADCC of chimeric 92-13 against SYO-1 cell with five healthy human PBMC donors. (b), (d) ADCC of chimeric 93-22 against LoVo cell with two healthy human PBMC donors. Quantification of cytotoxicity with LDH activity is described in (Nagayama, S., et al. Oncogene, 24, 6201-12).
Figure 8:
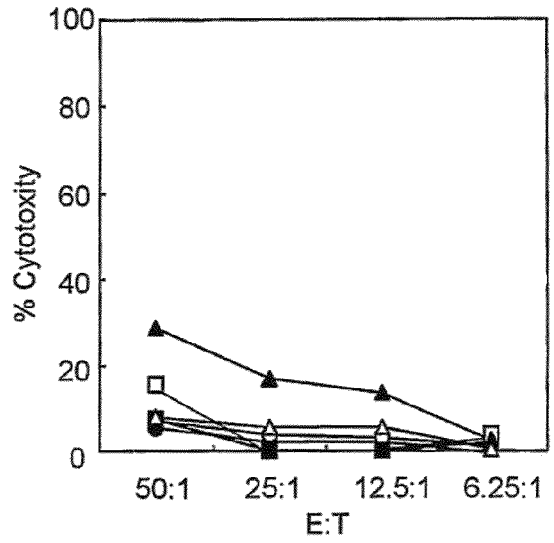
Figure 8:
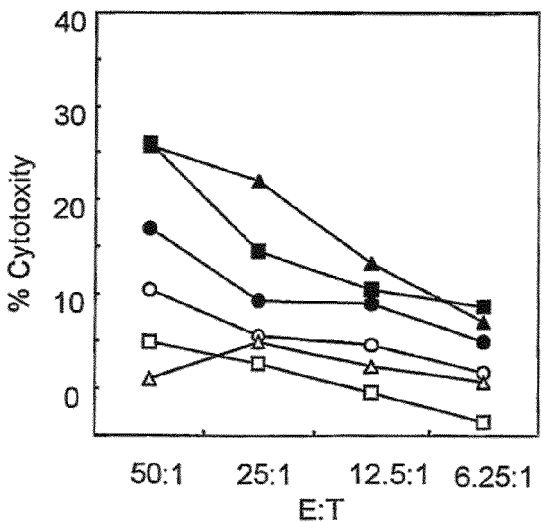
Figure 8:
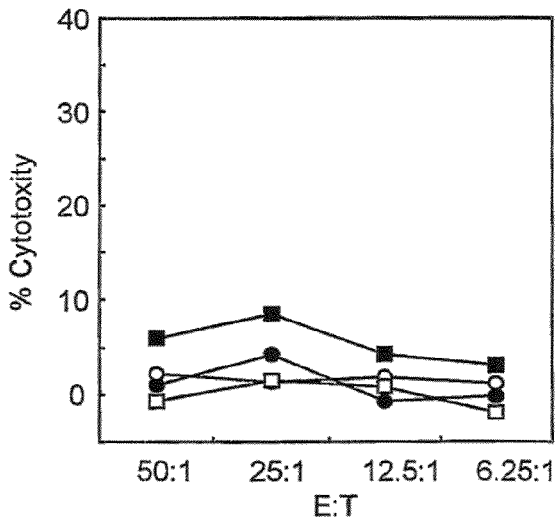

Conjugating radionuclide or anti-cancer drug to antibodies such as Zevalin (anti-CD20 antibody conjugated with $^{90}$yttrium) and Mylotarg (anti-CD33 antibody conjugated with calicheamicin), has been proven to be highly effective to confer cytotoxity to the antibodies (Wiseman, G. A. and Witzig, T. E. (2005). Cancer Biother Radiopharm, 20, 185-8; van der Velden, V. H., et al. (2001). Blood, 97, 3197-204; Carter, P. (2001). Nat Rev Cancer, 1, 118-29). Mylotarg exerts its antitumor activity by releasing antitumor drug, calicheamicin within the cancer cell after it was internalized (van der Velden, V. H., et al. (2001). Blood, 97, 3197-204). In the Examples, for therapeutic experiments, $^{90}$ yttrium-DTPA-92-13 conjugate was generated and its antitumor activity was investigated. In mouse xenograft model, tumors quickly diminished after treatment of $^{90}$yttrium-DTPA-92-13 (FIG. 7). Noticeably, the tumors including larger volume (>1 cm$^3$) of tumor showed no refraction until 34 days after administration and no strong toxicity was observed. Since anti-FZD10 antibodies 92-13 and 93-22 were likely to be effectively internalized into antigen-positive cells as shown in FIG. 6, conjugation of anti-cancer drug to both Mabs 92-13 and 93-22 is also expected to exert the high anti-cancer effect to SS cells. Referring to the effector activity, both chimeric 92-13 and 93-22 induced ADCC specifically to the FZD10-overexpressing SYO-1 cells (FIGS. 8, $a$ and $c$), but not to the FZD10-negative LoVo cells (FIGS. 8, $b$ and $d$). Particularly, chimeric 92-13 showed higher induction of cytotoxity as compared with chimeric 93-22, however, their activity depends on effector cell donor, possibly caused by polymorphism of Fc receptor. In conclusion, the present inventors successfully produced monoclonal antibodies which were able to bind specific to FZD10 on FZD10-overexpressing tumor cells in vitro and in vivo. Together, the present inventors are confident that anti-FZD10 monoclonal antibodies have great potential for development of novel drug therapies for treatment of SS and other tumors that over-express FZD10.

1. Production of an Antibody

Antibodies that can be used in the present invention specifically react against an FZD10 protein derived from an FZD10-associated disease. The term "antibody" used herein means an antibody molecule as a whole, or its fragments such as Fab fragments, F(ab')$_2$ fragments and Fv fragments, which can bind to the protein or its partial peptides as the antigen. The antibody can be either a polyclonal antibody or a monoclonal antibody. It can also be a humanized or chimeric antibody, or a single chain Fv (scFv) antibody. The antibodies (polyclonal antibodies and monoclonal antibodies) for use in the present invention can be prepared, for example, by the following process.

(1) Monoclonal antibody

Initially, an antigen is prepared for the production of an antibody useful in the present invention. FZD10 protein or its partial peptide can be used as an immunogenic protein. Alternatively, a cell expressing FZD10 protein or its partial peptide can also be used as an immunogen. The amino acid sequence of FZD10 protein used as the immunogen in the present invention and the cDNA sequence encoding the protein are publicly available in GenBank as Accession Nos. BAA84093 (SEQ ID NO: 1) and AB027464 (SEQ ID NO: 2), respectively. The FZD10 protein or its partial peptide for use as the immunogen can be synthetically prepared according to a procedure known in the art such as a solid-phase peptide synthesis process, using the available amino acid sequence information. The partial peptides of FZD10 protein include, but are not limited to, a peptide containing residues 1-225 of the amino acid sequence shown in SEQ ID NO: 1, which corresponds to the N-terminal extracellular domain of FZD10 protein (FZD10-ECD).

The protein or its partial peptide, or the cell expressing them can be prepared by using the sequence information of cDNA encoding FZD10 protein or its partial peptide according to a known gene recombination procedure. The production of the protein or its partial peptide as well as the cell expressing them according to such a gene recombination procedure will be illustrated below.

A recombinant vector for the production of protein can be obtained by linking the above cDNA sequence to an appropriate vector. A transformant can be obtained by introducing the recombinant vector for the production of protein into a host so that the target FZD10 protein or its partial peptide can be expressed.

As the vector, a phage or plasmid that is capable of autonomously replicating in a host is used. Examples of a plasmid DNA include pCAGGS, pET28, pGEX4T, pUC118, pUC119, pUC18, pUC19, and other plasmid DNAs derived from *Escherichia coli*; pUB110, pTP5, and other plasmid DNAs derived from *Bacillus subtilis*; and YEp13, YEp24, YCp50 and other plasmid DNAs derived from yeast. Examples of a phage DNA include lambda phages such as λgt11 and λZAP. In addition, animal virus vectors such as retrovirus vector and vaccinia virus vector can be used, and insect virus vectors such as baculovirus vector can also be used.

The DNA encoding the FZD10 protein or its partial peptide (hereinafter referred to as FZD10 DNA) is inserted into the vector, for example, by the following method. In this method, purified DNA is cleaved by an appropriate restriction enzyme and inserted into a restriction enzyme site or a multi-cloning site of an appropriate vector DNA to ligate into the vector.

In addition to a promoter and the FZD10 DNA, any of enhancers and other cis elements, splicing signals, poly A addition signals, selective markers, ribosome binding site (RBS), and other elements can be ligated into the recombinant vector for the production of protein for use in mammalian cells, if desired.

For ligating the DNA fragment to the vector fragment, a known DNA ligase can be used. The DNA fragment and the vector fragment are annealed and ligated, thereby producing a recombinant vector for the production of a protein.

The host for use in transformation is not specifically limited as long as it allows the FZD10 protein or its partial peptide to be expressed therein. Examples of the host include bacteria, for example, *E. coli*, and *Bacillus*; yeast, for example, *Saccharomyces cerevisiae*; animal cells, for example, COS cells, Chinese Hamster Ovary (CHO) cells, and insect cells.

For example, when a bacterium is used as the host, the recombinant vector for the protein production should preferably be capable of autonomously replicating in the host bacterium and comprise a promoter, a ribosome binding site, the FZD10 DNA, and a transcription termination sequence. The recombinant vector may further comprise a gene for regulating the promoter. An example of *Escherichia coli* includes *Escherichia coli* BRL, and an example of *Bacillus* is *Bacillus subtilis*. Any promoter that can be expressed in the host such as *Escherichia coli* can be used herein.

The recombinant vector can be introduced into the host bacterium by any procedures known in the art. Such procedures include, for example, a method using calcium ions and an electroporation. When yeast cell, an animal cell, or an insect cell is used as the host, a transformant can be produced according to a known procedure in the art, and then the FZD10 protein or its partial peptide can be produced in the host (transformant).

The FZD10 protein or its partial peptide for use as the immunogen in the present invention can be obtained from a culture of the above-generated transformant. The "culture" refers to any of culture supernatant, cultured cells, cultured microorganisms, and homogenates thereof. The transformant is cultured in a culture medium by a conventional process of culturing a host.

The culture medium for culturing the transformant obtained by using *Escherichia coli*, yeast, or other microorganisms as the host can be either a natural medium or a synthetic medium, as long as it comprises a carbon source, nitrogen source, inorganic salts, and other components utilizable by the microorganism and enables the transformant to grow efficiently.

The transformant is generally cultured by shaking culture or aeration culture with stirring under aerobic conditions at 25° C. to 37° C. for 3 to 6 hours. During culturing, pH is held at a level near neutrality by adjustment with, for example, an inorganic or organic acid, and an alkaline solution. During culturing, antibiotics such as ampicillin or tetracycline may be added to the medium according to the selective marker inserted into the recombinant expression vector, if necessary.

After culturing, when the FZD10 protein or its partial peptide is produced within the microorganism or cell, the protein or its partial peptide is extracted by homogenizing the microorganism or cell. When the FZD10 protein or its partial peptide is secreted from the microorganism or cell, the culture medium is used as is, or debris of the microorganism or cell is removed from the culture medium, for example, by centrifugation. Thereafter, the FZD10 protein or its partial peptide can be isolated from the culture and purified by a conventional biochemical method for the isolation and purification of proteins, such as ammonium sulfate precipitation, gel chromatography, ion-exchange chromatography, and affinity chromatography, either individually or in combination.

Whether or not the FZD10 protein or its partial peptide has been obtained can be confirmed, for example, by SDS polyacrylamide gel electrophoresis.

Next, the obtained FZD10 protein or its partial peptide, or the transformant is dissolved in a buffer to prepare an immunogen. Where necessary, an adjuvant can be added thereto for effective immunization. Such adjuvants include, for example, commercially available Freund's complete adjuvant and Freund's incomplete adjuvant. Any of these adjuvants can be used alone or in combination.

The immunogen so prepared is administered to a mammal such as a rabbit, rat, or mouse. The immunization is performed mainly by intravenous, subcutaneous, or intraperitoneal injection. The interval of immunization is not specifically limited and the mammal is immunized one to 3 times at intervals ranging from several days to weeks. Antibody-producing cells are collected 1 to 7 days after the last immunization. Examples of the antibody-producing cells include spleen cells, lymph node cells, and peripheral blood cells.

To obtain a hybridoma, an antibody-producing cell and a myeloma cell are fused. As the myeloma cell to be fused with the antibody-producing cell, a generally available established cell line can be used. Preferably, the cell line used should have drug selectivity and properties such that it can not survive in a HAT selective medium (containing hypoxanthine, aminopterin, and thymidine) in unfused form and can survive only when fused with an antibody-producing cell. Possible myeloma cells include, for example, mouse myeloma cell lines such as P3×63-Ag.8.U1 (P3U1), and NS-I.

Next, the myeloma cell and the antibody-producing cell are fused. For the fusion, these cells are mixed, preferably at the ratio of the antibody-producing cell to the myeloma cell of 5:1, in a culture medium for animal cells which does not contain serum, such as DMEM and RPMI-1640 media, and fused in the presence of a cell fusion-promoting agent such as polyethylene glycol (PEG). The cell fusion may also be carried out by using a commercially available cell-fusing device using electroporation.

Then, the hybridoma is picked up from the cells after above fusion treatment. For example, a cell suspension is appropriately diluted with, for example, the RPMI-1640 medium containing fetal bovine serum and then plated onto a microtiter plate. A selective medium is added to each well, and the cells are cultured with appropriately replacing the selective medium. As a result, the cells that grow about 30 days after the start of culturing in the selective medium can be obtained as the hybridoma.

The culture supernatant of the growing hybridoma is then screened for the presence of an antibody that reacts with the FZD10 protein or its partial peptide. The screening of hybridoma can be performed according to a conventional procedure, for example, using enzyme-linked immunosorbent assay (ELISA), enzyme immunoassay (EIA) or radioimmunoassay (RIA). The fused cells are cloned by the limiting dilution to establish a hybridoma, which produces the monoclonal antibody of interest.

The monoclonal antibody can be collected from the established hybridoma, for example, by a conventional cell culture method or by producing the ascites. If necessary, the antibody can be purified in the above-described antibody collecting method according to a known procedure such as ammonium sulfate precipitation, ion-exchange chromatography, gel filtration, affinity chromatography, or a combination thereof.

The globulin type of the monoclonal antibodies useful in the present invention is not specifically limited, as long as they are capable of specifically binding to the FZD10 protein and can be any of IgG, IgM, IgA, IgE, and IgD. Among them, IgG and IgM are preferred.

In the present invention, murine monoclonal antibodies 93-22 and 92-13 are successfully established and preferably used. The hybridoma clone 93-22 producing mouse monoclonal antibody 93-22 was deposited by Shuichi Nakatsuru internationally at the IPOD International Patent Organism Depository of the National Institute of Advanced Industrial Science and Technology (AIST Tsukuba Central 6, 1-1, Higashi 1-chome, Tsukuba-shi, Ibaraki-Ken, 305-8566 Japan) as of Jun. 14, 2006 under the deposit number of FERM BP-10620. Also, hybridoma clone 92-13 producing mouse monoclonal antibody 92-13 was deposited by Shuichi Nakatsuru internationally at the IPOD International Patent Organism Depository of the National Institute of AIST as of Jun. 28, 2006 under the deposit number of FERM BP-10628. The monoclonal antibody produced by the hybridoma may be preferably used in the present invention. All restrictions imposed on the availability to the public of the deposited materials FERM BP-10620 and FERM BP-10628 will be irrevocably removed upon granting a patent for the same.

In the present invention, a recombinant-type monoclonal antibody may also be used, which can be produced by cloning an antibody gene from the hybridoma, integrating the antibody gene into a suitable vector, introducing the vector into a host, and producing the antibody from the host according to a conventional genetic recombination technique (see, for example, Vandamme, A. M. et al., Eur. J. Biochem. (1990) 192, 767-75).

More specifically, mRNA encoding variable (V) region of the anti-FZD10 mouse monoclonal antibody is isolated from the antibody-producing hybridoma (for example, those described above). The isolation of the mRNA is performed by preparing a total RNA by any known method, such as guanidium ultracentrifugation method (Chirgwin, J. M. et al., Biochemistry (1979) 18, 5294-9) and AGPC method (Chomczynski, P. et al., Anal. Biochem. (1987) 162, 156-9), and then producing the desired mRNA from the total RNA using mRNA Purification Kit (Pharmacia) or the like. Alternatively, the mRNA may also be prepared directly using QuickPrep mRNA Purification Kit (Pharmacia).

Next, cDNA for the antibody V-region is synthesized from the mRNA with a reverse transcriptase. The synthesis of the cDNA may be performed using a commercially available kit, for example, Gene Racer™ Kit (Invitrogen). The cDNA may also be synthesized or amplified by 5'-RACE method (Frohman, M. A. et al., Proc. Natl. Acad. Sci. USA (1988) 85, 8998-9002; Belyaysky, A. et al., Nucleic Acids Res. (1989) 17, 2919-32) using 5'-Ampli FINDER RACE Kit (Clontech) in combination with a PCR method.

The amino acid sequences of H chain and L chain of mouse monoclonal antibody 92-13 are shown in SEQ ID NO: 57 and 59, respectively (encoded by the nucleotide sequence as shown in SEQ ID NO: 58 and 60, respectively). The amino acid sequences of H chain and L chain of mouse monoclonal antibody 93-22 are shown in SEQ ID NO: 61 and 63, respectively (encoded by the nucleotide sequence as shown in SEQ ID NO: 62 and 64, respectively). Based on the sequence information, primers used for amplifying the H chain or L chain of mouse monoclonal antibody of interest can be designed using a conventional method.

A DNA fragment of interest is isolated and purified from the resultant PCR product and then ligated to a vector DNA to obtain a recombinant vector. The recombinant vector is introduced into a host such as E. coli, and a colony containing a desired recombinant vector is selected. The nucleotide sequence of the DNA of interest in the recombinant vector is confirmed using, for example, an automated sequencer.

Once DNA encoding the anti-FZD10 antibody V-region is obtained, the DNA is integrated into an expression vector containing DNA encoding the antibody constant (C) region.

For the production of the anti-FZD10 antibody used in the present invention, the antibody gene is integrated into an expression vector so that the antibody gene can be expressed under the control of expression control elements (e.g., enhancer, promoter). A host cell is transformed with the expression vector to express the antibody.

In the expression of the antibody gene, DNA encoding heavy (H) chain and DNA encoding light (L) chain of the antibody may be integrated into separate expression vectors, and then a host cell is co-transformed with the resultant recombinant expression vectors. Alternatively, both DNA encoding H-chain and DNA encoding L-chain of the antibody may be integrated together into a single expression vector, and then a host cell is transformed with the resultant recombinant expression vector (for example, WO 94/11523).

The antibody gene can be expressed by known methods. For the expression in a mammalian cell, a conventional useful promoter, the antibody gene to be expressed and a poly(A) signal (located downstream to the 3' end of the antibody gene) may be operably linked. For example, as the useful promoter/enhancer system, a human cytomegalovirus immediate early promoter/enhancer system may be used.

Other promoter/enhancer systems, for example, those derived from viruses (e.g., retrovirus, polyoma virus, adenovirus and simian virus 40 (SV40)) and those derived from mammalian cells (e.g., human elongation factor 1 alpha (HEF1 alpha)), may also be used for the expression of the antibody in the present invention.

When SV40 promoter/enhancer system is used, the gene expression may be performed readily by the method of Mulligan et al. (Nature (1979) 277, 108-14). When HEF1 alpha promoter/enhancer system is used, the gene expression may be performed readily by the method of Mizushima et al. (Nucleic Acids Res. (1990) 18, 5322).

For the expression in *E. coli*, a conventional useful promoter, a signal sequence for secreting the antibody of interest and the antibody gene may be operably linked. As the promoter, lacZ promoter or araB promoter may be used. When lacZ promoter is used, the gene expression may be performed by the method of Ward et al. (Nature (1098) 341, 544-6; FASEB J. (1992) 6, 2422-7), while when araB promoter is used, the gene expression may be performed by the method of Better et al. (Science (1988) 240, 1041-3).

With respect to the signal sequence for secretion of the antibody, when the antibody of interest is intended to be secreted in a periplasmic space of the *E. coli*, pelB signal sequence (Lei, S. P. et al., J. Bacteriol. (1987) 169, 4379-83) may be used. The antibody secreted into the periplasmic space is isolated and then refolded so that the antibody takes an appropriate configuration.

The replication origin derived from viruses (e.g., SV40, polyoma virus, adenovirus, bovine papilloma virus (BPV)) or the like may be used. In order to increase the gene copy number in the host cell system, the expression vector may further contain a selective marker gene, such as an aminoglycoside phosphotranferase (APH) gene, a thymidine kinase (TK) gene, an *E. coli* xanthine-guanine phosphoribosyltransferase (Ecogpt) gene and a dihydrofolate reductase (dhfr) gene.

For the production of the antibody used in the present invention, any expression system including eukaryotic and prokaryotic cell systems may be used. The eukaryotic cell includes established cell lines of animals (e.g., mammals, insects, molds and fungi, yeast). The prokaryotic cell includes bacterial cells such as *E. coli* cells. It is preferable that the antibody used in the present invention be expressed in a mammalian cell, such as a CHO, COS, myeloma, BHK, Vero and HeLa cell.

Next, the transformed host cell is cultured in vitro or in vivo to produce the antibody of interest. The cultivation of the host cell may be performed by any known method. The culture medium that can be used herein may be DMEM, MEM, RPMI 1640 or IMDM medium. The culture medium may contain a serum supplement, such as fetal calf serum (FCS).

In the production of the recombinant antibody, besides the above-mentioned host cells, a transgenic animal may also be used as a host. For example, the antibody gene is inserted into a predetermined site of a gene encoding a protein inherently produced in the milk of an animal (e.g., beta-casein) to prepare a fusion gene. A DNA fragment containing the antibody gene-introduced fusion gene is injected into an embryo of a non-human animal, and the embryo is then introduced into a female animal. The female animal having the embryo therein bears a transgenic non-human animal. The antibody of interest is secreted in the milk from the transgenic non-human animal or a progeny thereof. For the purpose of increasing the amount of the antibody-containing milk, an appropriate hormone may be administered to the transgenic animal (Ebert, K. M. et al., Bio/Technology (1994) 12, 699-702).

The antibody expressed and produced as described above may be isolated from the cells or the host animal body and purified. The isolation and purification of the antibody used in the present invention may be performed on an affinity column. Other methods conventionally used for the isolation and purification of an antibody may be also be used; thus the method is not particularly limited. For example, various chromatographies, filtration, ultrafiltration, salting out and dialysis may be used singly or in combination to isolate and purify the antibody of interest (Antibodies A Laboratory Manual. Ed. Harlow, David Lane, Cold Spring Harbor Laboratory, 1988).

(2) Chimeric Antibody and Humanized Antibody

In the present invention, an artificially modified recombinant antibody may be used, including a chimeric antibody and a humanized antibody. These modified antibodies can be prepared by any known method. For example, techniques developed for the production of "chimeric antibodies" (Morrison et al., 1984, Proc. Natl. Acad. Sci., 81: 6851-5; Neuberger et al., 1984, Nature, 312: 604-8; Takeda et al., 1985, Nature, 314: 452-4) can be used. A chimeric antibody is a molecule in which different portions are derived from different animal species, such as those having a variable region derived from a murine mAb and a human immunoglobulin constant region, e.g., "humanized antibodies".

A chimeric antibody according to the present invention can be prepared by ligating the DNA encoding the antibody V-region to DNA encoding a human antibody C-region, integrating the ligation product into an expression vector, and introducing the resultant recombinant expression vector into a host to produce the chimeric antibody.

A humanized antibody is also referred to as "reshaped human antibody", in which the complementarity determining regions (CDRs) of an antibody of a non-human mammal (e.g., a mouse) are grafted to those of a human antibody. The general genetic recombination procedure for producing such humanized antibody is also known (for example, EP 125023; WO 96/02576).

Specifically, a DNA sequence in which mouse antibody CDRs are ligated through framework regions (FRs) is designed, and synthesized by a PCR method using several oligonucleotides as primers which were designed to have regions overlapping to the terminal regions of the CDRs and the FRs. The resultant DNA is ligated to DNA encoding the human antibody C-region, and the ligation product is integrated into an expression vector. The resultant recombinant expression vector is introduced into a host, thereby producing the humanized antibody (for example, WO 96/02576).

The FRs ligated through the CDRs are selected so that the CDRs can form a functional antigen binding site. If necessary, an amino acid(s) in the FRs of the antibody V-region may be replaced so that the CDRs of the reshaped human antibody can form an appropriate antigen binding site (Sato, K. et al., Cancer Res. (1993) 53, 851-6).

The chimeric antibody is composed of V-regions derived from a non-human mammal antibody and C-regions derived from a human antibody. The humanized antibody is composed of CDRs derived from a non-human mammal antibody and FRs and C-regions derived from a human antibody. The humanized antibody may be useful for clinical use, because the antigenicity of the antibody against a human body is reduced.

A specific example of a chimeric antibody or a humanized antibody used in the present invention is an antibody in which the CDRs are derived from the mouse monoclonal antibody 92-13 or an antibody in which the CDRs are derived from the mouse monoclonal antibody 93-22. The method for producing such chimeric antibodies and humanized antibodies are described below.

To clone DNA comprising a nucleotide sequence coding for V region of the anti-FZD10 mouse monoclonal antibody, mRNA can be isolated from hybridomas and each cDNA in the V regions of L and H chains can be synthesized with the use of a reverse transcriptase as described above. In the synthesis of cDNA, Oligo-dT primer or other appropriate primer which hybridizes to L or H chain C region may be used. For example, but not limited to, CH1 (IgG2a) primer having the nucleotide sequence as shown in SEQ ID NO: 3 for H chain V region and CL1 (kappa) primer having the nucleotide sequence as shown in SEQ ID NO: 4 for L chain V region can be used.

Amplification of cDNA of both L and H chains can be performed by PCR (polymerase chain reaction) using a commercially available kit (for example, GeneRacer™ kit from Invitrogen) or using a known method including 5'-RACE method (Frohman, M. A. et al., Proc. Natl. Acad. Sci. USA, 85, 8998-9002, 1988; Belyaysky, A. et al., Nucleic Acids Res., 17, 2919-32, 1989).

The specific primers for amplifying DNA for V regions of the mouse monoclonal antibody 92-13 include primers having the nucleotide sequences shown in SEQ ID NOs: 5 and 6 for H chain V region and primers having the nucleotide sequences shown in SEQ ID NOs: 7 and 8 for L chain V region. Using these primers, a DNA encoding H chain V region having an amino acid sequence as shown in SEQ ID NO: 13 and a DNA encoding L chain V region having an amino acid sequence as shown in SEQ ID NO: 21 can be amplified. The specific primers for amplifying DNA for V regions of the mouse monoclonal antibody 93-22 include primers having the nucleotide sequences shown in SEQ ID NOs: 53 and 54 for H chain V region and primers having the nucleotide sequences shown in SEQ ID NOs: 55 and 56 for L chain V region. Using these primers, a DNA encoding H chain V region having an amino acid sequence as shown in SEQ ID NO: 29 and a DNA encoding L chain V region having an amino acid sequence as shown in SEQ ID NO: 37 can be amplified.

Then, the amplified products are subjected to agarose gel electrophoresis according to conventional procedures, and DNA fragments of interest are excised, recovered, purified and ligated to a vector DNA.

The obtained DNA and vector DNA can be ligated using a known ligation kit to construct a recombinant vector. A vector DNA may be prepared in a known method: J. Sambrook, et al., "Molecular Cloning", Cold Spring Harbor Laboratory Press, 1989. The vector DNA is digested with restriction enzyme(s), and the nucleotide sequence of a desired DNA can be determined by a known method or using an automated sequencer.

Once DNA fragments coding for L and H chain V regions of mouse monoclonal antibody (hereinafter L or H chain of an antibody may sometimes be referred to as "mouse L or H chain" for mouse antibodies and "human L or H chain" for human antibodies) are cloned, the DNAs coding for mouse V regions and DNAs coding for human antibody constant regions are ligated and expressed to yield chimeric antibodies.

A standard method for preparing chimeric antibodies involves ligating a mouse leader sequence and V region sequence present in a cloned cDNA to a sequence coding for a human antibody C region already present in an expression vector of a mammalian cell. Alternatively, a mouse leader sequence and V region sequence present in a cloned cDNA are ligated to a sequence coding for a human antibody C region followed by ligation to a mammalian cell expression vector.

The polypeptide comprising human antibody C region can be any of H or L chain C regions of human antibodies, including, for example, C gamma 1, C gamma 2, C gamma 3 or C gamma 4 for human H chains or C lambda or C kappa for L chains.

To prepare a chimeric antibody, two expression vectors are first constructed; that is, an expression vector containing DNAs coding for mouse L chain V region and human L chain C region under the control of an expression control element such as an enhancer/promoter system, and an expression vector containing DNAs coding for mouse H chain V region and human H chain C region under the control of an expression control element such as an enhancer/promoter system, are constructed. Then, host cells such as mammalian cells (for example, COS cell) are cotransformed with these expression vectors and the transformed cells are cultivated in vitro or in vivo to produce a chimeric antibody: see, for example, WO91/16928.

Alternatively, the mouse leader sequence present in the cloned cDNA and DNAs coding for mouse L chain V region and human L chain C region as well as the mouse leader sequence and DNAs coding for mouse H chain V region and human H chain C region are introduced into a single expression vector (see, for example, WO94/11523) and said vector is used to transform a host cell; then, the transformed host is cultured in vivo or in vitro to produce a desired chimeric antibody.

The vector for the expression of H chain of a chimeric antibody can be obtained by introducing cDNA comprising a nucleotide sequence coding for mouse H chain V region (hereinafter referred to also as "cDNA for H chain V region") into a suitable expression vector containing the genomic DNA comprising a nucleotide sequence coding for H chain C region of human antibody (hereinafter referred to also as "genomic DNA for H chain C region") or cDNA coding for said region (hereinafter referred to also as "cDNA for H chain C region"). The H chain C region includes, for example, C gamma 1, C gamma 2, C gamma 3 or C gamma 4 regions.

The expression vectors having the genomic DNA coding for H chain C region, in particular, those coding for C gamma 1 region, include, for example, HEF-PMh-g gamma (WO92/19759) and DHER-INCREMENT E-RVh-PM1-f (WO92/19759). Alternatively, human constant region library can be prepared using cDNA from human PBMC (peripheral blood mononuclear cells) as described previously (Liu, A. Y. et al., Proc. Natl. Acad. Sci. USA, Vol. 84, 3439-43, 1987; Reff, M. E. et al., Blood, Vol. 83, No. 2, 435-45, 1994).

When cDNA coding for mouse H chain V region is inserted into these expression vectors, an appropriate nucleotide sequence can be introduced into said cDNA through PCR method. For instance, PCR may be effected using a PCR primer which is designed such that said cDNA has a recognition sequence for a suitable restriction enzyme at its 5'-end and Kozak consensus sequence immediately before the initiation codon thereof so as to improve the transcription efficiency, as well as a PCR primer which is designed such that said cDNA has a recognition sequence for a suitable restriction enzyme at its 3'-end and a splice donor site for properly splicing the primary transcription products of the genomic DNA to give a mRNA, to introduce these appropriate nucleotide sequences into the expression vector.

The thus constructed cDNA coding for mouse H chain V region is treated with a suitable restriction enzyme(s), then it is inserted into said expression vector to construct a chimeric H chain expression vector containing the genome DNA coding for H chain C region (C gamma 1 region).

The thus constructed cDNA coding for mouse H chain V region is treated with a suitable restriction enzyme(s), ligated to cDNA coding for said H chain C region C gamma 1, and inserted into an expression vector such as pQCXIH (Clontech) to construct an expression vector containing the cDNA coding for a chimeric H chain.

The vector for the expression of L chain of a chimeric antibody can be obtained by ligating a cDNA coding for mouse L chain V region and a genomic DNA or cDNA coding for L chain C region of a human antibody and introducing into a suitable expression vector. The L chain C region includes, for example, kappa chain and lambda chain.

When an expression vector containing cDNA coding for mouse L chain V region is constructed, appropriate nucleotide sequences such as a recognition sequence or Kozak consensus sequence can be introduced into said expression vector through PCR method.

The entire nucleotide sequence of cDNA coding for human L lambda chain C region may be synthesized by a DNA synthesizer and constructed through PCR method. The human L lambda chain C region is known to have at least 4 different isotypes and each isotype can be used to construct an expression vector.

The constructed cDNA coding for human L lambda chain C region and the above constructed cDNA coding for mouse L chain V region can be ligated between suitable restriction enzyme sites and inserted into an expression vector such as pQCXIH (Clontech), to construct an expression vector containing cDNA coding for a L lambda chain of a chimeric antibody.

The DNA coding for human L kappa chain C region to be ligated to the DNA coding for mouse L chain V region can be constructed from, for example, HEF-PM1k-gk containing the genomic DNA (see WO92/19759). Alternatively, human constant region library can be prepared using cDNA from human PBMC (peripheral blood mononuclear cells) as described previously (Liu, A. Y. et al., Proc. Natl. Acad. Sci. USA, Vol. 84, 3439-43, 1987; Reff, M. E. et al., Blood, Vol. 83, No. 2, 435-45, 1994).

Recognition sequences for suitable restriction enzymes can be introduced, through PCR method, into 5'- and 3'-ends of DNA coding for L kappa chain C region, and the DNA coding for mouse L chain V region as constructed above and the DNA coding for L kappa chain C region can be ligated to each other and inserted into an expression vector such as pQCXIH (Clontech) to construct an expression vector containing cDNA coding for L kappa chain of a chimeric antibody.

In order to make a humanized antibody in which CDR of a mouse monoclonal antibody is grafted to a human antibody, it is desirable that there exists a high homology between FR of the mouse monoclonal antibody and FR of the human antibody. Accordingly, a comparison is made between V regions of H and L chains of mouse anti-FZD10 monoclonal antibody and the V regions of all the known antibodies whose structures have been elucidated with the use of Protein Data Bank. Further, they are simultaneously compared with the human antibody subgroups (HSG: Human subgroup) classified by Kabat et al. based on the length of antibody FR, the homology of amino acids, and the like: Kabat, E. A. et al, US Dep, Health and Human Services, US Government Printing Offices, 1991.

The first step for designing DNA coding for a humanized antibody V region is to select a human antibody V region as a basis for the designing. For example, FR of a human antibody V region having a homology of higher than 80% with FR of a mouse antibody V region can be used in the production of a humanized antibody.

In the humanized antibody, the C region and the framework (FR) regions of the V region of said antibody are originated from human and the complementarity determining regions (CDR) of the V region are originated from mouse. A polypeptide comprising the V region of the humanized antibody can be produced in the manner called CDR-grafting by PCR method so long as a DNA fragment of a human antibody would be available as a template. The "CDR-grafting" refers to a method wherein a DNA fragment coding for a mouse-derived CDR is made and replaced for the CDR of a human antibody as a template.

If a DNA fragment of a human antibody to be used as a template is not available, a nucleotide sequence registered in a database may be synthesized in a DNA synthesizer and a DNA for a V region of a humanized antibody can be produced by the PCR method. Further, when only an amino acid sequence is registered in the database, the entire nucleotide sequence may be deduced from the amino acid sequence on the basis of knowledge on the codon usage in antibodies as reported by Kabat, E. A. et al. in US Dep. Health and Human Services, US Government Printing Offices, 1991. This nucleotide sequence is synthesized in a DNA synthesizer and a DNA of a humanized antibody V region can be prepared by PCR method and introduced into a suitable host followed by expression thereof to produce the desired polypeptide.

General procedures of CDR-grafting by PCR method are described below when a DNA fragment of a human antibody as a template is available.

First, mouse derived DNA fragments corresponding to respective CDRs are synthesized. CDRs 1 to 3 are synthesized on the basis of the nucleotide sequences of the previously cloned mouse H and L chain V regions. For example, when a humanized antibody is produced based on the mouse monoclonal antibody 92-13, CDR sequences of H chain V region can be the amino acid sequences as shown in SEQ ID NOs: 15 (VH CDR1), 17 (VH CDR2) and 19 (VH CDR3); and CDR sequences of L chain V region can be the amino acid sequences as shown in SEQ ID NOs: 23 (VL CDR1), 25 (VL CDR2) and 27 (VL CDR3). When a humanized antibody is produced based on the mouse monoclonal antibody 93-22, CDR sequences of H chain V region can be the amino acid sequences as shown in SEQ ID NOs: 31 (VH CDR1), 33 (VH CDR2) and 35 (VH CDR3); and CDR sequences of L chain V region can be the amino acid sequences as shown in SEQ ID NOs: 39 (VL CDR1), 41 (VL CDR2) and 43 (VL CDR3).

The DNA for H chain V region of a humanized antibody may be ligated to DNA for any human antibody H chain C region, for example, human H chain C gamma 1 region. As mentioned above, the DNA for H chain V region may be treated with a suitable restriction enzyme and ligated to a DNA coding for a human H chain C region under an expression control element such as an enhancer/promoter system to make an expression vector containing DNAs for a humanized H chain V region and a human H chain C region.

The DNA for L chain V region of a humanized antibody may be ligated to DNA for any human antibody L chain C region, for example, human L chain C lambda region. The DNA for L chain V region may be treated with a suitable restriction enzyme and ligated to a DNA coding for a human L lambda chain C region under an expression control element such as an enhancer/promoter system to make an expression vector containing DNAs coding for a humanized L chain V region and a human L lambda chain C region.

The DNA coding for H chain V region of a humanized antibody and a human H chain C region and the DNA coding for a humanized L chain V region and human L chain C region may also be introduced into a single expression vector such as that disclosed in WO94/11523, said vector may be used to transform a host cell, and the transformed host may be cultivated in vivo or in vitro to produce a desired humanized antibody.

To produce a chimeric or humanized antibody, two expression vectors as above mentioned should be prepared. Thus, with respect to a chimeric antibody, an expression vector comprising a DNA coding for a mouse H chain V region and a human H chain C region under the control of an expression control element such as an enhancer/promoter, and an expression vector comprising a DNA coding for a mouse L chain V region and a human L chain C region under the control of an expression control element are constructed. With respect to a humanized antibody, an expression vector comprising a DNA coding for a humanized H chain V region and a human H chain C region under the control of an expression control element, and an expression vector comprising a DNA coding for a humanized L chain V region and a human L chain C region under the control of an expression control element are constructed.

Then, a host cell such as a mammalian cell (for example, COS cell) may be cotransformed with these expression vectors and the resulting transformed cell may be cultured in vitro or in vivo to produce the chimeric or humanized antibody (see, for example, WO91/16928).

Alternatively, a DNA coding for H chain V and C regions and a DNA coding for L chain V and C regions may be ligated to a single vector and transformed into a suitable host cell to produce an antibody. Thus, in the expression of a chimeric antibody, a DNA coding for a mouse leader sequence present in the cloned cDNA, a mouse H chain V region and a human H chain C region as well as a DNA coding for a mouse leader sequence, a mouse L chain V region and a human L chain C region, can be introduced into a single expression vector such as one disclosed in e.g. WO94/11523. In the expression of a humanized antibody, a DNA coding for a humanized H chain V region and a human H chain C region and a DNA coding for a humanized L chain V region and a human L chain C region may be introduced into a single expression vector such as one disclosed in e.g. WO94/11523. Such a vector is used to transform a host cell and the transformed host is cultured in vivo or in vitro to produce a chimeric or humanized antibody of interest.

Any expression system may be used to produce the chimeric or humanized antibody against FZD10 protein according to the present invention. For example, eukaryotic cells include animal cells such as established mammalian cell lines, fungal cells, and yeast cells; prokaryotic cells include bacterial cells such as *Escherichia coli*. Preferably, the chimeric or humanized antibody of the present invention is expressed in a mammalian cell such as COS or CHO cell.

Any conventional promoters useful for the expression in mammalian cells may be used. For example, human cytomegalovirus (HCMV) immediate early promoter is preferably used. In addition, promoters for gene expression in mammalian cells may include virus promoters, such as those of retrovirus, polyoma virus, adenovirus and simian virus (SV) 40, and mammalian cell derived promoters, such as those of human polypeptide chain elongation factor-1 alpha (HEF-1 alpha). For example, SV40 promoter may be readily used according to Mulligan et al. method (Nature, 277, 108-14, 1979); Mizushima, S. et al. method (Nucleic Acids Research, 18, 5322, 1990) may be easily used with HEF-1 alpha promoter.

Replication origin includes those derived from SV40, polyoma virus, adenovirus or bovine papilloma virus (BPV). Further, the expression vector may comprise a gene for phosphotransferase APH(3') II or I (neo), thymidine kinase (TK), *E. coli* xanthine-guanine phosphoribosyltransferase (Ecogpt) or dihydrofolate reductase (DHFR) as a selective marker for increasing the gene copy number in a host cell system.

The chimeric or humanized antibody of interest which is thus produced by culturing the transformant transformed with a DNA coding for the chimeric or humanized antibody may be isolated from the cell and then purified.

The isolation and purification of the chimeric or humanized antibody of interest may be carried out by using a protein A agarose column, but may also be performed by any methods used in isolation and purification of a protein and thus is not limited. For instance, a chromatography, ultrafiltration, salting out and dialysis may optionally be selected or combined to isolate and purify the chimeric or humanized antibody.

After isolating the chimeric antibody or humanized antibody, the concentration of the resulting purified antibody can be determined by ELISA.

The determination of the antigen-binding activity or other activities including binding activity to a normal cell of the chimeric antibody or humanized antibody may be performed by any known methods (Antibodies A Laboratory Manual, Ed. Harlow, David Lane, Cold Spring Harbor Laboratory, 1988).

As the method for the determination of the antigen-binding activity of an antibody, techniques such as ELISA (enzyme-linked immunosorbent assay), EIA (enzyme immunoassay), RIA (radioimmunoassay) or fluorescent assay may be employed.

(3) Antibody Fragment and Modified Antibody

The antibody used in the present invention may be any fragment thereof or a modified antibody, as long as it can bind to FZD10 protein and inhibit its activity. For example, the fragment of the antibody includes Fab, F(ab')$_2$, Fv, or a single chain Fv (scFv) composed of a H-chain Fv fragment or a L-chain Fv fragment linked together through a suitable linker. Specifically, such antibody fragments can be produced by cleaving the antibody with an enzyme (e.g., papain, pepsin) into antibody fragments, or by constructing a gene encoding the antibody fragment and inserting the gene into an expression vector and introducing the resultant recombinant expression vector into a suitable host cell, thereby expressing the antibody fragment (see, for example, Co, M. S., et al., J. Immunol. (1994), 152, 2968-76; Better, M. & Horwitz, A. H., Methods in Enzymology (1989), 178, 476-96, Academic Press, Inc.; Pluckthun, A. & Skerra, A., Methods in Enzymology (1989) 178, 497-515, Academic Press, Inc.; Lamoyi, E., Methods in Enzymology (1989) 121, 652-63; Rousseaux, J. et al., Methods in Enzymology (1989) 121, 663-9; and Bird, R. E. et al., Trends Biotechnol. (1991) 9, 132-7). Alternatively, Fab expression libraries may be constructed (Huse et al., 1989, Science, 246: 1275-81) to allow rapid and easy identification of monoclonal Fab fragments with the desired specificity.

A scFv can be produced by ligating the H-chain V-region to the L-chain V-region through a linker, preferably a peptide linker (Huston, J. S. et al., Proc. Natl. Acad. Sci. USA (1988) 85, 5879-83). The H-chain V-region and the L-chain V-region in the scFv may be derived from any one of the antibodies described herein. The peptide linker which binds the V-regions may be any single chain peptide, for example, of 12-19 amino acid residues.

As a modified antibody, for example, anti-FZD10 antibody or fragment thereof conjugated to any molecule (e.g., polyethylene glycol) may also be used. Such modified antibodies are also encompassed in the "antibody" of the present invention. The modified antibodies can be prepared by chemical modifications of the antibodies. The chemical modification techniques suitable for this purpose have already been established in the art.

2. Therapeutic Uses

Described below are methods and pharmaceutical compositions for treating and/or preventing FZD10-associated disease using the antibody of the present invention. The outcome of a treatment is to at least produce in a treated subject a healthful benefit, which in the case of tumors, includes but is not limited to remission of the tumors, palliation of the symptoms of the tumors, and control of metastatic spread of the tumors.

Specifically, the method for treating and/or preventing FZD10-associated disease in a subject according to the present invention comprises administering to a subject in need thereof the antibody or the fragment described above.

The term "subject" herein refers to a subject who has suffered from FZD10-associated disease and also a subject suspected to have FZD10-associated disease. The subject in the present invention may be animals including mammals and avian animals. For example, mammals may include humans, mice, rats, monkeys, rabbits, and dogs.

The term "FZD10-associated disease" herein refers to a disease associated with the over-expression of FZD10 protein. Specifically, FZD10-associated diseases include, but are not limited to, synovial sarcoma (SS), colorectal cancer, gastric cancer, chronic myeloid leukemia (CML), and acute myeloid leukemia (AML).

The antibody or fragment thereof described herein can specifically bind to FZD10 protein, so when the antibody or fragment thereof is administered to a subject, it binds to FZD10 protein in the subject and the activity of FZD10 protein may be inhibited. Alternatively, when the antibody or fragment thereof may be conjugated with a therapeutic moiety and administered to a subject, it is derivered to a region that expresses FZD10 protein (i.e. suffered region) in a subject and the therapeutic moiety can be selectively delivered to the suffered region and acted thereon. Such therapeutic moiety may be any therapeutics that are known or will be developed for having a therapeutic efficacy on FZD10-associated disease and includes, but not limited to, a radioisotope label and chemotherapeutic agent. A radioisotope label which can be used as therapeutics can be selected depending on a variety of elements including β-ray energy and its emission efficiency, the presence or absence of γ-ray emitted, its energy and emission efficiency, physical half-life, and labeling procedure. Generally, the radioisotope label based on yttrium (such as $^{90}Y$) and iodine (such as $^{125}I$ and $^{131}I$) may be used. A chemotherapeutic agent may be any agent that is known or will be developed for treating FZD10-associated disease and includes, but not limited to, methotrexate, taxol, mercaptopurine, thioguanine, cisplatin, carboplatin, mitomycin, bleomycin, doxorubicin, idarubicin, daunorubicin, dactinomycin, vinblastine, vincristine, vinorelbine, paclitaxel, and docetaxel. The antibody or fragment thereof described herein can selectively bind to FZD10 protein and not bind to a normal cell, so side effect which is caused by the antibody or fragment thereof, or radioisotope or chemotherapeutic agent can be effectively avoided and therefore the therapeutic potency may be high.

The antibody or fragment thereof described herein can be administered to a subject at effective doses to treat or prevent the FZD10-associated disease. An effective dose refers to that amount of an antibody or a fragment thereof sufficient to result in a healthful benefit in the treated subject. Formulations and methods of administration that can be employed when the pharmaceutical composition contains an antibody of the present invention are described below.

Pharmaceutical compositions for use in accordance with the present invention can be formulated in conventional manner using one or more pharmaceutically acceptable carriers or excipients.

The antibodies or fragments thereof can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing and/or dispersing agents. Alternatively, the antibody can be in lyophilized powder form for constitution with a suitable vehicle, e.g., sterile pyrogen-free water, before use.

Toxicity and therapeutic efficacy of the antibody or fragment, or the therapeutic moiety conjugated thereto can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD/ED.

Antibodies or therapeutic moieties that exhibit large therapeutic indices are preferred. While antibodies or moieties that exhibit toxic side effects can be used, care should be taken to design a delivery system that targets such antibodies or moieties to the site of affected tissue in order to minimize potential damage to uninfected cells and, thereby, reduce side effects.

The data obtained from the cell culture assays and animal studies can be used in formulating a range of dosages for use in humans. The dosage of such antibodies lies preferably within a range of circulating plasma concentrations that include the ED50 with little or no toxicity. The dosage can vary within this range depending upon the dosage form employed, the route of administration utilized and types and amounts of the therapeutic moiety conjugated. For any antibody used in the method of the invention, the effective dose can be estimated initially from cell culture assays. A dose can be formulated in animal models to achieve a circulating plasma concentration range that includes the 1050 (i.e., the concentration of the test antibody that achieves a half-maximal inhibition of symptoms) as determined in cell culture. Such information can be used to more accurately determine useful doses in humans. Levels in plasma can be measured, for example, by high performance liquid chromatography.

While depending on the conditions and age of the subject and/or administration route, one skilled in the art can select an appropriate dose of the pharmaceutical composition of the present invention. For example, the pharmaceutical composition of the present invention is administered in an amount such that the antibody according to the present invention is administered to the subject in a day in an amount of about 3 to about 15 µg per kg body weight of subject, and preferably of about 10 to about 15 µg per kg body weight of subject. The administration interval and times can be selected in consideration of the condition and age of the subject, administration route, and response to the pharmaceutical composition. For example, the pharmaceutical composition can be administered to the subject one to 5 times, preferably 1 times a day for 5 to 10 days.

The pharmaceutical composition can be administered systemically or locally. It is preferably administered in a targeting delivery manner so as to deliver the active component to an affected site.

In particular embodiments, the methods and compositions of the present invention are used for the treatment or prevention of FZD10-associated disease together with one or a combination of chemotherapeutic agents including, but not limited to, methotrexate, taxol, mercaptopurine, thioguanine, cisplatin, carboplatin, mitomycin, bleomycin, doxorubicin, idarubicin, daunorubicin, dactinomycin, vinblastine, vincristine, vinorelbine, paclitaxel, and docetaxel.

With respect to radiation therapy, any radiation therapy protocol can be used depending upon the type of FZD10-associated disease to be treated. For example, but not by way of limitation, X-ray radiation can be administered. Gamma ray emitting radioisotopes, such as radioactive isotopes of radium, cobalt, and other elements may also be administered to expose tissues.

In another embodiment, chemotherapy or radiation therapy is administered, preferably at least an hour, five hours, 12 hours, a day, a week, a month, and more preferably several months (e.g., up to three months) subsequent to using the methods and compositions containing the antibody of the present invention. The chemotherapy or radiation therapy administered prior to, concurrently with, or subsequent to the treatment using the methods and compositions according to the present invention can be administered by any method known in the art.

3. Diagnostic and Prognostic Uses

Antibodies directed against FZD10 protein or fragments thereof may also be used as diagnostics and prognostics, as described herein. Such diagnostics methods may used to detect the presence or absence of FZD10-associated disease and the risk of having the disease. The method for diagnosis and/or prognosis of an FZD10-associated disease of the present invention comprises immunologically detecting or determining the FZD10 protein derived from the disease in a sample using an antibody or a fragment thereof according to the present invention. Specifically, a method for diagnosis or prognosis of FZD10-associated disease or of a predisposition to develop the disease in a subject according to the present invention comprises:
 (a) contacting a sample from the subject with an antibody against FZD10 protein or a fragment thereof;
 (b) detecting the FZD10 protein in the sample; and
 (c) judging whether or not the subject suffers from or is at risk of developing the disease based on the relative abundance of the FZD10 protein compared to a control.

The method for diagnosis and/or prognosis of the present invention can be performed based on any procedures, as long as it is an assay using an antibody, i.e., an immunological assay. Thereby one can detect the FZD10 protein using the antibody or a fragment thereof of the present invention as the antibody used in the assay. For example, the FZD10 protein can be detected by using an immunohistochemical staining, immunoassay such as enzyme immunoassays (ELISA and EIA), immunofluorescent assay, radioimmunoassay (RIA), or Western blotting.

A sample to be tested in the method for diagnosis and/or prognosis of FZD10-associated disease of the present invention is not specifically limited, as long as it is a biological sample that may contain the FZD10 protein derived from the FZD10-associated disease. Examples of the sample include extract of a cell or organ, and tissue sections, as well as blood, sera, plasma, lymphocyte cultivated supernatant, urine, spinal fluid, saliva, sweat, and ascites. The abundance of the FZD10 protein as determined in samples such as tumor tissue, tumor biopsy, and metastasis tissue by using the antibody or a fragment thereof of the present invention is specifically useful as an index of an FZD10-associated disease.

For example, antibodies and fragments thereof described herein may be used to quantitatively or qualitatively detect the FZD10 protein. The antibodies (or fragment thereof) of the present invention may, additionally, be employed histologically, as in immunofluorescence or immunoelectron microscopy, for in situ detection of FZD10 protein. In situ detection may be accomplished by removing a histological sample from a subject, such as paraffin-embedded sections of tissues (such as surgical specimens) and applying thereto a labeled antibody of the present invention. The antibody (or fragment thereof) is preferably applied by overlaying a sample with the labeled antibody (or fragment thereof). Using the present invention, those skilled in the art will readily perceive that any of a wide variety of histological methods (such as staining procedures) can be modified in order to achieve such in situ detection.

Immunoassays for FZD10 protein will typically comprise incubating a sample from a subject to be examined, such as a biological fluid, a tissue extract, freshly harvested cells, or lysates of cells that have been incubated in cell culture, in the presence of a detectably labeled antibody of the present invention, and detecting the bound antibody by any of a number of techniques well-known in the art.

The sample may be brought into contact with and immobilized onto a solid phase support or carrier such as nitrocellulose, or another solid support which is capable of immobilizing cells, cell particles, or soluble proteins. The support may then be washed with suitable buffers followed by treatment with the detectably labeled antibody against FZD10. The solid phase support may then be washed with the buffer a second time to remove unbound antibody. The amount of bound label on the solid support may then be detected by conventional means.

The term "solid phase support or carrier" means any support capable of binding an antigen or an antibody. Those skilled in the art will know many suitable carriers for binding antibodies or antigens, or will be able to ascertain the same by use of routine experimentation.

The binding activity of a given lot of anti-FZD10 antibody may be determined according to well-known methods. Those skilled in the art will be able to determine operative and optimal assay conditions for each determination by employing routine experimentation.

To detect a reaction between the antibody (or its fragment) of the present invention and the FZD10 protein derived from an FZD10-associated disease affected site in a sample easily, the reaction can be directly detected by labeling the antibody of the present invention or indirectly detected by using a labeled secondary antibody. The latter indirect detection procedure, such as a sandwich assay or competitive assay of ELISA, is preferably used in the method of the present invention for better sensitivity.

Examples of labels for use herein are as follows. Peroxidases (PODs), alkaline phosphatases, β-galactosidase, urease, catalase, glucose oxidase, lactate dehydrogenase, amylases, and biotin-avidin complexes can be used in an enzyme immunoassay.

Fluorescein isothiocyanate (FITC), tetramethylrhodamine isothiocyanate (TRITC), substituted rhodamine isothiocyanate, dichlorotriazine isothiocyanate and Alexa488 can be used in an immunofluorescent assay. Tritium, iodine (such as $^{125}$I, and $^{131}$I), and indium (such as $^{111}$In) can be used in a radioimmunoassay. NADH-FMNH$_2$-luciferase assay, luminol-hydrogen peroxide-POD system, acridinium esters, and dioxetane compounds can be used in an immunoluminescent assay.

The label can be attached to the antibody according to a conventional procedure. For example, the label can be attached to the antibody by a glutaraldehyde method, maleimide method, pyridyl disulfide method, or periodate method in the enzyme immunoassay, and by a chloramine T method or Bolton-Hunter method in the radioimmunoassay.

The assay can be performed according to a known procedure (Ausubel, F. M. et al. Eds., Short Protocols in Molecular Biology, Chapter 11 "Immunology" John Wiley & Sons, Inc. 1995).

For example, when the antibody of the present invention is directly labeled with the label described above, the sample is brought into contact with the labeled antibody to thereby form a complex between the FZD10 protein and the antibody. Then, unbound labeled antibody is separated, and the level of the FZD10 protein in the sample can be determined based on the amount of the bound labeled antibody or that of the unbound labeled antibody.

When a labeled secondary antibody is used, the antibody of the present invention is allowed to react with the sample in a primary reaction, and the resulting complex is allowed to react with the labeled secondary antibody in a secondary reaction. The primary reaction and the secondary reaction can be performed in reverse order, concurrently with some interval of time therebetween. The primary and secondary reactions yield a complex of [FZD10 protein]-[the antibody of the invention]-[the labeled secondary antibody] or a complex of [the antibody of the invention]-[FZD10 protein]-[the labeled secondary antibody]. Unbound labeled secondary antibody is then separated, and the level of the FZD10 protein in the sample can be determined based on the abundance of the bound labeled secondary antibody or that of the unbound labeled secondary antibody.

According to another embodiment, the antibody of the present invention is labeled with a radioisotope or a fluorescent label, and the labeled antibody is parenterally administered to a subject. Thus, the localization of a primary tumor and the related metastasized tumor of FZD10-associated disease can be rapidly found in a non-invasive manner. Such a diagnosis method is known as tumor in vivo imaging, and one skilled in the art can easily understand the procedures thereof. The labeled antibody can be administered to the subject systemically or locally, preferably through a parenteral route such as intravenous injection, intramuscular injection, intraperitoneal injection, or subcutaneous injection.

The antibodies according to the present invention specifically react with a FZD10 protein as mentioned above and can thereby be used in kits for diagnosis and/or prognosis of an FZD10-associated disease.

The kit for diagnosis and/or prognosis of the present invention comprises an antibody or a fragment thereof described herein. By detecting the FZD10 protein in a sample from a subject who is suspected to suffer from an FZD10-associated disease with the use of the kit for diagnosis and/or prognosis of the present invention, whether or not the subject suffers from the FZD10-associated disease can be rapidly and easily ascertained. Kits for diagnosis and/or prognosis of diseases using such immunological reactions have been widely known, and one skilled in the art can easily select appropriate components other than the antibody. The kits for diagnosis and/or prognosis of the present invention can be used in any means, as long as it is a means for immunoassay.

EXAMPLES

The present invention will be further illustrated by the following non-limiting examples.

Cell lines and tissue specimens used in the following examples were prepared as described below. Specifically, cell lines derived from synovial sarcomas (HS-SY-2, YaFuSS, 1973/99, Fuji and SYO-1), colon cancers (LoVo, SNU-C4 and SNU-05), HEK293 and COST cells were grown in monolayers in appropriate media supplemented with 10% fetal bovine serum and 1% antibiotic/antimycotic solution, and maintained at 37° C. in air containing 5% CO$_2$. Primary synovial sarcoma (SS) samples were obtained after informed consent, and snap-frozen in liquid nitrogen immediately after resection and stored at −80° C.

Example 1

Generation of Anti-FZD10 Monoclonal Antibodies (1) Generating Monoclonal Antibodies with Cell Immunization Mouse anti-FZD10 monoclonal antibodies (Mabs) were generated by immunizing four weeks old female Balb/c mice in their foot pads with 2×10$^7$ COS-7 cells transfected with 2×10$^7$ of pCAGGS/neo-FZD10-myc/His (Medical and Biological Laboratories, Nagoya, Japan). Construction of pCAGGS/neo-FZD10-myc/His was reported previously (Nagayama, S., et al. (2005). Oncogene, 24, 6201-12) and this expresses the entire coding sequence of FZD10 cDNA and Myc and His epitope tags at its C terminus. The mice had been immunized with Freund complete adjuvant (Mitsubishi Kagaku Iatron, Inc., Tokyo, Japan) in one day prior to the cell immunization. Spleen cells from the immunized mice were harvested and fused with the myeloma cell line. The hybridomas were subcloned and assayed by Cell ELISA for the ability to secrete immunoglobulin that binds to the extracellular domain of FZD10 (amino acid residues 1-225 of FZD10). For cell ELISA, COS-7 cells expressing FZD10-myc/His (the entire coding sequence of FZD10 cDNA and Myc and His epitope tags at its C terminus) were seeded into 96-well plates. Subsequently, 50 μl of the culture supernatants obtained from hybridomas were added to the plate and incubated for 30 minutes at room temperature. After washing the cells, goat anti-mouse IgG-POD (Medical and Biological Laboratories, Nagoya, Japan) was added at 1:10000 dilution, incubated for 30 minutes at room temperature. Bound antibodies were detected at OD$_{450-620}$ nm. Positive clones were further analyzed for specific binding activity. These clones includes: clones 39-2 and 39-10 (disclosed in WO2005/004912, referred to as 5F2) as well as 92-13 and 93-22. All Mabs were of the IgG2a isotype as determined by means of the IsoStrip Mouse Monoclonal antibody isotyping kit (Roche). The Mabs were affinity purified on protein G-sepharose for further characterization.

The hybridoma clone 93-22 producing mouse monoclonal antibody 93-22 was deposited by Shuichi Nakatsuru internationally at the IPOD International Patent Organism Depositary of the National Institute of Advanced Industrial Science and Technology (AIST Tsukuba Central 6, 1-1, Higashi 1-chome, Tsukuba-shi, Ibaraki-Ken, 305-8566 Japan) as of Jun. 14, 2006 under the deposit number of FERM BP-10620. Also, hybridoma clone 92-13 producing mouse monoclonal antibody 92-13 was deposited by Shuichi Nakatsuru internationally at the IPOD International Patent Organism Depositary of the National Institute of AIST as of Jun. 28, 2006 under the deposit number of FERM BP-10628.

(2) Labeling Antibodies with Radionuclides $^{125}$I-labeled Mabs were prepared by chloramine T method (Arano, Y., et al. (1999). Cancer Res, 59, 128-34). 740 kBq/2 µl of Na$^{125}$I was added to 10 µg of Mab in 100 µl of 0.3M sodium phosphate buffer. One µg of chloramine-T in 3 µl of 0.3M sodium phosphate buffer was further added, incubated for 5 min at room temperature. Labeled antibody was purified using Biospin column 6 (Bio-Rad).

For labeling Mabs with $^{111}$In, 1 mg of Mab in 100 µl of 50 mM borate buffer (pH8.5) was conjugated to isothiocyanato benzyl diethylenetriaminepentaacetic acid (SCN-BZ-DTPA; Macrocyclics) in dimethylformamide at molar ratio 1:3. After incubation at 37° C. for 20 hours, Mab conjugates were purified using Biospin column 6. 40 µl of $^{111}$In was incubated in 60 µl of 0.25M acetic acid buffer (pH5.5) and incorporated into 10 µg/µl of Mab-DTPA conjugates for one hour at room temperature. Labeled antibody was purified using Biospin column 6.

For generating $^{90}$Y-conjugated 92-13, 92-13 was conjugated with DTPA to lysine residues. DTPA-92-13 was labeled with yttrium to a specific activity 100 µCi/mg, and the immunoreactivity of the $^{90}$Y-DTPA-92-13 was approximately 70%.

(3) Synthesis of Alexa647-Labeled Mabs.

Labeling Mabs with Alexa-Fluoro647 was carried out according to manufacturer's instruction using Alexa647 Monoclonal Antibody Labeling Kit (Molecular Probes, Eugene, Oreg.). The Alexa647 reactive dye has a succinimidyl ester moiety that reacts with primary amines of proteins, and resulting Mabs-dye conjugates were purified by size exclusion column.

Example 2

Binding Activities of Anti-FZD10 Monoclonal Antibodies

The present inventors applied two methods for evaluation of the binding affinity of mouse-monoclonal antibodies; flow cytometrical analysis with fluorescent dyes and radioactive measurement using $^{125}$I.

(1) Flow Cytometry (FACS) Analysis

To investigate the cell-binding affinities of the four antibodies, 39-2 and 39-10 (disclosed in WO2005/004912), 92-13 and 93-22, we performed flow cytometry (FACS) experiments. For flow cytometrical analysis with indirect fluorescence, suspensions of 5×10$^6$ cells were incubated with 10 µg/ml of Mabs or non-immunized mouse IgG (Beckman Coulter) for 30 min at 4° C. After washing with PBS, 2 µg of fluorescent goat anti-mouse IgG (Alexa Fluor 488, Molecular Probes, Eugene, Oreg.) was added, and the cell suspension was incubated for 30 min at 4° C. for analysis by FACScan (Becton Dickinson, Franklin Lakes, N.J.). For direct immunofluorescence assays, cells were incubated with 2 µg of Alexa488-Mabs in the presence or absence of excess amount (100 µg) of non-labeled Mabs for 30 min at 4° C. and subjected to analysis by FACScan.

In order to confirm the expression of FZD10 in cell lines, we performed RT-PCR. For RT-PCR experiments, total RNAs were extracted from cell lines using TRIzol reagent (Invitrogen, Carlsbad, Calif., USA), and 3 µg aliquot of each total RNA was reversely transcribed. PCR amplification was performed using the cDNAs as templates with the following primers: 5'-TATCGGGCTCTTCTCTGTGC-3' (SEQ ID NO: 9) and 5'-GACTGGGCAGGGATCTCATA-3' (SEQ ID NO: 10) for FZD10 and 5'-TTAGCTGTGCTCGCGCTACT-3' (SEQ ID NO: 11) and 5'-TCACATGGTTCACACGGCAG-3' (SEQ ID NO: 12) for β2-microglobulin (β2MG), the internal control.

Figure 1A:
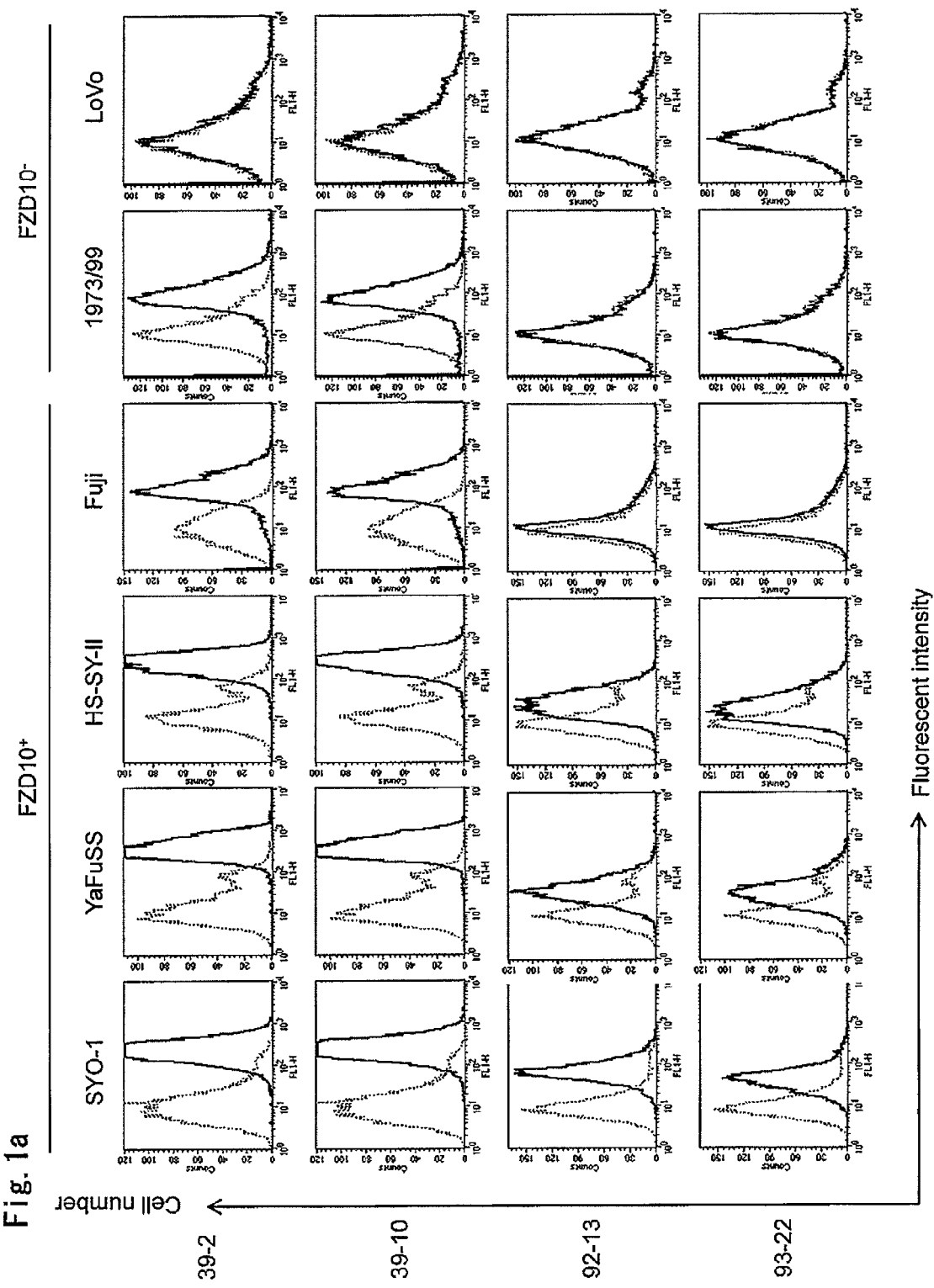
FIGS. 1a to 1f show characterization of binding specificity for two anti-FZD10 monoclonal antibodies.
Figure 1B:
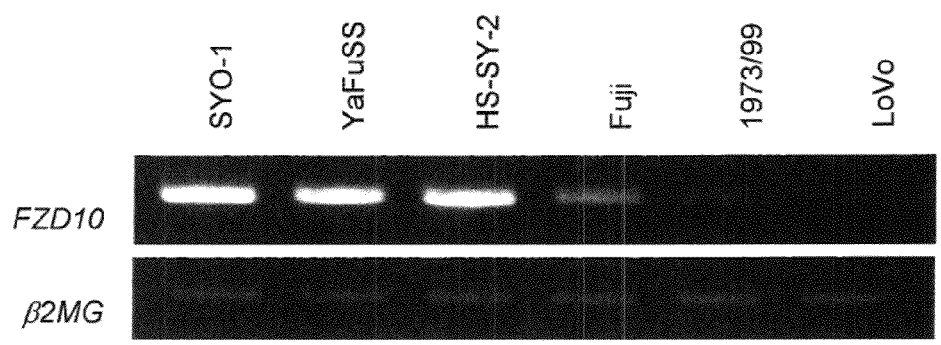
Figure 1C:
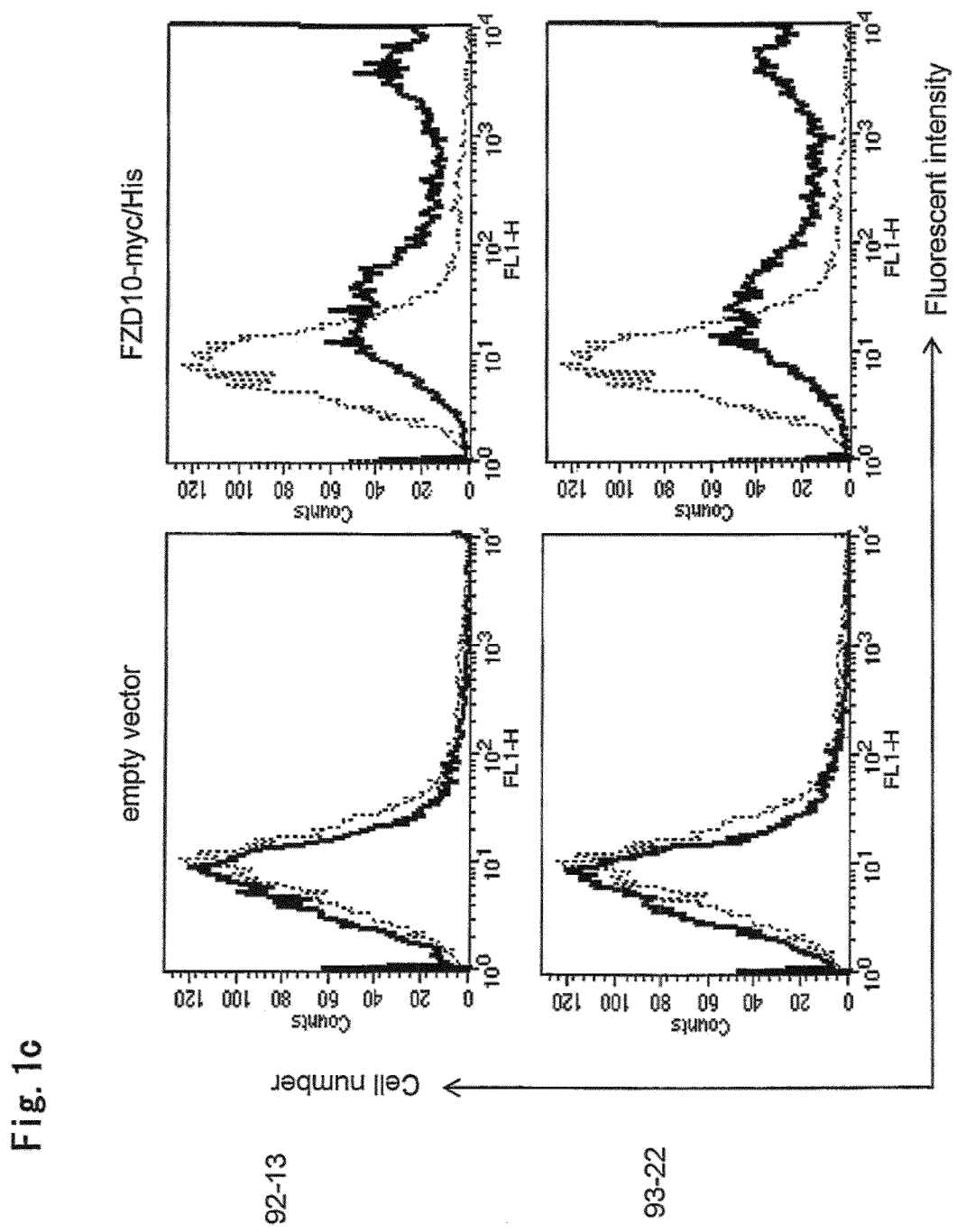

As shown in FIG. 1a, all of four Mabs, 39-2, 39-10, 92-13 and 93-22 bound to four FZD10-expressing SS cell lines, SYO-1, YafuSS, HS-SY-2, and Fuji in FZD10-dose dependent manner, but not bound to two cell lines, 1973/99 and LoVo, in which no transcript of FZD10 was detected. Table 1 below indicates correlation between relative Mean fluorescent Intensities (MFI) of these Mabs and the expression levels of FZD10 shown in FIG. 1b. In addition, particularly, we demonstrated that 92-13 and 93-22 Mabs also bound to the SNU-05 transfected with FZD10-myc/His construct, while no binding was detected with SNU-05 cells transfected with empty vector (FIG. 1c), suggesting specific binding of those 92-13 and 93-22 Mabs against FZD10 protein.

TABLE 1

Binding of anti-FZD10 mAbs to human SS cell lines SYO-1, YaFuSS, HS-SY-II, Fuji, 1973/99 and human colon cancer cell line, LoVo.

|  | SYO-1 | YaFuss | HS-SY-II | Fuji | 1973/99 | LoVo |
| --- | --- | --- | --- | --- | --- | --- |
| 39-2 | 17.6 | 11.6 | 9.4 | 7.1 | 5.5 | 1.1 |
| 39-10 | 18.4 | 11.8 | 9.9 | 6.9 | 4.9 | 1.0 |
| 92-13 | 4.7 | 3.0 | 3.0 | 1.3 | 0.9 | 1.0 |
| 93-22 | 3.3 | 2.7 | 2.4 | 1.1 | 1.0 | 1.1 |

The MFI of FZD10 is measured by flow cytometry as described above.

(2) Binding Activity Against Normal Blood Cells

To confirm whether those antibodies can be applied for clinical use, the present inventors further examined the binding activity of antibodies against normal blood cells. To evaluate the non-specific binding activity of Mabs against normal blood cell, $^{125}$I-labeled Mabs were incubated with 100 µl of healthy fresh blood. After incubation for one hour at room temperature, the radioactivities of cell pellet were measured as described above.

Figure 1D:
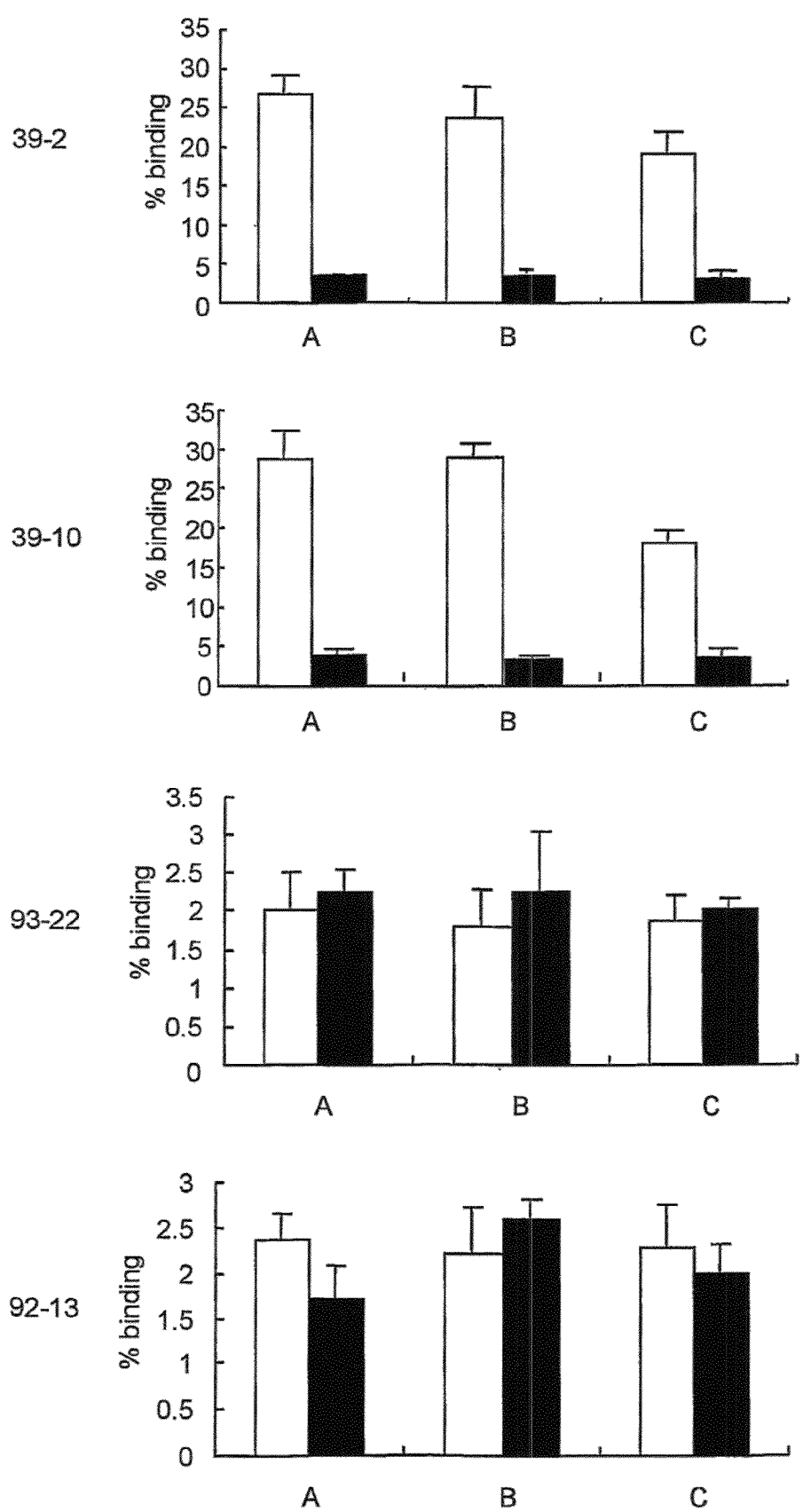

The binding activity of $^{125}$I-labeled 92-13 and 93-22 Mabs against normal human blood cells were undetectable in all of three individual donors, whereas those of 39-2 and 39-10 Mabs were detected in all of three individual donors (FIG. 1d). These results were consistent with those of FACS analysis using human peripheral blood mononuclear cell (data not shown), suggesting clinical applicability of only 92-13 and 93-22 antibodies with little possibility of adverse effect to SS patients because of very specific binding affinity to the FZD10 molecule. Therefore, we focused on only 92-13 and 93-22 antibodies for further analysis.

(3) Additional Analyses

Furthermore, binding assay was performed using $^{125}$I-labeled Mabs (see Example 1 (2)) to evaluate the binding affinity against FZD10 molecules on cell surface. For radioactive analysis, 0.5 kBq (0.001 μg antibody) $^{125}$I-labeled Mabs prepared in Example 1 (2) were added to 100 μl of cell suspension with various amounts of non-labeled identical Mabs. After incubation for one hour at room temperature, the cell suspension was centrifuged at 800×g. Supernatant was removed and the radioactivity of cell pellet was measured.

Figure 1E:
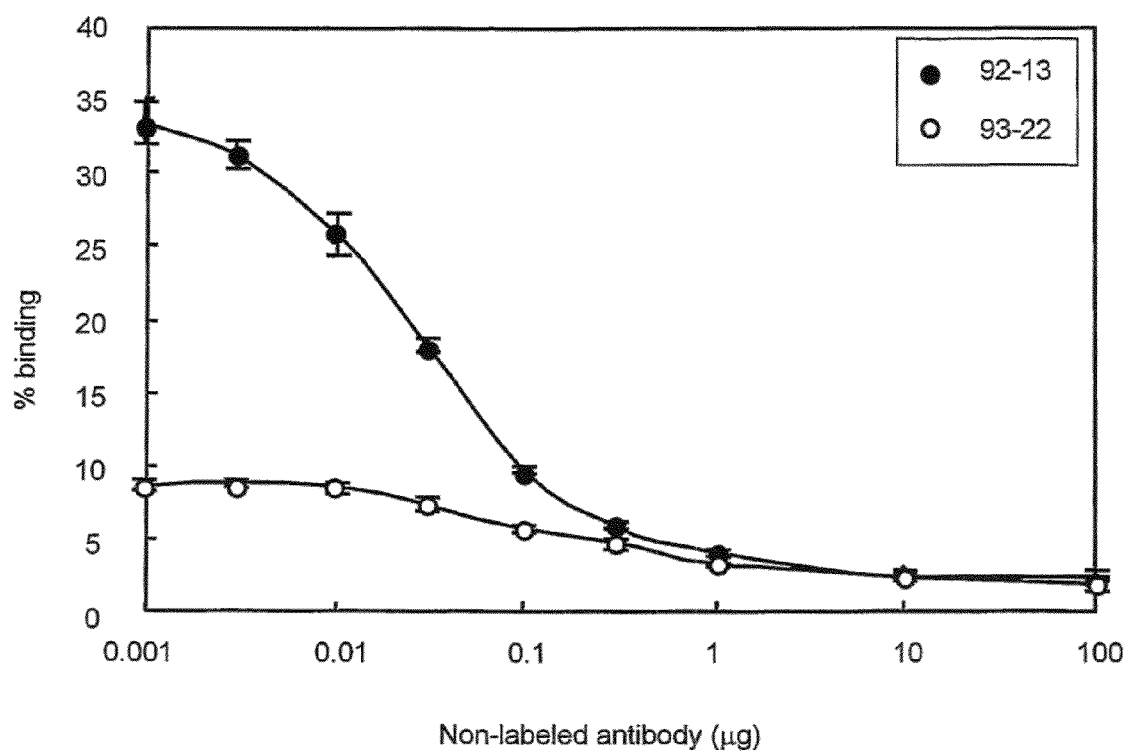
Figure 1F:
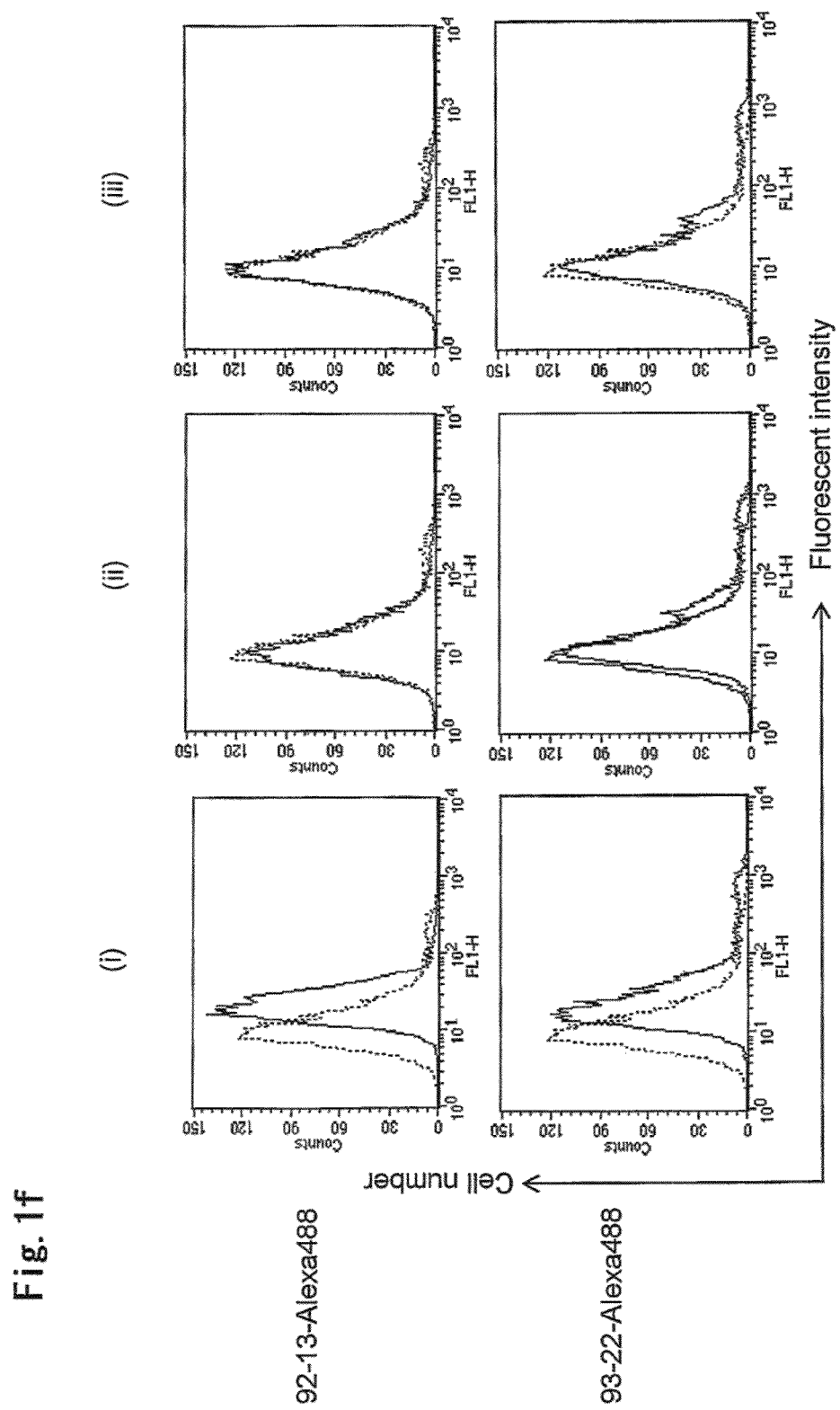

The results showed higher binding affinity of 92-13 antibody than 93-22 antibody; approximately 33% of 92-13 bound to the cells and approximately 9% of 93-22 antibody bound to the cells under the same condition (FIG. 1e). The amount of the bound antibody decreased as non-labeled antibodies were added in a dose-dependent manner.

We subsequently performed binding competition analysis of 92-13 with 93-22 Mabs using flow cytometry. Cell binding of the both of Alexa488-labeled antibodies were completely blocked by high amount of non-labeled antibodies (FIG. 1f, ii and iii) to each other, suggesting that 92-13 and 93-22 Mabs are likely to recognize very similar or same epitope of FZD10. These findings suggest that these Mabs is able to specifically recognize FZD10 expressed on cell surface of SS cells.

Example 3

Immunohistochemistry

To evaluate the binding specificity of 92-13 and 93-22 to human tissues, we performed immunohistochemical analysis using frozen tissue sections. Tissue sections of frozen normal adult human organs (BioChain, Hayward, Calif.) were fixed with 4% paraformaldehyde at 4° C. for 15 min, and incubated with 5 μg/ml Mabs for one hour at room temperature. Subsequently, mouse ENVISION Polymer Reagent (DAKO) was added and visualized with peroxidase substrate (3,3'-Diaminobenzidine Tetrahydrochloride).

Figure 2:
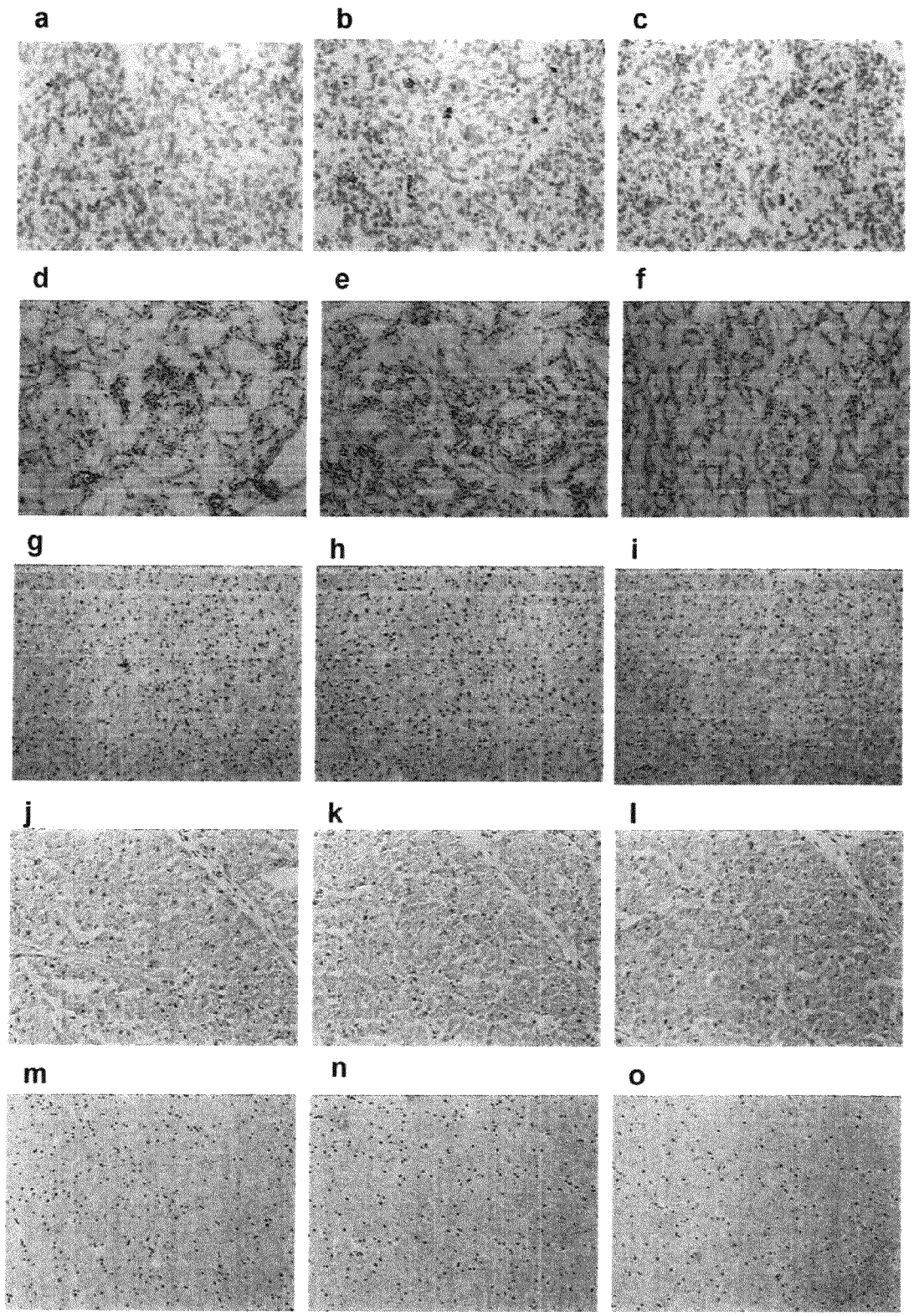
FIG. 2 shows immunohistochemical analyses in SS and normal human frozen tissue sections with no antibody (a, d, g, j, and m), 92-13 (b, e, h, k, and n) and 93-22 (c, f, i, l, and o). (a-c), synovial sarcoma; (d-f), kidney; (g-i), liver; (j-l), heart; (m-o), brain. Original magnification: ×100.

The results are shown in FIG. 2. FIG. 2 shows immunohistochemical analyses in SS and normal human frozen tissue sections with no antibody (a, d, g, j, and m), 92-13 (b, e, h, k, and n) and 93-22 (c, f, i, l, and o). (a-c), synovial sarcoma; (d-f), kidney; (g-i), liver, (j-l), heart; (m-o), brain. Expectedly, we observed strong immunoreactivity to FZD10 in SS specimen (FIG. 2, a, b, and c) and placenta (data not shown), but did not detect in normal kidney, heart, brain and liver (FIG. 2, d-o), as concordant with the results of northern-blot and RT-PCR experiments (Nagayama, S., et al. (2005). Oncogene, 24, 6201-6212).

Example 4

Biodistribution of Anti-FZD10 Mabs in Balb/c Mice Xenograft Model

Distribution of 92-13 and 93-22 in in vivo model was examined in BALB/c mice by means of two independent methods, radionuclide imaging and fluorescent imaging.

(1) In Vivo Radionuclide Imaging

In vivo experiments were performed in the animal facility in accordance with institutional guidelines. BALB/cA Jcl-nu mice (female, 7 weeks old) were injected subcutaneously (s.c.) with SYO-1 tumor cells (5×10$^6$ cells), in 0.1 ml PBS, in the flanks. For biodistribution studies, mice with fully established tumors were given 10 kBq (0.5-1 μg) of $^{125}$I-labeled Mabs and 10 kBq (0.5-1 μg) of $^{111}$In-labeled Mabs via tail vain. At 1, 24, 48 hours, animals were euthanized and the weight and radioactivity of tissues were measured. The distribution was expressed as % of injected dose/g of tissue for all samples. For optical imaging of biodistribution, LoVo-tumor bearing mice were used in addition to SYO-1 tumor mice. LoVo tumor cells (1×10$^7$ cells) were injected s.c. into BALB/cA Jcl-nu mice as described above. When tumors were fully established, the mice were subjected to the imaging study.

The results in FIG. 3a demonstrates that the radioactivity of $^{111}$In-92-13 associated with the blood decreased from 35% injected dose per gram (% ID/g) at one hour postinjection to 12% after 48 hours. Radioactivities of $^{111}$In-92-13 associated liver, kidney, intestine, spleen, pancreas, lung, heart, stomach and muscle remained fairly constant or decreasing throughout the observation (FIG. 3a). Radioactivity of $^{111}$In-92-13 associated with tumor accumulated throughout the experiment, from 2% ID/g at one hour postinjection to 11% ID/g after 48 hours. On the other hand, FIG. 3b demonstrates that radioactivity of $^{125}$I-labeled 92-13 associated with tumor did not increased significantly although blood-associated radioactivity fell from 25% at one hour to 7% after 48 hours and radioactivities associated with other normal organs remained constant. The $^{125}$I-labeled antibodies were possibly degraded inside the cell after internalization. $^{111}$In-labeled 93-22 was also accumulated into SYO-1 tumor at 48 hours postinjection (FIG. 3c) and $^{125}$I-labeled 93-22 showed poor accumulation (FIG. 3d), suggesting its internalization as well as 92-13.

(2) In Vivo Fluorescence Imaging

In vivo fluorescence imaging was performed with IVIS™ Imaging System 100 series (Xenogen, Alameda, Calif.). An optimized Cy$_{5.5}$ filter was used to acquire Alexa647-Mabs fluorescence in vivo. SYO-1 tumor-bearing mice were injected 20 μg of Alexa647-labeled Mabs intraperitoneally and subjected to fluorescent imaging at various time points. The mice were fed with food that is not containing alfalfa for four days in prior to injecting Mabs in order to reduce the background fluorescence. When acquiring images, mice were anesthetized with 2% of isoflurane (Abbott Laboratories) and placed in the IVIS system. The mice were euthanized at four days after the Mab injection, the tumor and major organs were dissected, and fluorescence image was obtained.

Figure 4A:
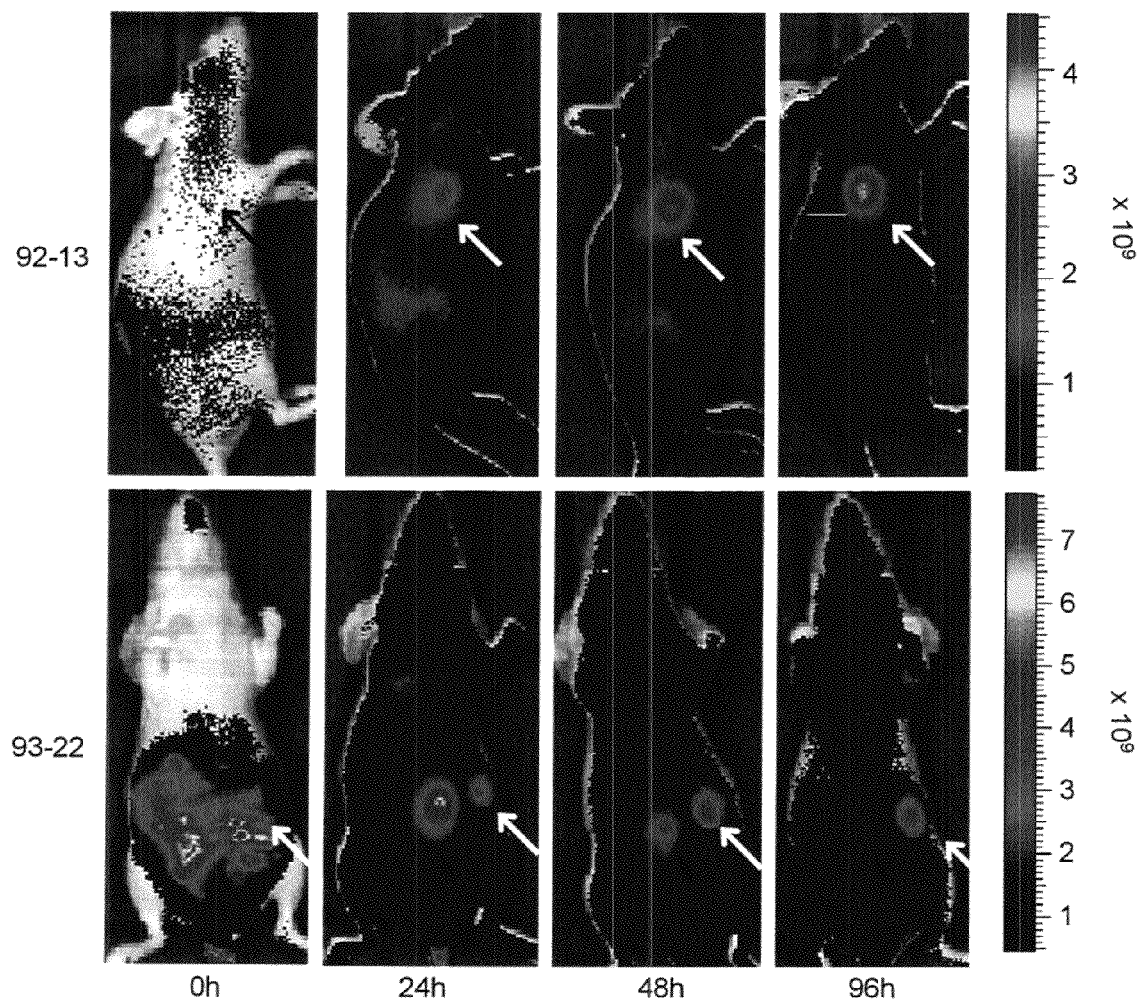
FIG. 4a shows in vivo fluorescence imaging of SYO-1 tumor-bearing mice after injection of Alexa 647-labeled 92-13 or 93-22. Fluorescence-labeled Mabs were administered at a dose of 20 μg per mouse intraperitoneally. All fluorescence images were acquired with a 60-second exposure time (f/stop=2) before injection, immediately after injection (0 hour), 24, 48 and 96 hours. The arrows indicate the position of the tumor. S.C. tumor is located in dorsal for 92-13 (top panels) and in trunk for 93-22 (lower panels). Fluorescence signal from Alexa647 was pseudo-colored according to the color bar indicated on right. In 93-22 (lower panel), the arrowheads indicate the position of injection.
Figure 4B:
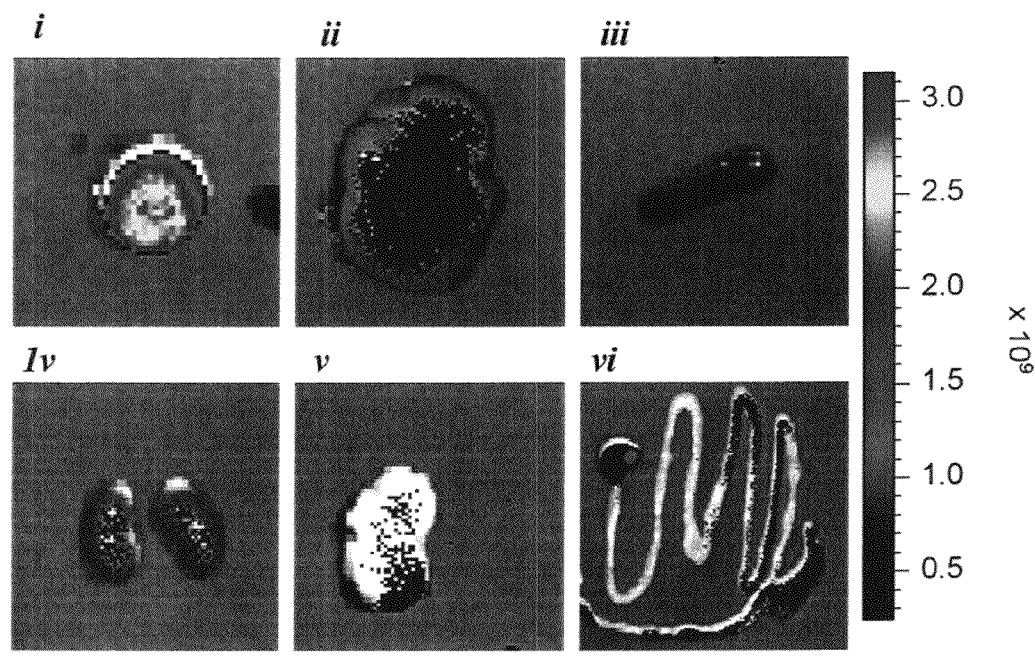
FIGS. 4b and 4c show representative images of dissected organs and tumors from mice shown in FIGS. 4a, 4b; 92-13, and 4c; 93-22. i, SYO-1 tumor; ii, liver; iii, spleen; iv, kidney; v, pancreas; vi, colon.
Figure 4C:
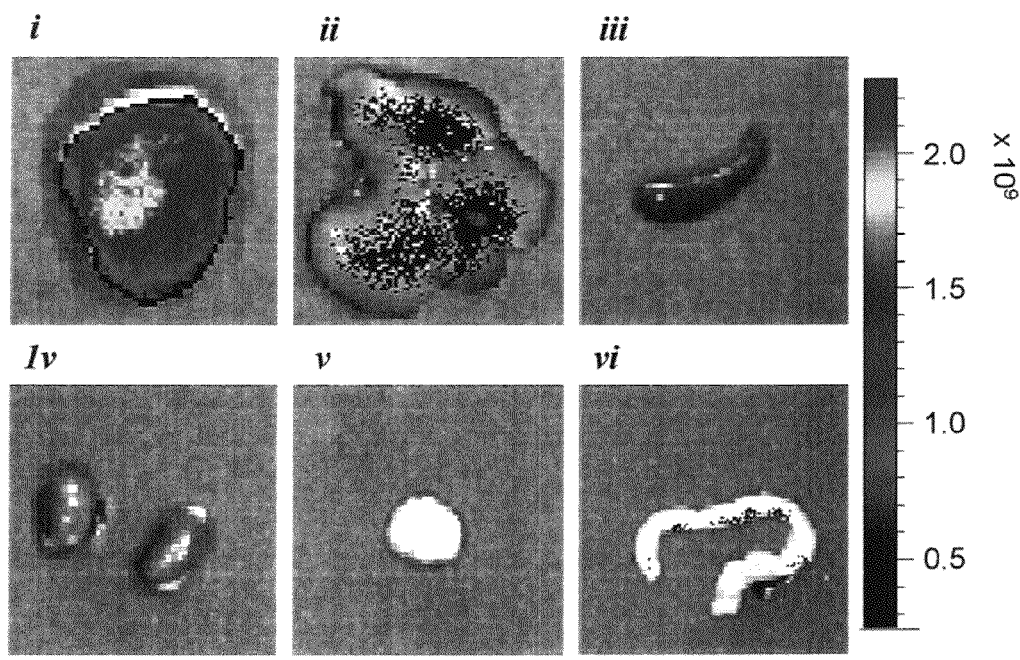
Figure 5A:
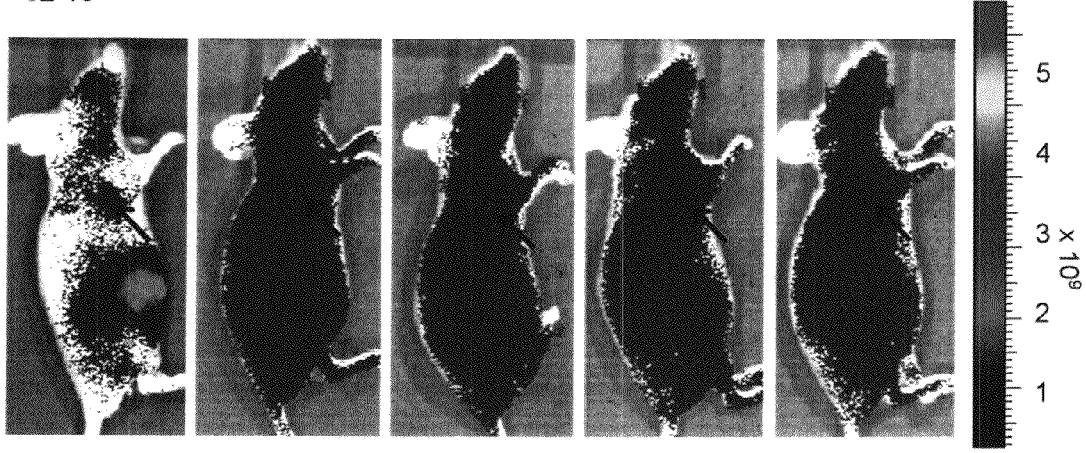
FIG. 5a shows in vivo fluorescence imaging of LoVo tumor-bearing mice after injection of Alexa647-labeled 92-13 or 93-22. Fluorescence-labeled Mabs were administered as FIG. 4. All fluorescence images were acquired with a 60-second exposure time (f/stop=2) immediately after injection (0 hour), 48, 72, 96 and 120 hours (h). Arrow indicates the position of the tumor. S.c. tumor is located in right forearm both for 92-13 (Top panels) and 93-22 (lower panels).
Figure 5A:
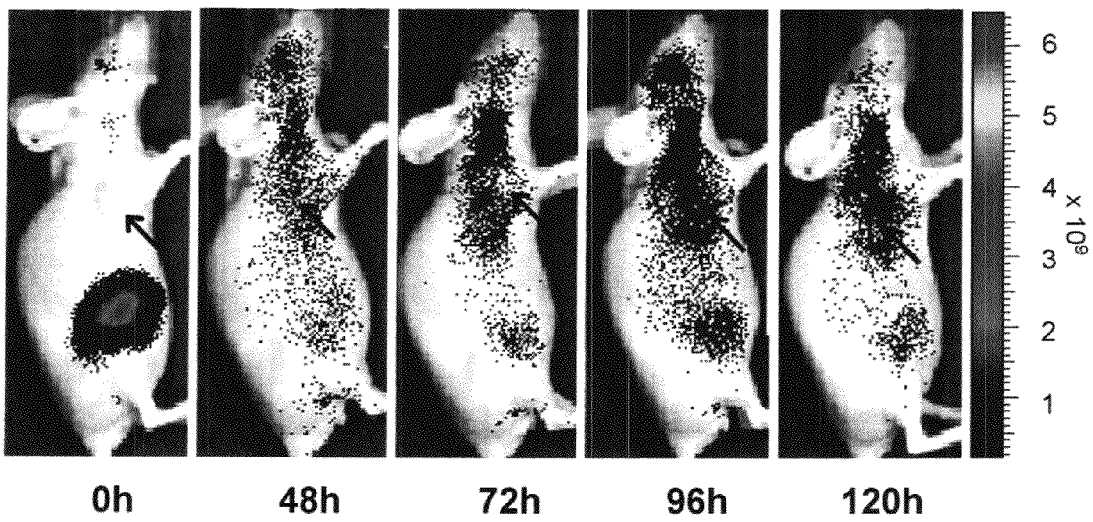
Figure 5B:
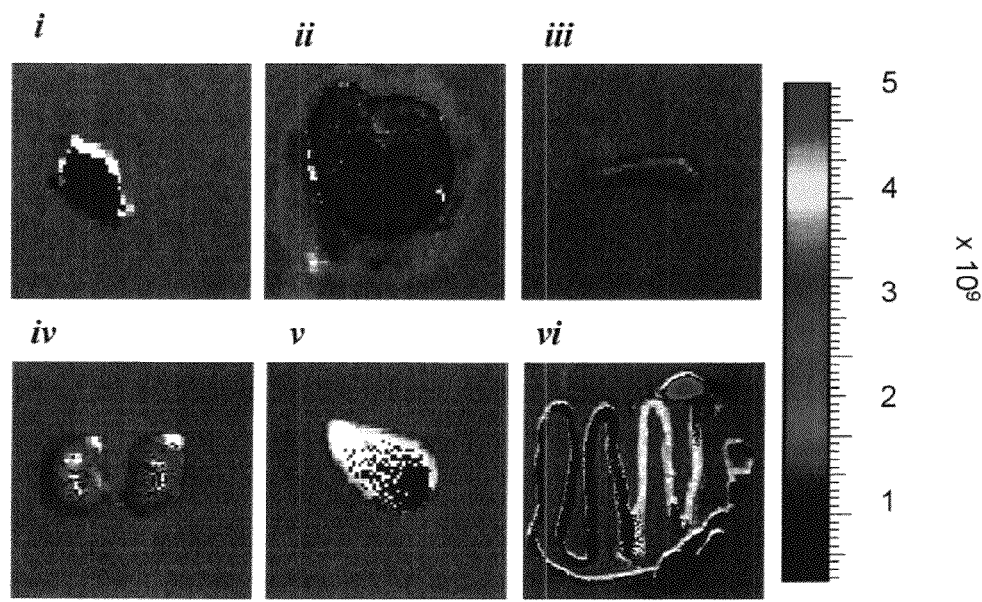
FIGS. 5b and 5c show representative images of dissected organs and tumors of mice shown in FIGS. 5a, 5b; 92-13 and 5c; 93-22. i, LoVo tumor; ii, liver; iii, spleen; iv, kidney; v, pancreas; vi, colon.
Figure 5C:
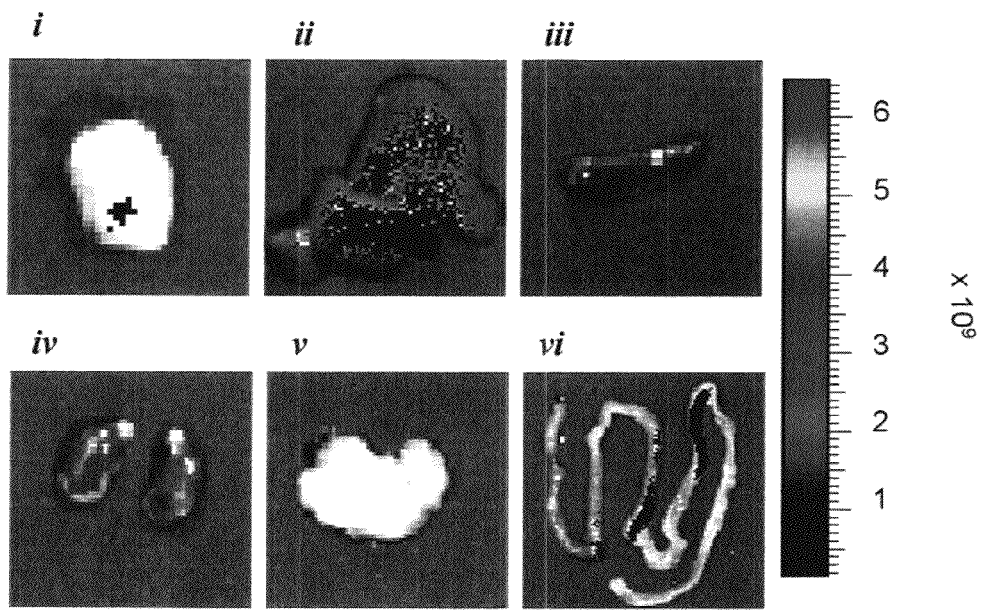

As shown in FIG. 4a, significant amount of fluorescence was detected at the location of tumor at 24 hours after the injection. The tumor-bound fluorescence was observed for both Mabs, 92-13 and 93-22; the signals reached at maximum level at about 48 hours after the injection, and could be detectable at 96 hours after the injection. The present inventors sacrificed these mice at 120 hours postinjection and measured their fluorescence intensity in the tumor and also important normal organs (liver, spleen, kidney, pancreas, colon) (FIGS. 4b and 4c). Very strong fluorescence signal was observed in the dissected tumor, whereas no fluorescence signal was detected in normal organs. To validate the binding specificity, the present inventors generated xenografts using antigen-negative cell line, LoVo, in nude mice and injected Alexa647-labeled Mabs, performed fluorescent imaging analysis. In LoVo-bearing mice, fluorescent was detected neither at the location of the tumor (FIG. 5a), nor in the dissected tumor or other organs (FIGS. 5b and 5c). These results demonstrated that these Mabs are also able to bind specifically to FZD10-expressed tumor cells in vivo.

Example 5

Internalization of Anti-FZD10 Mabs into Antigen-Positive Cells

To investigate molecular behavior of these Mabs after binding to the cell surfaces, their localization was traced using in vitro imaging system.

Cells were plated into 8-well chamber slides (Nalge Nunc International, Naperville, Ill.) at density of $5 \times 10^4$ cells per well. Cells were incubated with Mabs for three hours at 37° C. in air chamber containing 5% $CO_2$. Mabs bound to the cell surface were removed by acid stripping buffer (0.1M Glycine, 500 mM NaCl, pH2.5) at 4° C. for 10 min and neutralized with 500 mM Tris (pH7.5). Cells were then fixed with 3.7% formaldehyde for 15 min at room temperature, and permeabilized by exposure to 0.2% TritonX-100 for 10 min, followed by blocking with 3% bovine serum albumin for one hour at room temperature. To detect the Mabs internalized into the cell, samples were incubated with Alexa488-labeled goat-anti mouse IgG (1:700 dilution) for one hour at room temperature. The slides were mounted with DAPI (Vectashield, Vector Laboratories, Burlingame, Calif.) and analyzed under Leica TCS SP1 confocal optics.

As shown in FIG. 6, both Mabs 92-13 and 93-22 were efficiently incorporated into the cytosol of SYO-1 cells and YaFuSS cells at 3 hours after the incubation of Mab with cells by confocal microscope imaging detected using Alexa488-labeled goat anti-mouse IgG (FIG. 6, a-f). On the other hand, the fluorescence signals of these Mabs were hardly detectable in LoVo cells without FZD10 expression (FIG. 6, g-i), demonstrating that the specific binding of Mabs to cell-surface FZD10 induced the internalization of the antibodies.

Example 6

Specific Cytotoxicity of Mabs 92-13 and 93-22 had no effect on tumor cell growth when added directly into the cultured cell (data not shown). For therapy studies, SYO-1 tumors were grown in BALB/cA Jcl-nu mice in the same manner as in Example 4. The diameters of the tumors were measured by calipers and the tumor volumes were determined using the following formula; $0.5 \times$ (larger diameter)$\times$(smaller diameter)$^2$ as described previously (Nagayama, S., et al. (2005). Oncogene, 24, 6201-12). When the tumor volumes reached more than 0.4-2.8 $cm^3$, Balb/c-nude mice bearing subcutaneous SYO-1 tumor were randomly assigned to treatment groups and received intravenous injections of the 100 µCi of $^{90}$Y-labeled Mabs or control Mabs via tail vain. Mice were weighed and tumor diameters were recorded.

FIG. 7 showed that tumor volumes were markedly reduced immediately after treatment, almost to traces within one week in all mice. When 50 µCi of $^{90}$Y-DTPA-92-13 were given to the mice, tumors >1 $cm^3$ volumes refracted two weeks after treatment although they showed marked reduction of tumor size immediately after treatment. The mice showed temporary decrease of the weight (10~15%), however, they recovered in one week and no visible toxic signs were observed (data not shown).

Example 7

Generation of Chimeric Antibodies

Chimeric antibodies corresponding to mouse 92-13 and 93-22 antibodies, ch92-13 and ch93-22 were generated by replacement of the variable region sequence of each mouse antibody to the human IgG1 constant region under the control of CMV promoter. Total RNAs were extracted from hybridoma clones 92-13 and 93-22. cDNA was synthesized from the total RNA using GeneRacer™ Kit (Invitrogen). The sequences of variable regions of monoclonal antibodies were amplified using forward primer (GeneRacer™ 5'Primer) and reverse primer; CH1 (IgG2a); 5'-AATTTTCTTGTCCACCT-TGGTG-3' (SEQ ID NO: 3) for heavy chain and CL1 (kappa); 5'-CTAACACTCATTCCTGTTGAAGCTCT-3' (SEQ ID NO: 4) for light chain. PCR products were sequenced and the sequences coding the m92-13 and m93-22 variable region were determined.

As a result, the amino acid sequence of mouse Ig H-chain variable regions and L-chain variable regions were determined as follows:

92-13, H-Chain Variable Region:
<u>MKCSWVIFFLMAVVTGVNS</u>EVQLQQSGAELVKPGA-SVKLSCTASGFNINDTYMH WVKQRPEQGLEWI-GRIDPANGNTKYDPKFQGKATI-TADTSSNTAYLQLSSLTSEDT AVYYCARGARGSRFAY-WGQGTLVTVSA (SEQ ID NO: 13) encoded by the nucleotide sequence of SEQ ID NO: 14, and 92-13, L-chain variable region:
<u>MSVPTQVLGLLLLWLTDARCD</u>IQMTQSPASLSVSVG-ETVTITCRASENIYSNLAWY QQKQGKSPQLLVYVAT-NLADGVPSRFSGSGSGTQYSLKIN-SLQSEDFGSYYCQHF WGTPYTFGGGTKL (SEQ ID NO: 21) encoded by the nucleotide sequence of SEQ ID NO: 22; and 93-22, H-chain variable region:
<u>MGWSRIFLFLLSITAGVHC</u>QVQLQQSGPELVKPGAS-VKISCKASGYAFSSSWMNW VKQRPGQGLEWI-GRIYPGDGDTNYNGKFKGKATL-TADKSSSTAYMQLSSLTSVDS AVYFCARGGNYGW-FAYWGQGTLVTVSAGS (SEQ ID NO: 29) encoded by the nucleotide sequence of SEQ ID NO: 30, and 93-22, L-chain variable region:
<u>METDTLLLWVLLLWVPGSTGD</u>IVLTQSPASLAVSLG-QRATISCRASKSVSTSGYSY MHWYQQKPGQPPKWY-LASNLESGVPARFSGSGSGTDFTLNIH-PVEEEDAATYY CQHSRELYTFGGGTKLGS (SEQ ID NO: 37) encoded by the nucleotide sequence of SEQ ID NO: 38. Underlines indicate the signal sequences.

The CDR (complementarity determining region) sequences of the antibodies were determined as follows:

```
92-13,
                                         (SEQ ID NO: 15)
     INDTYMH as VH CDR1, (SEQ ID NO: 17)
     RIDPANGNTKYD as VH CDR2,
     and (SEQ ID NO: 19)
     GSRFAY as VH CDR3, (SEQ ID NO: 23)
     RASENIYSNLA as VL CDR1, (SEQ ID NO: 25)
     VATNLAD as VL CDR2,
     and (SEQ ID NO: 27)
     QHFWGTPY as VL CDR3;
     and 93-22,
                                         (SEQ ID NO: 31)
     SSWMN as VH CDR1, (SEQ ID NO: 33)
     RIYPGDGDTNYN as VH CDR2,
     and
```

GGNYGWFAY as VH CDR3, (SEQ ID NO: 35)

RASKSVSTSGYSYMH as VL CDR1, (SEQ ID NO: 39)

LASNLES as VL CDR2, (SEQ ID NO: 41)
and

QHSRELY as VL CDR3. (SEQ ID NO: 43)

In addition, the amino acid sequences of the H chains and L chains of mouse monoclonal antibodies 92-13, 93-22 and 39-10 are determined as follows:
92-13, H chain: SEQ ID NO: 58 (encoded by the nucleotide sequence of SEQ ID NO: 57);
92-13, L chain: SEQ ID NO: 60 (encoded by the nucleotide sequence of SEQ ID NO: 59);
93-22, H chain: SEQ ID NO: 62 (encoded by the nucleotide sequence of SEQ ID NO: 61);
93-22, L chain: SEQ ID NO: 64 (encoded by the nucleotide sequence of SEQ ID NO: 63);
39-10, H chain: SEQ ID NO: 66 (encoded by the nucleotide sequence of SEQ ID NO: 65);
39-10, L chain: SEQ ID NO: 68 (encoded by the nucleotide sequence of SEQ ID NO: 67).

According to the determined sequence, specific primers for m92-13 variable region were designed: 5'-AATAGCGGC-CGCACCATGAAATGCAGCTGGGTTATCTT-3' (SEQ ID NO: 5) and 5'-AATAGCTAGCTGCAGAGACAGTGACCA-GAGTCC-3' (SEQ ID NO: 6) for heavy chain and 5'-AAT-AGCGGCCGCACCATGAGTGTGCCCACTCAGG-3' (SEQ ID NO: 7) and 5'-TTCCAGCTTGGTCCCCCC-3' (SEQ ID NO: 8) for light chain. Also, specific primers for m93-22 variable region were designed, 5'-AATAGCGGC-CGCACCATGGGATGGAGCCGGATCTTT-3' (SEQ ID NO: 53) and 5'-AATAGGATCCTGCAGAGACAGTGAC-CAGAGTCCCTT-3' (SEQ ID NO: 54) for heavy chain and 5'-AATAGCGGCCGCACCATGGAGACAGACA-CACTCCT-3' (SEQ ID NO: 55) and 5'-AATAGGATC-CCAGCTTGGTCCCCCCTCCGAACGT-3' (SEQ ID NO: 56) for light chain. To construct the expression vector for chimeric antibodies, two cassette vectors were prepared. The DNA fragment coding human IgG1 (CH1-CH3) was inserted into pQCXIH (Clontech) (pQCXCHIH) and the DNA fragment coding human Igκ (CL1) was inserted into pQCXIP (pQCXCLIP). For obtaining DNA fragments coding human IgG1 or human Igκ, human constant region library was prepared using cDNA from human PBMC (peripheral blood mononuclear cells) by the reported method (Liu, A. Y. et al., Proc. Natl. Acad. Sci. USA, Vol. 84, 3439-43, 1987; Reff, M. E. et al., Blood, Vol. 83, No. 2, 435-45, 1994). The DNAs coding variable region of m92-13 and m93-22 heavy chain and light chain were PCR amplified, sequenced and subcloned into pQCXCHIH and pQCXCLIP respectively using NotI and BamHI site. These vectors were co-transfected into CHO cells. Transfected cells were cultured in F-12 medium containing 500 µg/ml Hygromycin and 10 µg/ml Puromycin. When cells grow sub-confluently, the medium was exchanged to serum-free medium (CHO-S-SFM II; GIBCO) and chimeric antibody was purified from the supernatant of cultured cells using protein A-affinity column (GE Amersham) and was sequenced. The sequence of heavy chain of chimeric antibody ch92-13 comprises SEQ ID NO: 46 encoded by the nucleotide sequence of SEQ ID NO: 45; and the sequence of light chain of chimeric antibody ch92-13 comprises SEQ ID NO: 48 encoded by the nucleotide sequence of SEQ ID NO: 47. The sequence of heavy chain of chimeric antibody ch93-22 comprises SEQ ID NO: 49 encoded by the nucleotide sequence of SEQ ID NO: 50; and the sequence of light chain of chimeric antibody ch93-22 comprises SEQ ID NO: 52 encoded by the nucleotide sequence of SEQ ID NO: 51.

Example 8

Binding Activity of Chimeric Antibodies

Antibody-dependent cell cytotoxity (ADCC) activities induced by chimeric 92-13 and 93-22 were determined using LDH activity as described previously (Nagayama, S., et al. (2005). Oncogene, 24, 6201-6212). Fresh effector cells were isolated from heparinized peripheral blood of a healthy donor by Ficoll-Plaque (Amersham Bioscience). Effector cells (E) and target cells (T) (each, $5 \times 10^3$/well) were co-incubated for 6 h at 37° C. in quadruplicate at various E:T ratios, together with chimeric 92-13, chimeric 93-22 or non-immunized human IgG, in 0.1 ml of phenol red-free RPMI 1640 supplemented with 5% FBS in a 96-well plate. LDH released in the culture supernatants was determined by absorbance at 490 nm. The percentage of specific cytotoxicity was calculated according to the manufacturer's instructions.

Referring to the effector activity, both chimeric 92-13 and 93-22 induced ADCC specifically to the FZD10-overexpressing SYO-1 cells (FIGS. 8, a and c), but not to the FZD10-negative LoVo cells (FIGS. 8, b and d). Particularly, chimeric 92-13 showed higher induction of cytotoxicity as compared with chimeric 93-22; however, their activity depends on effector cell donor, possibly caused by polymorphism of Fc receptor.

Each of the applications and patents mentioned in this document, and each document cited or referenced in each of the above applications and patents are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments and that many modifications and additions thereto may be made within the scope of the invention. Indeed, various modifications of the described modes for carrying out the invention which are obvious to those skilled in molecular biology or related fields are intended to be within the scope of the claims. Furthermore, various combinations of the features of the following dependent claims can be made with the features of the independent claims without departing from the scope of the present invention.

The invention claimed is:

1. A method for treating a disease associated with Frizzled homologue 10 (FZD 10), comprising administering to a patient in need thereof an antibody or fragment thereof and a pharmaceutically acceptable carrier or excipient, wherein the disease associated with FZD 10 is synovial sarcoma, and wherein the antibody or fragment is selected from:
   (i) an antibody or fragment thereof, which comprises an H (heavy) chain V (variable) region comprising a complementarity determining region (CDR) having the amino acid sequences shown in SEQ ID NOs: 15, 17 and 19 and an L (light) chain V region comprising a CDR having the amino acid sequences shown in SEQ ID NOs: 23, 25 and 27, and which is capable of binding to a Frizzled homologue 10 (FZD10) protein or a partial peptide thereof; or
   (ii) an antibody or fragment thereof, which binds the FZD10 protein and in which the complementarity determining regions (CDRs) are the CDRs of the mouse monoclonal antibody 92-13 (FERM BP-10628).

2. The method according to claim 1, wherein the antibody is selected from the group consisting of a mouse antibody, a chimeric antibody, a humanized antibody, an antibody fragment, and single-chain antibody.

3. The method according to claim 1, wherein the antibody is a mouse antibody.

4. The method according to claim 3, wherein the mouse antibody comprises an H chain having the amino acid sequence shown in SEQ ID NO: 57 and/or an L chain having the amino acid sequence shown in SEQ ID NO: 59.

5. The method according to claim 3, wherein the mouse antibody is produced by the hybridoma clone 92-13 (FERM BP-10628).

6. The method according to claim 1, wherein the antibody is a chimeric antibody.

7. The method according to claim 6, wherein the chimeric antibody comprises an H chain V region having the amino acid sequence shown in SEQ ID NO: 13.

8. The method according to claim 6, wherein the chimeric antibody comprises an H chain having the amino acid sequence shown in SEQ ID NO: 46.

9. The method according to claim 6, wherein the chimeric antibody comprises an L chain V region having the amino acid sequence shown in SEQ ID NO: 21.

10. The method according to claim 6, wherein the chimeric antibody comprises an L chain having the amino acid sequence shown in SEQ ID NO: 48.

11. The method according to claim 6, wherein the chimeric antibody comprises an H chain V region having the amino acid sequence shown in SEQ ID NO: 13 and an L chain V region having the amino acid sequence shown in SEQ ID NO: 21.

12. The method according to claim 6, wherein the chimeric antibody comprises an H chain having the amino acid sequence shown in SEQ ID NO: 46 and an L chain having the amino acid sequence shown in SEQ ID NO: 48.

13. The method according to a claim 6, wherein the chimeric antibody further comprises a human antibody C (constant) region.

14. The method according to claim 1, wherein the antibody is a humanized antibody.

15. The method according to claim 14, wherein the humanized antibody further comprises a human antibody FR (framework) region and/or a human antibody C region.

16. The method according to claim 1, wherein the antibody is a chimeric antibody that further comprises a human antibody C (constant) region or which is a humanized antibody that further comprises a human antibody FR (framework) region and/or a human antibody C region.

17. The method according to claim 1, wherein the antibody is a chimeric antibody comprising:
   (i) an H chain V region having the amino acid sequence shown in SEQ ID NO: 13 and an L chain V region having the amino acid sequence shown in SEQ ID NO: 21; or
   (ii) an H chain having the amino acid sequence shown in SEQ ID NO: 46 and an L chain having the amino acid sequence shown in SEQ ID NO: 48.

18. The method according to claim 1, wherein the antibody or fragment thereof is labeled with a radioisotope label or a fluorescent label.

19. The method according to claim 18, wherein the radioisotope label is selected from the group consisting of $^{90}$yttrium ($^{90}$Y), $^{125}$iodine ($^{125}$I), and $^{111}$indium ($^{111}$In).

* * * * *